United States Patent
Takeuchi et al.

(10) Patent No.: US 10,653,667 B2
(45) Date of Patent: *May 19, 2020

(54) DRUG FOR PREVENTING, TREATING OR PREVENTING METASTASIS OF GIANT CELL TUMOR THAT OCCURS IN BONE OR SOFT PARTS, CHONDROSARCOMA, OR OSTEOSARCOMA, LOCAL INJECTION FOR ARTERIAL EMBOLIZATION, AND ARTIFICIAL BONE

(71) Applicant: NIPPON CHEMIPHAR CO., LTD, Tokyo (JP)

(72) Inventors: Akihiko Takeuchi, Ishikawa (JP); Hiroyuki Tsuchiya, Ishikawa (JP)

(73) Assignee: NIPPON CHEMIPHAR CO., LTD, Tokyo (JP)

( * ) Notice: Subject to any disclaimer, the term of this patent is extended or adjusted under 35 U.S.C. 154(b) by 118 days.

This patent is subject to a terminal disclaimer.

(21) Appl. No.: 15/023,896

(22) PCT Filed: Sep. 25, 2014

(86) PCT No.: PCT/JP2014/075542
§ 371 (c)(1),
(2) Date: Jul. 5, 2016

(87) PCT Pub. No.: WO2015/046388
PCT Pub. Date: Apr. 2, 2015

(65) Prior Publication Data
US 2016/0303073 A1 Oct. 20, 2016

(30) Foreign Application Priority Data

Sep. 25, 2013 (JP) .................................. 2013-199076

(51) Int. Cl.
| A61K 31/38 | (2006.01) |
| A61K 39/395 | (2006.01) |
| A61K 31/427 | (2006.01) |
| C07K 16/28 | (2006.01) |
| A61K 31/425 | (2006.01) |
| A61K 45/06 | (2006.01) |
| A61L 31/14 | (2006.01) |
| A61L 27/54 | (2006.01) |
| A61L 31/04 | (2006.01) |
| A61L 31/16 | (2006.01) |
| A61K 31/4439 | (2006.01) |
| G01N 33/50 | (2006.01) |

(52) U.S. Cl.
CPC ............ *A61K 31/38* (2013.01); *A61K 31/425* (2013.01); *A61K 31/427* (2013.01); *A61K 31/4439* (2013.01); *A61K 39/3955* (2013.01); *A61K 45/06* (2013.01); *A61L 27/54* (2013.01); *A61L 31/045* (2013.01); *A61L 31/048* (2013.01); *A61L 31/145* (2013.01); *A61L 31/146* (2013.01); *A61L 31/148* (2013.01); *A61L 31/16* (2013.01); *C07K 16/2875* (2013.01); *G01N 33/5011* (2013.01); *A61L 2430/36* (2013.01); *C07K 2317/21* (2013.01); *C07K 2317/76* (2013.01)

(58) Field of Classification Search
CPC .............................. A61K 31/38; A61K 31/192
IPC .......................................... A61L 27/54,31/044
See application file for complete search history.

(56) References Cited

U.S. PATENT DOCUMENTS

| 6,140,364 | A | * | 10/2000 | Falck | .................... | A61K 31/20 514/552 |
| 6,635,771 | B2 | | 10/2003 | McKew et al. | | |
| 6,797,708 | B2 | | 9/2004 | McKew et al. | | |
| 6,984,735 | B2 | | 1/2006 | McKew et al. | | |
| 7,101,875 | B2 | | 9/2006 | McKew et al. | | |
| 7,605,156 | B2 | | 10/2009 | McKew et al. | | |
| 7,713,964 | B2 | | 5/2010 | McKew et al. | | |
| 7,906,548 | B2 | | 3/2011 | McKew et al. | | |
| 2003/0144282 | A1 | | 7/2003 | McKew et al. | | |
| 2003/0166649 | A1 | | 9/2003 | McKew | | |
| 2003/0220374 | A1 | | 11/2003 | Needleman | | |
| 2004/0266834 | A1 | * | 12/2004 | Copland, III | ........ | A61K 31/426 514/342 |
| 2005/0209292 | A1 | | 9/2005 | Chuang et al. | | |
| 2006/0088601 | A1 | * | 4/2006 | Overby et al. | ......... | A61K 35/34 424/548 |
| 2006/0240014 | A1 | * | 10/2006 | Sukhatme | .............. | A61K 31/40 424/145.1 |
| 2007/0232586 | A1 | | 10/2007 | Ohmoto et al. | | |

(Continued)

FOREIGN PATENT DOCUMENTS

CN 101628888 A 1/2010
EP 2 832 367 2/2015

(Continued)

OTHER PUBLICATIONS

Wassef et al (Journal of Biomedical Materials Research, Part B: Applied Biomaterials, 2008, vol. 86B, pp. 63-73) (Year: 2008).*

(Continued)

*Primary Examiner* — Karen A. Canella
(74) *Attorney, Agent, or Firm* — Greenblum & Bernstein, P.L.C.

(57) ABSTRACT

The present invention provides an agent for prophylactic treatment, therapeutic treatment, or prevention of metastasis of giant cell tumor occurring in a bone and soft tissue, chondrosarcoma, or bone sarcoma, a local infusion for artery embolization, and an artificial bone, which comprises a substance having a PPARγ-agonistic activity and/or a PPARγ expression-inducing activity as an active ingredient. The agent for prophylactic treatment, therapeutic treatment, or prevention of metastasis, the local infusion for artery embolization, and the artificial bone of the present invention are a radical therapeutic agent or radical therapeutic material that can cause apoptosis in giant cell tumor occurring in a bone and soft tissue, chondrosarcoma, or bone sarcoma to make the tumor disappear, and can induce differentiation of the tumor into fat cells to make the tumor disappear.

14 Claims, 45 Drawing Sheets

(56) References Cited

U.S. PATENT DOCUMENTS

| | | | |
|---|---|---|---|
| 2008/0279938 A1 | 11/2008 | Cho | |
| 2009/0306074 A1 | 12/2009 | Darcy et al. | |
| 2011/0224675 A1* | 9/2011 | Tofighi | A61B 17/8811 606/94 |
| 2015/0045396 A1 | 2/2015 | Takeuchi et al. | |
| 2015/0297793 A1* | 10/2015 | McKay | A61L 27/3683 424/529 |

FOREIGN PATENT DOCUMENTS

| | | | |
|---|---|---|---|
| JP | H06192084 | * | 7/1994 |
| JP | 2004-073859 | | 3/2004 |
| JP | 2005-200419 | | 7/2005 |
| JP | 2005-323802 | A | 11/2005 |
| JP | 2005-343802 | | 12/2005 |
| JP | 2006/501136 | | 1/2006 |
| JP | 2007-015930 | | 1/2007 |
| JP | 2009-533467 | | 9/2009 |
| JP | 6205403 | B2 | 9/2017 |
| WO | 2005/103012 | | 11/2005 |
| WO | 2008/026729 | | 3/2008 |
| WO | 2008/109727 | | 9/2008 |
| WO | 2008/109731 | | 9/2008 |
| WO | 2008/109737 | | 9/2008 |
| WO | 2010/001601 | | 1/2010 |
| WO | 2011/073788 | | 6/2011 |
| WO | 2011/103130 | | 8/2011 |
| WO | 2011/103134 | | 8/2011 |
| WO | 2011/149841 | | 12/2011 |
| WO | 2013/146435 | | 10/2013 |

OTHER PUBLICATIONS

Grommes et al (Molecular Pharmacology, 2006, vol. 70, pp. 1524-1533) (Year: 2006).*
The abstract of Langova et al (Australian Veterinary Practitioner, 2004, vol. 34, pp. 98-102) (Year: 2004).*
Wurthwein et al (European Journal of Clinical Pharmacology, 2005, vol. 60, pp. 883-888) (Year: 2005).*
Tsai et al (The Lancet Oncology, 2005, vol. 6, pp. 997-999) (Year: 2005).*
Kasper et al (International Journal of Clinical Oncology, 2005, vol. 10, pp. 438-440) (Year: 2005).*
The abstract of Yan (CN 1458158, 20031126) (Year: 2003).*
Sardone et al (Diabetes, 2011, vol. 60, pp. 3271-3278) (Year: 2011).*
Jones et al (Arthritis and Rheumatism, 2010, vol. 62, pp. 2726-2735) (Year: 2010).*
Hirabayashi et al (Journal of Controlled Release, 2001, vol. 79, pp. 183-191) (Year: 2001).*
Cheng et al (Calcified Tissue International, 2004, vol. 75, pp. 71-77) (Year: 2004).*
Machine Translation of JPH06192084 (Year: 2019).*
Liu et al (Chinese Medical Journal, 2012, vol. 125, pp. 3719-3724) (Year: 2012).*
Stangier and Roth (Journal of International Medical Research, 2000, vol. 28, pp. 149-167) (Year: 2000).*
Takeuchi et al., "Complete Necrosis of a Giant Cell Tumor with High Expression of PPARγ: A Case Report"; Anticancer Research 33, XP055345576; May 1, 2013; pp. 2169-2174.
Takeuchi et al., "Activation of peroxisome proliferator-activated receptor gamma is a novel therapeutic means for giant cell tumor"; P4:103; Abstracts 26th European Musculoskeletal Oncology Society Meeting, XP055345586; May 1, 2013; pp. 1.
Extended European Search Report issued in Patent Application No. 14847606.2, dated Feb. 23, 2017.
Takeuchi et al., J. Jpn. Orthop. Assoc., vol. 86, No. 8, p. S1319, 2012; Feb. 9, 2018.
Woo et al., "Anticancer Activity of Thymoquinone in Breast Cancer Cells: Possible Involvement of PPAR-γ Pathway", Biochemical Pharmacology, vol. 82, pp. 464-475, 2011.
Papi et al., "RXRγ and PPARγ Ligands in Combination to Inhibit Proliferation and Invasiveness in Colon Cancer Cells", Cancer Letters, vol. 297, pp. 65-74, 2010.
Takahashi et al., "Activation of PPARγ Inhibits Cell Growth and Induces Apoptosis in Human Gastric Cancer Cells", FEBS Letters, vol. 455, pp. 135-39, 1999.
Yamazaki et al.., "Nonsteroidal Anti-Inflammatory Drugs Induce Apoptosis in Association with Activation of Peroxisome Proliferator-Activated Receptor γ in Rheumatoid Synovial Cells", The Journal of Pharmacology and Experimental Therapeutics, vol. 302, No. 1, pp. 18-25, 2002.
Kitamura et al., "Peroxisome Proliferator-activated Receptor γ Induces Growth Arrest and Differentiation Markers of Human Colon Cancer Cells", Jpn. J. Cancer Res., vol. 90, pp. 75-80, 1999.
Kim et al., "Apoptotic Action of Peroxisome Proliferator-Activated Receptor-γ Activation in Human Non-Small-Cell Lung Cancer Is Mediated via Proline Oxidase-Induced Reactive Oxygen Species Formation", Molecular Pharmacology, vol. 72, No. 3, pp. 674-685, 2007.
Nishida et al., "Inhibition of Human Chondrosarcoma Cell Growth via Apoptosis by Peroxisome Proliferator-Activated Receptor-γ", British Journal of Cancer, vol. 86, No. 8, pp. 1303-1309, 2002.
Li et al., "Growth Inhibition and Differentiation Induced by Peroxisome Proliferator Activated Receptor Gamma Ligand Rosiglitazone in Human Melanoma Cell Line A375", Medical Oncology, vol. 23, No. 3, pp. 393-402, 2006.
Vaish et al., "The Role of NF-κb and PPARγ in Experimentally Induced Colorectal Cancer and Chemoprevention by Cyclooxygenase-2 Inhibitors", Tumor Biol., vol. 31, No. 5, pp. 427-436, 2010.
Xie et al., "Rosiglitazone and ATRA on Gastric Cancer SGC7901 Cell Line Proliferation In Vitro", Journal of Chinese Physician, vol. 12, No. 6, pp. 743-747, 2010 (including English language abstract).
International Preliminary Report on Patentability for PCT/JP2013/057706 dated Oct. 1, 2014, along with an English language translation.
International Search Report for PCT/JP2013/057706 dated May 28, 2013, along with an English language translation.
Otsuka, "Development of Endogenous Signal Responsive Implanted Drug Delivery System in Hard Tissues", Advances in Pharmaceutical Sciences, vol. 14, pp. 37-44, 1998.
Office Action issued in Japanese Patent Application No. 2014-507736, dated Aug. 25, 2015, along with an English language translation.
Office Action issued in New Zealand Patent Application No. 700872, dated Sep. 28, 2015.
Nishida et al., "Chondrosarcoma Peroxisome Proliferator-Activated Receptor", PPAR Research, vol. 274, No. 24, pp. 1-7, 2008.
De Chiara et al., "Multicentric Giant Cell Tumor with Viral-like Inclusions Associated with Paget's Disease of Bone: A Case Treated by Steroid Therapy", Oncology Reports, vol. 5, pp. 317-320, 1998.
Extended European Search Report issued in EP Patent Application No. 13769796.7, dated Nov. 13, 2015.
New Zealand Office Action in respect to New Zealand Application No. 700872, dated Sep. 14, 2016.
New Zealand Office Action in respect to New Zealand Application No. 700872, dated Aug. 11, 2016.
New Zealand Further Examination Report in respect to New Zealand IP No. 700872, dated Apr. 21, 2016.
The Journal of the Japanese Orthopedic Association, 2013, 87(8): 1-8-22.
2013 AAOS (American Association of Orthopedic Surgeons) Annual Meeting Abstract Paper 341.
26th Eur. Musculoskeletal Oncology Society Meeting 2013, Abstract P4: 103.
The Journal of the Japanese Orthopedic Association, 2013; 87(6): 1-2-FP3-8.
ISOLS 2013 Abstract N° 205 (Annual Meeting of International Society of Limb Salvage 2013, Abstract N° 310).
Anticancer Research, 2013; 33, pp. 2169-2174.
The Journal of the Japanese Orthopedic Association, 2013; 87(8): 1-8-20.
ISOLS 2013 Abstract N° 205 (Annual Meeting of International Society of Limb Salvage 2013, Abstract N° 205).

(56) References Cited

OTHER PUBLICATIONS

Naruse T. et al., Carcinogenesis, 2006, vol. 27, No. 3, pp. 584-592.
Lee E. J. et al., Exp Mol Med, 2007, vol. 39, No. 4, pp. 469-476.
Lili Fu et al., Chemotherapy, 2009, vol. 55, No. 6, pp. 468-476.
Long H. et al., Chinese Journal of Bone and Joint, 2012, vol. 1, No. 2, pp. 136-140.
Aizawa, The Journal of the Japanese Orthopedic Association, 2009, vol. 83, No. 8, pp. S1259.
Shen Z. N. et al., Biochem Biophys Res Commun, 2005, vol. 328, No. 2, pp. 375-382.
International Search Report and Written Opinion issued in PCT/JP2014/075542 with English Translation, dated Dec. 16, 2014.
International Preliminary Report on Patentability issued in PCT/JP2014/075542 with English Translation, dated Mar. 29, 2016.
Japanese Notification of Reasons for Refusal with English Translation in respect to Japanese Appl. No. 2015-252893, dated Nov. 1, 2016.
Pain Clinic, 2009, 30(11), pp. 1587-1591.
Ventafridda et al., The Journal of International Medical Research, 1990, 18, 21-29.
The Journal of Practical Pharmacy, 2010, 61(10), pp. 3110-3115.
Japanese Office Action dated Mar. 21, 2017 issued in Japanese Patent Application No. 2015-252893 with machine English translation.
Australian Examination Report No. 2 in respect to Australian Application No. 2013238126, dated Aug. 31, 2017.
European Office Action in respect to European Application No. 13769796.7, dated Sep. 15, 2017.
Restriction Requirement in respect to U.S. Appl. No. 14/387,981, dated Nov. 18, 2015.
Office Action in U.S. Appl. No. 14/387,981, dated Feb. 12, 2016.
Final Action in U.S. Appl. No. 14/387,981, dated Sep. 14, 2016.
Office Action in U.S. Appl. No. 14/387,981, dated Oct. 5, 2017.
Australian Office Action issued in Australian Patent Appl. No. 2013238126, dated Dec. 21, 2016.
Japanese Office Action issued with respect to Application No. 2015-539360, dated Jul. 3, 2018.
Bernardo et al., "Nuclear receptor peroxisome proliferator-activated receptor-y is activated in rat microglial cells by the anti-inflammatory drug HCT1026, a derivative of flurbiprofen", Journal of Neurochemistry, 2005, 92, pp. 895-903.
Zou et al., "PPARy agonists inhibit TGF-B-PKA signaling in glomerulosclerosis", Acta Pharmacologica Sinica, 2010, 31, pp. 43-50.
Maeyama et al., "Nuclear Receptors as Targets for Drug Development: Peroxisome Proliferator-Activated Receptor y in Mast Cells: Its Roles in Proliferation and Differentiation", Journal of Pharmacological Sciences, 97, pp. 190-194, 2005.
Dufresne et al., "Giant-cell tumor of bone, anti-RANKL therapy", BoneKEy Reports 1, Article No. 149, pp. 1-8, 2012.
Final Office Action issued with respect to U.S. Appl. No. 14/387,981, dated Aug. 10, 2018.
European Office Action issued in the corresponding European patent application No. 14847606.2, dated Oct. 15, 2018.
Matsumoto et al., "NSAID zaltoprofen processes novel anti-nociceptive mechanism through blockage of B2-type bradykinin receptor in nerve endings", Neuroscience Letters, 2006, vol. 397, No. 3, p. 249-253, XP55508938.
Japanese Office Action issued in corresponding Japanese patent application No. 2015-539360, dated Nov. 6, 2018, with English machine translation.
Diaz-Rodriguez et al., "Effect of acetaminophen (paracetamol) on human osteosarcoma cell line MG63", Acta Pharmacol Sin, 2010, vol. 31, No. 11, p. 1495-1499

E. De Luna-Bertos et al., "Effect of Aspirin on Cell Growth of Human MG-63 Osteosarcoma Line", ScientificWorldJournal, 2012, Article ID 834246, including pp. 1-6.
Diaz-Rodriguez et al., "Effects of Indomethacin, Nimesulide, and Diclofenac on Human MG-63 Osteosarcoma Cell Line", Bio Res Nurs, 2012, vol. 14, No. 1, p. 98-107
European Office Action from Application No. 14847606.2, dated Feb. 13, 2018.
Canadian Office Action issued with respect to Canadian Application No. 2,868,311, dated Dec. 19, 2018.
Office Action dated Sep. 19, 2019 issued in Canadian Application No. 2,868,311.
Potter, Am. Fam. Physician, 72(3), 436-437, Aug. 1, 2005.
Office Action dated Jul. 29, 2019 (with English translation) issued in Korean patent application No. 10-2014-7029881.
English translation of Second Office Action dated May 8, 2019 issued in the corresponding Chinese Patent Application No. 201610647601.
Chinese Examiner's Summary; Excerpts from 2nd Chinese Official Action, dated May 8, 2019, in Chinese Patent Application No. 201610647601pertaining to World Pharmacy, 1995, pp. 306-307.
Paknesban et al., Investigative Ophthalmology & Visual Science, Sep. 2008, vol. 49, No. 9, pp. 3909-3913.
First Office Action dated Sep. 4, 2018 issued in the corresponding Chinese Patent Application No. 201610647601 with its English machine translation.
Second Office Action dated May 8, 2019 issued in the corresponding Chinese Patent Application No. 201610647601.
World Pharmacy, 1995, pp. 306-307.
Ming H. Zheng, "Gene Expression of Vascular Endothcial Growth Factor in Giant Cell Tumors of Bone", Human Pathology, pp. 804-812, Jul. 2000.
Chin J Pancreatol, Oct. 2007, vol. 7, No. 5, pp. 313-316.
First Office Action dated Jan. 27, 2016 issued in the corresponding Chinese Patent Application No. 201380016296 with its English machine translation.
Second Office Action dated Dec. 14, 2016 issued in the corresponding Chinese Patent Application No. 201380016296 with its English machine translation.
Third Office Action dated Sep. 5, 2017 issued in the corresponding Chinese Patent Application No. 201380016296 with its English machine translation.
Office Action dated Jan. 6, 2020 issued in Chinese Application No. 201610647601.0 with English translation.
Handbook of Orthopaedic Resident, editor-in-chief: LIU Shiqing, pp. 505-506, Jan. 31, 2005, discussed in English translation of Chinese Office Action.
Contemporary Multimedia Atlas of Needle Aspiration Cytology Diagnostics, editor-in-chief: Wang Yongcai Tianjin Science & Technology Press, p. 385, Jul. 31, 2004, discussed in English translation of Chinese Office Action.
Extended European Search Report dated Feb. 28, 2020 issued in European Patent Application No. 19210770.4.
Korean Office Action dated Feb. 28, 2020 issued in Korean Patent Application No. 10-2014-7029881, with English translation.
Balke Maurice et al: Bmc Cancer Biomed Central, London, GB, vol. 10, No. 1, Aug. 29, 2010 (Aug. 29, 2010), p. 462, 8 pages.
Hamid Namazi: Annals of Surgical Oncology, Springer-Verlag, NE, vol. 15, No. 8, Jan. 23, 2008 (Jan. 23, 2008), pp. 2350-2351.
Arne Streitbuger et al: International Orthopedics, Springer, Berin, DE, vol. 35, No. 9, Oct. 2, 2010 (Oct. 2, 2010), pp. 1369-1373.
Lyles et al. Journal of Bone and Mineral Research, vol. 16, No. 8, pp. 1379-1387 (2001).

\* cited by examiner

Fig. 79

Giant cell tumor of bone : 13 cases

| case | age | Gender* | site | primary or recurrence | follow-up (month) | response rate | postoperative (month) | period of treatment /administration (month) | recurrence | comments | picture of affected site |
|---|---|---|---|---|---|---|---|---|---|---|---|
| a | 34 | F | pelvis | recurrence (3 times) | 25 | PR | 10 | 25 | No | | Fig33~Fig36 |
| b | 32 | F | pelvis | primary | 7 | SD | 2 | 7 | No | administered after denosumab-treatment | |
| c | 38 | M | proximal site of left fibula | recurrence | 21 | SD | 19 | 21 | No | | Fig81 |
| d | 21 | M | distal site of right tibia | primary | 3 | SD | 1 | 3 | No | | Fig82 |
| e | 30 | M | proximal site of left fibula | pulmonary metastasis | 19 | SD | | 19 | | | Fig83 |
| f | 25 | F | proximal site of right humerus | Recurrence (5 times) | 20 | SD | 18 | 20 | No | | |
| g | 67 | F | pelvis | primary | 11 | SD | 8 | 11 | No | | |
| h | 27 | M | distal site of right thighbone | primary | 20 | SD | 18 | 20 | No | | |
| i | 68 | F | pelvis | recurrence | 26 | SD | | 26 | | suspension due to epigastralgia, administered after improvement | |
| j | 32 | M | sacrum | primary | 26 | SD | | 26 | | combined application of Zometa and stent | |
| k | 29 | M | distal site of right thighbone | recurrence | 22 | SD | 13 | 22 | No | | |
| l | 31 | M | left knee | primary | 18 | SD | 16 | 3 | No | Approximately half-administered | |
| m | 21 | M | proximal site of right tibia | multiple pulmonary metastasis | 18 | PD→SD→PD | | 18 | | combined application of Zometa after denosumab-treatment | |

*: F: female; M: Male

Fig. 80

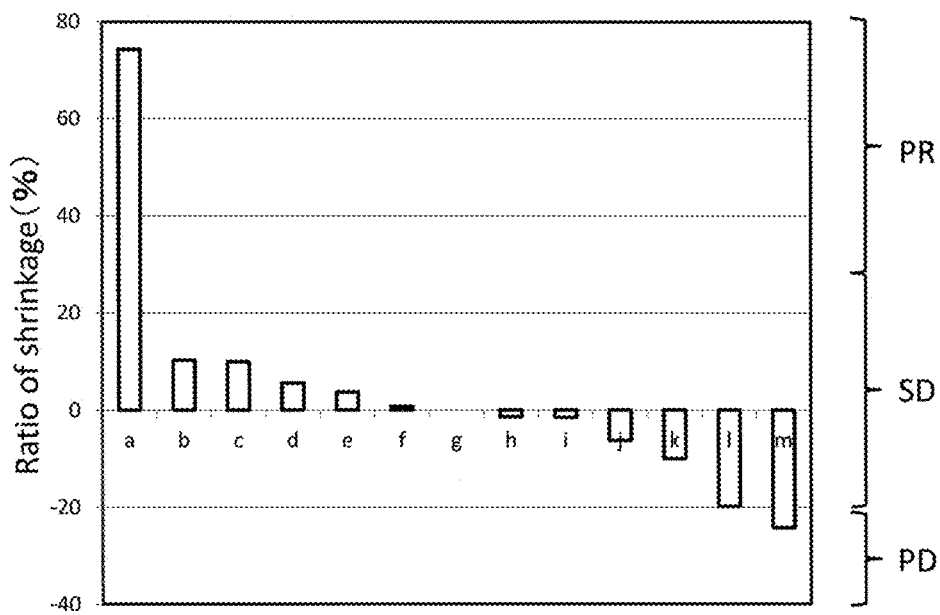

Ratio of giant cell tumor shrinkage

Giant cell tumor of bone  Case c

Giant cell tumor of bone  Case d

Fig. 83

Giant cell tumor of bone  Case e

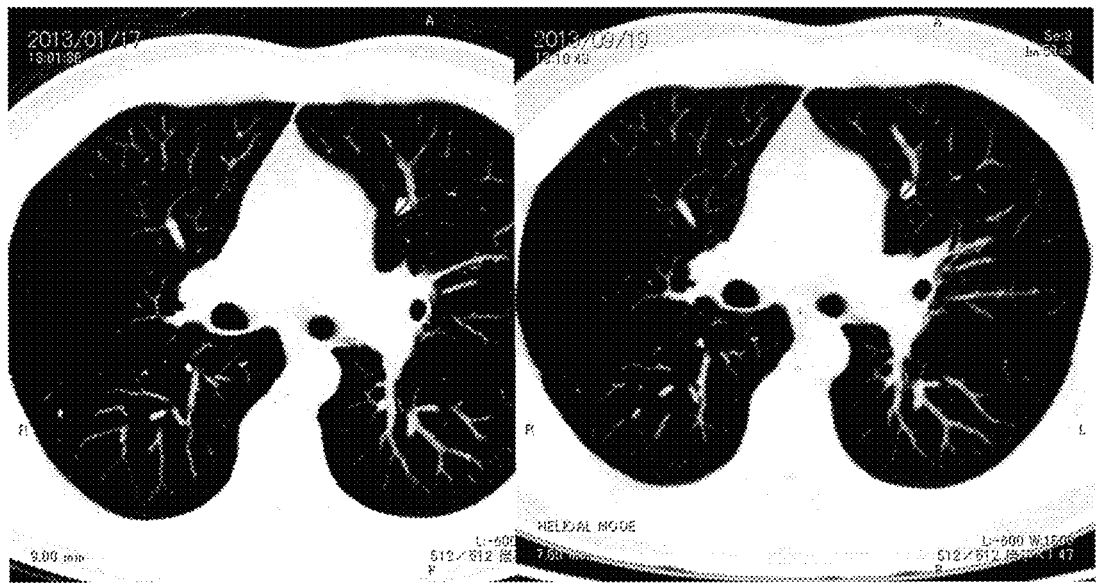

Fig. 84

Karnofsky Performance Status

| | SCORE | Patient's condition |
|---|---|---|
| Normal activities are possible. Special nursing is not needed. | 100 | Normal; No patient's report of the disease; No clinical symptoms |
| | 90 | Although slight clinical symptoms are present, normal activities are possible. |
| | 80 | Although considerable clinical symptoms are present, normal activities are possible with efforts. |
| Working is impossible; Living at home is possible, and nursing is demanded personally; Various levels of assistance are needed. | 70 | Although self-care is possible, normal activities and working are impossible. |
| | 60 | Although one can do what are needed for oneself, assistance is sometimes needed. |
| | 50 | Nursing and periodical medical intervention are needed in consideration of conditions of disease. |
| Self-care is impossible; Nursing like that provided in facility or hospital is needed; there is possibility that disease is developed rapidly. | 40 | Incapable of movement; adequate medication and nursing are needed. |
| | 30 | Incapable of movement; Although hospital stay is needed, death is not faced. |
| | 20 | Very severe condition; hospital stay is needed and medication is fully needed. |
| | 10 | Death is faced |
| | 0 | death |

Fig. 85

Giant cell tumor of bone : 13 cases

| case | Karnofsky Performance Status | | X-ray hardening | | CT (hardening) | | Rate of shrinkage (%) |
|---|---|---|---|---|---|---|---|
| | Before taking medicine | After taking medicine | Before taking medicine | After taking medicine | Before taking medicine | After taking medicine | |
| a | 80 | 90 | absence | presence | absence | presence | 74.2 |
| b | 90 | 100 | absence | presence | absence | presence | 10.2 |
| c | 80 | 90 | absence | absence | absence | absence | 9.9 |
| d | 80 | 90 | presence | presence | No test before taking medicine | presence | 5.5 |
| e | 100 | 100 | Evaluation could not be made due to pulmonary metastasis | | | | 3.7 |
| f | 90 | 90 | absence | absence | absence | absence | 0.8 |
| g | 80 | 100 | absence | absence | absence | presence | 0 |
| h | 90 | 90 | absence | absence | absence | absence | -1.3 |
| i | 70 | 70 | absence | absence | absence | presence | -1.5 |
| j | 50 | 90 | absence | presence | absence | presence | -6.2 |
| k | 80 | 90 | absence | absence | absence | absence | -10.0 |
| l | 80 | 80 | absence | absence | absence | absence | -19.8 |
| m | 90 | 100 | Evaluation could not be made due to pulmonary metastasis | | | | -24.3 |

Fig. 86

PVNS

| | | | | | | | | | |
|---|---|---|---|---|---|---|---|---|---|
| Diffuse form | | | | | | | | | |
| case | age | gender | site | primary/recurrence | Duration of therapy (month) | Duration of administration (month) | Response rate | comments | Picture of affected area |
| a | 65 | male | Shoulder joint | primary | 5 | 5 | PR | | Fig. 88 |
| b | 38 | female | Right knee | recurrence | 27 | 27 | SD | | Fig. 41~Fig.44 |
| c | 53 | female | Right knee | recurrence | 23 | 23 | SD | | Fig. 88 |
| d | 37 | male | Ankle joint | primary | 18 | 18 | SD | | |
| f | 24 | female | Knee joint | primary | 9 | 9 | SD | | |
| g | 64 | male | Left knee | recurrence | 27 | 24 | SD | | |
| h | 16 | female | Right ankle joint | primary | 18 | 18 | SD | Operation was conducted. | |
| i | 26 | male | Right knee | recurrence | 23 | 23 | SD | Operation was conducted. | |
| j | 26 | female | Right knee | recurrence | 28 | 28 | SD | | |
| k | 62 | female | Left knee | recurrence | 23 | 10 | SD | Cessation was requested. | Fig. 37~Fig.40 |
| l | 31 | female | Left ankle joint | recurrence | 29 | 25 | | Medicine was taken after operation. No recurrence | |
| m | 30 | female | Left knee | recurrence | 27 | 13 | | Medicine was taken after operation. No recurrence | |
| n | 38 | female | Ankle joint | recurrence | 13 | 13 | | Medicine was taken after operation. No recurrence | |

| | | | | | | | | |
|---|---|---|---|---|---|---|---|---|
| Focal form | | | | | | | | |
| | age | gender | site | Primary/recurrence | Duration of therapy | Duration of administration | results | comments |
| e | 40 | male | Left wrist joint | recurrence | 17 | 17 | SD | Operation was conducted. |

Diffuse form PVNS case a

Diffuse from PVNS case c

KPS and rate of shrinkage of PVNS 11 cases (diffuse form: 10 cases, focal form: 1 case)

|  | case | Karnofsky Performance Status | | Rate of shrinkage |
|---|---|---|---|---|
|  |  | before | after |  |
| Diffuse form | a | 70 | 100 | 71.5 |
|  | b | 70 | 100 | 11.4 |
|  | c | 80 | 90 | 10.3 |
|  | d | 80 | 90 | 10.3 |
|  | f | 70 | 70 | 0.7 |
|  | g | 90 | 90 | 0.3 |
|  | h | 90 | 90 | 0.2 |
|  | i | 90 | 90 | -0.8 |
|  | j | 90 | 90 | -5.1 |
|  | k | 90 | 90 | -7.2 |
| Focal form | e | 90 | 90 | 3.8 |

DRUG FOR PREVENTING, TREATING OR PREVENTING METASTASIS OF GIANT CELL TUMOR THAT OCCURS IN BONE OR SOFT PARTS, CHONDROSARCOMA, OR OSTEOSARCOMA, LOCAL INJECTION FOR ARTERIAL EMBOLIZATION, AND ARTIFICIAL BONE

TECHNICAL FIELD

The present invention relates to an agent for prophylactic treatment, therapeutic treatment, or prevention of metastasis of giant cell tumor occurring in a bone and soft tissue, chondrosarcoma, or bone sarcoma, and the like, which uses a substance having a PPARγ-agonistic activity and/or a PPARγ expression-inducing activity. The present invention also relates to a local infusion for artery embolization or artificial bone, which comprises a substance having a PPARγ-agonistic activity and/or a PPARγ expression-inducing activity. The present invention further relates to a screening method for selecting a substance that induces apoptosis or fat cell differentiation in giant cell tumor occurring in bone and soft tissue, chondrosarcoma, or bone sarcoma, as an agent for prophylactic treatment, therapeutic treatment, or prevention of metastasis of giant cell tumor occurring in bone and soft tissue, chondrosarcoma, or bone sarcoma.

BACKGROUND ART

As giant cell tumors occurring in a bone and soft tissue, there are known osteoclastoma occurring in a bone (giant cell tumor of bone, henceforth referred to as "GCTB"), giant cell tumor of tendon sheath-localized type occurring in a soft tissue (henceforth referred to as "GCTT"), pigmented villonodular synovitis (henceforth referred to as "PVNS"), and the like. In this specification, GCTB, GCTT, and PVNS are collectively referred to as giant cell tumors. In general, among the giant cell tumors, especially the giant cell tumor of tendon sheath (GCTT) and the pigmented villonodular synovitis (PVNS) may be generically named giant cell tumors of tendon sheath. In this specification, the term giant cell tumor of tendon sheath refers to the giant cell tumor of tendon sheath-localized type (GCTT) in a narrow sense, and for referring to the giant cell tumors of tendon sheath in a broad sense, the term tenosynovial giant cell tumors is used.

As a tumor occurring in a bone and soft tissue, chondrosarcoma is also known. Similarly, as a malignant tumor primarily occurring in a bone tissue, bone sarcoma is known.

Giant cell tumor of bone (GCTB) is a benign tumor frequently occurring in circumferences of the knee joints of young to middle- or advanced-aged persons, and accounts for 3 to 8% of the primitive bone tumors, and 15 to 20% of benign bone tumors. The morbidity of the giant cell tumor of bone (GCTB) is slightly higher in women, and patients' man-and-woman ratio is 1:1.3 to 1.5. Giant cell tumor of bone (GCTB) frequently occurs in 20 to 45 years old persons, and it is said that about 150 persons newly develop this disease in every year in Japan. Giant cell tumor of bone (GCTB) accounts for about 5% of all bone tumors, and about 20% of benign bone tumors.

As for occurring positions of giant cell tumor of bone (GCTB), it frequently occurs in long tubular bones, and it occurs in a distal end of the thighbone (namely, just above the knee) or a proximal end of the tibia (namely, just below the knee) in approximately half of the total cases. Next to these positions, giant cell tumor of bone (GCTB) frequently occurs at a distal end of the radius (namely, the jointing position of the thumb on the radius, which is the bone on the side of the thumb among the two bones connecting the elbow and the wrist), a proximal end of the humerus (namely, just under the shoulder), and the sacrum (namely, the inverse triangle bone near the inferior extremity of the backbone, locating at the center of the pelvis), which are mentioned in the descending order of occurring frequency. There are no symptoms peculiar to giant cell tumor of bone (GCTB), and the subjective symptoms are such nonspecific symptoms as a pain of affected part due to microfracture caused by reduction of bone strength, spontaneous pain, load-bearing pain, swelling, sense of heat, and difficulty in moving joint.

Although giant cell tumor of bone (GCTB) is classified as benign tumor, it shows characteristics between those of malignant and benign tumors, such as high proliferation velocity and high recurrence rate of 10 to 30%. In several percents of the cases of giant cell tumor of bone, it metastasizes to the lung within 1 to 10 years, and 25% of such patients die from proliferation of the tumor. Giant cell tumor of bone (GCTB) may rarely convert into highly malignant sarcoma, and it is reported that, as for the prognosis of such cases, five-year survival rate of such patients treated with chemotherapeutic treatment and extensive resection was 50%.

Since giant cell tumor of bone occurring before stop of increase of body height due to closing of the epiphyseal plate, or giant cell tumor of bone found at an early stage exists at the metaphysis (namely, an end part of diaphysis of a long tubular bone locating on the diaphysis side with respect to the epiphysis constituting a part of joint), it is fundamentally considered to be a tumor that occurs in the metaphysis and quickly infiltrates in the epiphysis. Hyperplasia of multinucleated giant cells and monocyte cells constitutes the major part of the pathological findings, and spindle cells are observed between them. The morphology and functions of the multinucleated giant cells are similar to those of osteoclasts. It is thought that the body of the tumor of giant cell tumor of bone consists of spindle cells similar to fibroblasts and osteoblasts existing in the stroma, and the multinucleated giant cells and monocyte cells are cells gathering in response to a cytokine produced by the tumor cells. Although it is considered that giant cell tumor of bone is probably a tumor originating in undifferentiated mesenchymal cells in the bone marrow, cell origin thereof is unknown.

There is only ablative operation as the radical therapy of giant cell tumor of bone (GCTB). In usual ablative operations, phenol treatment, alcohol treatment, zinc chloride treatment, freezing with liquid nitrogen, and thermotherapeutic treatment using heat of polymerization of methyl methacrylate bone cement are performed after curettage or excision of the lesion, for the purpose of annihilating remaining tumor cells to prevent recurrence, and the recurrence rate of 30 to 50% observed without such treatments as mentioned above is thereby successfully lowered to 10 to 25%.

Although it is rare for giant cell tumor of bone (GCTB) to follow a fatal process, it is a disease of which repetition of recurrence gradually spoils motor functions of bones and joints, and at the same time, for which surgical operations cause nerve damages to greatly degrades the quality of life, and therefore there is desired a therapeutic treatment that is not based on surgical operation, but on an internal medical therapeutic treatment, and does not invite recurrence or metastases to the lung.

As for a therapeutic treatment for giant cell tumor of bone (GCTB) not based on surgical operation, there is investigated application to giant cell tumor of bone of denosumab (trade name, Ranmark), which comprises an anti-RANKL human monoclonal antibody, and is clinically used as a therapeutic agent for bone diseases caused by multiple myeloma and bone diseases caused by solid carcinoma metastases. However, said medicament is a therapeutic agent aiming at suppressing the functions of the RANKL protein required for formation and activation of osteoclasts to prevent bone destruction, and is not a therapeutic agent aiming at suppressing tumor proliferation itself, and as for the administration route, it should be subcutaneously administered.

Therefore, there is desired a therapeutic agent for giant cell tumor of bone (GCTB) that can be orally administered, and can suppress tumor proliferation, per se. Giant cell tumor of tendon sheath (GCTT) is a soft tissue tumor that frequently occurs around joints and tendon sheaths at peripheries of arms and legs, and in particular, cases thereof developing the tumor adjacently to the tendon sheaths around interphalangeal joints of fingers are overwhelmingly frequently observed. Giant cell tumor of tendon sheath (GCTT) occurs around joints of fingers or on flexor tendons in about 85% of the cases, and it next frequently occurs in foot. Giant cell tumor of tendon sheath (GCTT) may infiltrate in bones. Although giant cell tumor of tendon sheath (GCTT) is synonymous with nodular tenosynovitis, but it is not an inflammatory disease, but it is a tumor. Although there is not known any report describing exact occurrence frequency of giant cell tumor of tendon sheath (GCTT), it is a disease of which number of cases is next to those of lipoma and neurilemmoma among benign soft tissue tumors that are excised by orthopedists for the purpose of therapeutic treatment, and it is not a rare disease. Giant cell tumors of tendon sheath (GCTT) frequently occurs in adults in their thirties to fifties, and especially frequently occurs in women, and the patients' man-and-woman ratio was reported to be 1:2. There are no special subjective symptoms of giant cell tumor of tendon sheath (GCTT), and it occurs as hypodermic tumor in fingers with no substantial pain, shows slow proliferation, and generally passes several years until it is diagnosed by a medical examination of a medical practitioner.

As the pathology of giant cell tumor of tendon sheath (GCTT), orbicular-ovate to spindle-shaped histiocyte-like monocytes showing diffusible proliferation and osteoclast-like multinucleated giant cells are intermingled in tumors showing clear borders. The cause of giant cell tumor of tendon sheath (GCTT) is unknown, and the origin of tumor cells is also unknown.

Giant cell tumor of tendon sheath (GCTT) is classified as benign tumor, and it seldom follows fatal process. However, it strongly tends to proliferate and spread over surroundings, and it recurs in 20 to 30% of the cases even if extirpation operations are conducted. Since giant cell tumor of tendon sheath (GCTT) strongly adheres to tendon sheath, it is hard to excise it, and if an extirpation operation is conducted, adhesion of extensor tendon or flexor tendon, and injury to nerves or blood vessels are easily caused. Moreover, advance of giant cell tumor of tendon sheath (GCTT) destroys bones, joints, and ligaments. Therefore, there is desired a therapeutic treatment of giant cell tumor of tendon sheath (GCTT) that is not based on surgical operation, but is based on an internal medical therapeutic treatment, and does not invite recurrence and metastasis to lung. There is also desired a therapeutic agent for giant cell tumor of tendon sheath (GCTT) that can be orally administered, and can suppress tumor proliferation.

Pigmented villonodular synovitis (PVNS) is a benign tumor that occurs in relatively young adults not older than 40, and slightly more frequently occurs in women. As for occurring position of PVNS, it most frequently occurs in the knee joint, and also frequently occurs in the large joints such as hip, leg, elbow, and shoulder joints, and surroundings thereof. PVNS is a disease that shows abnormal proliferation of tissues of the synovial membrane covering the inside of joints, forms tumors, and repeatedly causes hemorrhage. It is classified as that of "diffuse type" in which tumors are densely formed like piles of carpet on the whole surface, and "limited type (nodule type)" in which tumors are serially formed in a row, and the both types may simultaneously seen in not a few cases.

The subjective symptoms thereof include swelling and dull pain of joints, sticking sense of joints, disability for bending and extending joints beyond a certain extent, hot sensation at the knee, and the like, and blood often accumulates in joints.

PVNS is defined to be the same as the diffuse type giant cell tumor according to the WHO classification, and classified as a benign soft tissue tumor. In fact, tumors of PVNS themselves do not metastasize to other organs, and grow slowly, and therefore it is not a fatal disease. However, if PVNS is neglected, destruction and deformation of bones advance to cause gonarthrosis and greatly spoil the quality of life of patients, and therefore it is a disease for which an early treatment is required. Moreover, since PVNS infiltrates in a diffusive manner, complete excision thereof is difficult, and it recurs in about 50% of patients. As for histological characteristics, it shows diffusive proliferation of synovial cell-like monocytes, and there are intermingled osteoclast-like multinucleated giant cells, foam cells, siderophores, inflammatory cells, and the like. The cell origin of PVNS is unknown.

There is only ablative operation as the therapeutic treatment of PVNS. In ablative operation of PVNS, grown synovial membrane should be excised under observation with an endoscope or after incision of joint. However, even if the surgical operation is conducted so that neither the joint capsules nor the ligamentum tissues should be injured, if it infiltrates to a bone, it should also be eliminated by curettage, and depending on degree of infiltration to a bone, use of an artificial joint or amputation of leg or arm may be required.

Therefore, there is desired a therapeutic treatment that is not based on surgical operation, but is based on an internal medical therapeutic treatment. There is also desired a therapeutic agent for PVNS that can be orally administered, and can suppress tumor proliferation.

As described above, for all of giant cell tumor of bone, giant cell tumor of tendon sheath, and PVNS, any effective therapies have not been developed at present, except for surgical operation.

Chondrosarcoma accounts for about 20% of primary malignant bone tumors, and is a malignant tumor showing the secondly highest occurrence frequency following that of bone sarcoma. It occurs in persons of such a broad age range as twenties to sixties, and it is comparatively frequently observed in, in particular, persons of middle or advanced age of 40 years old or older, and such cases account for almost half of the total cases. As for the patient's man-to-woman ratio, chondrosarcoma occurs about twice frequently in men compared with women.

As for onset position of chondrosarcoma, it frequently occurs in the thighbone (namely, the bone of thigh above knee), humerus (namely, the bone extending from elbow to shoulder), pelvis, rib, scapula, and flat bone, and the cases occurring in these positions account for 70 to 80% of the total cases.

As for the subjective symptoms of chondrosarcoma, patients frequently notice the disease from swelling of affected part or dyskinesia, patients may also notice the disease from hard tumor giving weak pain, and pain caused by bone fracture. Histological images of chondrosarcoma show abundant glasslike cartilage matrices or mucous matrices, and they proliferate in a lobulating shape. Histological images of chondrosarcoma generally present (1) abundant cell components, (2) hypertrophy of nuclei, (3) appearance of hypertrophied binucleated cells, (4) appearance of chromatin-abundant multinucleated giant cartilage cells, and the like. Although the borders of tumors of chondrosarcoma are comparatively clear, there is observed infiltration thereof between bone trabeculae (namely, finely loosen part of the spongin tissues at the epiphysis of a long tubular bone), or in the Havers canal (namely, passage of blood vessels locating at the center of bone lamella system of the compact bone in the diaphysis of a long tubular bone). The cause and cell origin of chondrosarcoma are unknown.

As the radical therapy of chondrosarcoma, there is only ablative operation. Against chondrosarcoma, effect of radiotherapy or anticancer drug treatment is not sufficient. Since chondrosarcoma is a malignant tumor, extensive excision is performed so as to excise the tumor and surrounding tissues together with covering normal tissues. Therefore, the surgical operation involves a risk of spoiling motor functions, and amputation of diseased limb is sometimes unavoidable. Although the five-year survival rate of chondrosarcoma is 70 to 80%, there are not a few cases where a long-term process of ten years or longer including repetitive recurrences results in death.

Therefore, there is desired a therapeutic treatment of chondrosarcoma that is not based on surgical operation, but is based on an internal medical therapeutic treatment. There is also desired a therapeutic agent for chondrosarcoma that can be orally administered, and can suppress the tumor proliferation.

Bone sarcoma is a malignant tumor that primarily develops in a bone tissue, and is a malignant tumor that directly produces osteoid (constituent element of bone tissues consisting of matrix and fibers), or bone. Bone sarcoma is the most frequently occurring tumor among the malignant tumors that primarily develop in a bone, and it occurs in 1 to 2 persons out of one million persons, and occurs in about 200 persons every year in Japan. Bone sarcoma patients in their teens account for 60%, and those in their twenties account for 15% of the total bone sarcoma patients. As for the patients' man-to-woman ratio, it slightly more frequently occurs in men compared with women. Bone sarcoma cases account for about 33% of the total cases of malignant tumors that primarily develop in bones.

Bone sarcoma frequently occurs in a long tubular bone, and the most frequently occurring positions are, from the highest frequency, the knee (distal position of the thighbone (namely, position above the knee) and proximal position of the tibia (namely, position below the knee), of which cases account for 60%, hip joint, of which cases account for 15%, shoulder joint, of which cases account for 10%, and jaw, of which cases account for 6%, and these frequencies are similar to the occurrence frequencies of the giant cell tumor of bone for such positions. As a subjective symptom of bone sarcoma, continuous pain arises, and such pain occurs in connection with sporting activities. Therefore, it may be mistaken for muscular pain, and thus cautions are required.

Although the five-year survival rate of bone sarcoma depends on medical facilities, there is a report that it was about 70% for the cases without metastasis. Bone sarcoma frequently metastasizes to the lung, like giant cell tumor of bone. Prognosis of the cases for which metastasis is found at the time of the first medical examination is bad, and the five-year survival rate for such cases is about 20% even in advanced facilities.

In the histopathological sense, bone sarcoma is a low differentiation spindle-shaped multinucleated sarcoma. However, histological images thereof show a wide variety of aspects, including from those apparently seen only as reactive osteogenesis or fibrosis to those showing consolidation with marked bone and osteoid formation, those showing marked chondrogenesis, as well as those showing characteristics of utterly undifferentiated sarcoma hardly accompanied by osteoid, and thus considerably change, and it always appears in different ways depending on positions even in the same tumor. Appearance of multinucleated giant cells almost always observed, and they show various appearances both in amount and quality, including those of osteoclast-like gentle type to those of strange appearance apparently seen to be malignant, and may sometimes show giant cell tumor of bone-like images.

As therapies of bone sarcoma, chemotherapeutic treatment and surgical operation are mainly conducted. The chemotherapeutic treatment for bone sarcoma is characterized in that the chemotherapeutic treatment is performed in advance of surgical operation, unlike those for the other types of cancers. Already existing invisible micrometastases (lung, liver, bone, and the like) can be thereby eradicated or suppressed, and an effective anticancer agent can also be thereby determined. Therefore, it enables selection of anticancer agent to be used in postoperative chemotherapeutic treatment (performed after surgical operation), or chemotherapeutic treatment to be performed at the time of recurrence. At present, cisplatin, adriamycin, ifosfamide, cyclophosphamide, ethoposide, methotrexate, doxorubicin, bleomycin, and caffeine are frequently used in an appropriate combination thereof. For example, in the caffeine-combined therapy, cisplatin, adriamycin, and caffeine are used in combination. Most of these anticancer agents should be administered by drip infusion.

The most important in topical treatment of bone sarcoma is to surely excise the primary lesion. However, considering the frequent occurrence in young persons, preservation of motor functions is also important. The number of cases not requiring amputation of leg or arm, and allowing preservation of the diseased limb is increasing in recent years. However, if an artificial joint must be used, lifetime of artificial joint is about 20 years, and therefore there arises a problem that, even if the disease is completely cured, a resurgical operation is required for replacing the artificial joint.

Therefore, there is desired a therapeutic agent for bone sarcoma that can be orally administered, and can suppress proliferation of bone sarcoma cells. There is also desired a therapeutic agent for bone sarcoma that can suppress metastasis of bone sarcoma cells to the lung.

As described above, giant cell tumor of bone (GCTB), giant cell tumor of tendon sheath (GCTT), pigmented villonodular synovitis (PVNS), chondrosarcoma, and bone sarcoma are tumors that occur in bone soft tissues, and they are commonly characterized in that there are no radical therapy other than ablative operation, and even if ablative operation is conducted, repetitive recurrence continuously degrades the quality of life of patients. However, the causes and original cells thereof are unknown. Although histologically osteoclast-like multinucleated giant cells are commonly observed in giant cell tumor of bone (GCTB), giant cell tumor of tendon sheath (GCTT), PVNS, and bone sarcoma, it is estimated that the body of the tumor is not the osteoclast-like multinucleated giant cells, and therefore there are of course not known any therapeutic treatment based on a mechanism commonly applicable to giant cell tumor of bone (GCTB), giant cell tumor of tendon sheath (GCTT), pigmented villonodular synovitis (PVNS), and chondrosarcoma, and any attempts for developing medicaments for such therapeutic treatment.

As report concerning therapeutic agent for giant cell tumor occurring in bones and soft tissues known so far, there is only a report that mizoribine, which is an immunosuppressant based on inhibitory action against the biosynthesis system of purine of nucleic acids, slightly inhibited proliferation of PVNS in vitro (Patent document 1), except for the reports of the inventors of the present invention themselves. The reports of the inventors of the present invention, to which the provisions of the exception to loss of novelty or grace period shall be applied, are not mentioned in this section as prior art references.

The peroxisome proliferator-activated receptor γ (PPARγ) is a transcriptional factor protein belonging to the intranuclear receptor superfamily, which exists in fat cells, macrophages, and the like. PPARγ exists as a hetero-complex formed together with the retinoid X receptor (RXR) protein.

It is considered that, in the absence of a PPARγ agonist, the hetero-complex of PPARγ and RXR binds with a corepressor protein complex, and binds to the PPAR response element (PPRE) existing in a promoter region of a lipid metabolism-related gene in a genome gene to suppress transcription of mRNAs of the genes existing downstream thereof, including apoptosis-related genes, various lipid metabolism-related genes or fat cell differentiation-related genes such as those for lipoprotein lipase (LPL) and fatty acid transport protein (FATP), arteriosclerosis-related genes, and anti-inflammation-related genes. It is also considered that, however, if a PPARγ agonist binds to PPARγ, a co-activator protein complex binds to the hetero-complex of PPARγ and RXR in place of release of the co-repressor protein complex from the hetero-complex of PPARγ and RXR to promote transcription of mRNAs of the genes existing downstream from the PPAR response element (PPRE), including the apoptosis-related genes, various lipid metabolism-related genes or fat cell differentiation-related genes such as those for lipoprotein lipase (LPL) and fatty acid transport protein (FATP), arteriosclerosis-related genes, and anti-inflammation-related genes.

As PPARγ agonists, there are known angiotensin II receptor antagonists such as irbesartan and telmisartan, thiazolidinedione derivatives, non-steroidal anti-inflammatory agents, and endogenous ligands such as 15-deoxy-Δ12,14-prostaglandin J2 (15d-PGJ2), 15-hydroxyeicosatetraenoic acid (15-HETE), 9-hydroxyoctadecadienoic acid (9-HODE), 13-hydroxyoctadecadienoic acid (15-HODE), nitrolinoleic acid, oxidized LDL, long chain fatty acids, eicosanoids, and lysophospholipids. Long chain fatty acid refers to an aliphatic acid containing 11 or more carbon atoms in the molecule.

The angiotensin II receptor antagonists are agents for lowering blood pressure by inhibiting binding of angiotensin II, which is a pressor substance, with the receptor thereof. Irbesartan and telmisartan are angiotensin II receptor antagonists currently used on clinical sites, and they are known to have a partial agonistic activity for PPARγ (partial agonist), in addition to the angiotensin II receptor antagonist activity.

There is not known any prior art reference describing that an angiotensin II receptor antagonist can be used for prophylactic or therapeutic treatment, or prevention of metastasis of giant cell tumor occurring in bones and soft tissues, chondrosarcoma, or bone sarcoma.

The thiazolidinedione derivatives are known as therapeutic agents for type II diabetes mellitus, and pioglitazone and rosiglitazone are clinically used. The thiazolidinedione derivatives exhibit activities for improving insulin resistance, suppressing saccharide production in the liver, promoting saccharide incorporation in peripheral cells, combusting fatty acids, promoting sensitivity of insulin receptor, suppressing arteriosclerosis, anti-inflammation, suppressing myocardial hypertrophy, and the like by eliminating hypertrophied fat cells that secrete TNFα, resistin, MCP-1, PAI-1, and the like by apoptosis, or deriving them to differentiate into small fat cells that secrete adiponectin into blood.

As the thiazolidinedione derivatives, there are known pioglitazone, rosiglitazone, troglitazone, isaglitazone, netoglitazone, rivoglitazone, balaglitazone, lobeglitazone, englitazone, ciglitazone, and the like. However, since they may cause critical adverse drug reaction, those clinically used at present as therapeutic agent for type II diabetes mellitus are only pioglitazone and rosiglitazone.

In addition to the activity as a therapeutic agent for type II diabetes mellitus, the thiazolidinedione derivatives such as pioglitazone are known on a laboratory level to inhibit proliferations of colon cancer (Non-patent documents 1 and 2), gastric cancer (Non-patent documents 3 and 4), non-small cell type lung cancer cells (Non-patent document 5), chondrosarcoma (Non-patent document 6), and malignant melanoma (Non-patent document 7). It is also known that thymoquinone having anticancer activity increases the PPARγ activity in breast cancer cells (Non-patent document 8).

Besides the above, Japanese Patent Unexamined Publication (Kokai) No. 2005-200419 (Patent document 2) describes, in the claims, a method for therapeutic treatment of cancer using a mevalonate pathway inhibitor and a PPARγ agonist in combination, but it does not mention any example at all. Therefore, it is an unverified invention, and does not have any meaning as a prior art. Similarly, Japanese Patent Unexamined Publication (Kohyo) No. 2009-533467 (Patent document 3) describes, in claims 9, and 14 to 17, uses of compounds having the thiazolidinedione structure represented by a general formula for therapeutic treatment of carcinoma, sarcoma, and giant cell tumor of bone. However, like Patent document 2, it does not mention any example indicating the pharmacological activity at all.

As described above, there are not known any prior art references describing that thiazolidinedione derivatives can be used for prophylactic and therapeutic treatments, or prevention of metastasis of giant cell tumor occurring in bones and soft tissues with scientific evidences, except for the reports of the inventors of the present invention themselves.

The non-steroidal anti-inflammatory agents are non-steroidal agents having anti-inflammatory activity, analgesic action, and antipyretic action, of which typical example is aspirin (namely, acetylsalicylic acid), and they are known as relatively safe drugs. It is known that, as for the action mechanism of the non-steroidal anti-inflammatory agents, they provides the anti-inflammatory activity, analgesic action, and antipyretic action through inhibitory activity against cyclooxygenase 1 and/or cyclooxygenase 2.

As the non-steroidal anti-inflammatory agents, there are known zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, nahumetone, ketoprofen, acetylsalicylic acid, ibuprofen, pranoprofen, sulindac, and the like, and various kinds of drugs are widely used on clinical sites as drugs for ameliorating such symptoms as headache, toothache, menstrual pain, and pyrexia.

Proglumetacin and maleate thereof are prodrugs that are metabolized into indomethacin in the body and exhibit the efficacy. Similarly, indometacin farnesil is a prodrug that is metabolized into indomethacin in the body and exhibits the efficacy. Similarly, ampiroxicam is a prodrug that is metabolized into piroxicam in the body and exhibits the efficacy.

As for use of non-steroidal anti-inflammatory agents for oncotherapy, Japanese Patent Unexamined Publication (Kokai) No. 2005-343802 (Patent document 4) describes in the examples that when ketoprofen was transdermally administered to nude mice transplanted with the OST cells, which are human bone sarcoma-derived cultured cells, the tumor weight decreased to 48% of that observed in a placebo group after four weeks. Further, Japanese Patent Unexamined Publication (Kohyo) No. 2006-501136 (Patent document 5) describes methods for therapeutic treatments of pain, inflammation, cancer, Alzheimer's disease, and cardiovascular disease using a PPARγ agonist or selective inhibitor for cyclooxygenase 2 in the claims thereof. However, it does not describe at all any results of examples demonstrating the pharmacological actions.

As for prior art describing relation between PPARγ agonist and non-steroidal anti-inflammatory agent, it was reported that diclofenac or celecoxib prevented occurrence of colon cancer induced by repetitive administration of 1,2-dimethylhydrazine dihydrochloride to rats, and at the same time, these agents reduced amount of NF-κB protein in the large intestine, and increased amount of the PPARγ protein (Non-patent document 9).

As for action on synovial cells derived from rheumatism patients, it was reported that troglitazone, indomethacin, diclofenac, oxaprozin, and zaltoprofen activated PPARγ, and caused apoptosis to suppress proliferation of the cells, but NS-398, which is a selective cyclooxygenase 2 inhibitor, did not activate PPARγ and did not cause apoptosis, although it suppressed proliferation of the cells, and ketoprofen and acetaminophen did not cause activation of PPARγ, apoptosis, and suppression of the proliferation (Non-patent document 10).

Furthermore, it was reported by the inventors of the present invention that when zaltoprofen was allowed to act on giant cell tumor of bone (GCTB) derived from a patient, it suppressed proliferation of the cells of the giant cell tumor of bone, promoted expression of PPARγ in the cells of giant cell tumor of bone, and induced differentiation of the cells into fat cells (Non-patent documents 11 and 12).

Similarly, it was reported by the inventors of the present invention that when zaltoprofen or troglitazone was allowed to act on giant cell tumor of bone (GCTB) derived from a patient, these drugs suppressed proliferation of the cells of the giant cell tumor of bone, and promoted expression of PPARγ in the cells of giant cell tumor of bone, and zaltoprofen induced differentiation of the cells into fat cells (Non-patent documents 13, 14, 15, and 16).

It was also reported by the inventors of the present invention that in a patient who had taken zaltoprofen for four weeks at a dose of 240 mg per of day, which is the standard dose mentioned in the package insert, giant cell tumor of bone disappeared, but instead, fat cell-like cells showing enhanced expression of PPARγ were observed (Non-patent documents 13 and 17).

Similarly, it was also reported by the inventors of the present invention that zaltoprofen, pioglitazone, and troglitazone induced apoptosis in the cells of H-EMC-SS, which is a chondrosarcoma cell line, to suppress proliferation thereof, and promoted expression of PPARγ (Non-patent documents 18 and 19).

Non-patent documents 11 to 19 mentioned above, which are reports of the inventors of the present invention themselves, do not constitute prior arts of the present invention, since provisions of the exception to loss of novelty or grace period shall be applied to them.

As described above, except for the reports of the inventors of the present invention themselves, there are not known any prior art references describing that non-steroidal anti-inflammatory agents can be used for prophylactic treatment, therapeutic treatment, or prevention of metastasis of giant cell tumor occurring in bones and soft tissues, chondrosarcoma, or bone sarcoma.

Moreover, since it is not considered that there is any radical therapy for giant cell tumor occurring in bones and soft tissues except for ablative operation, and it is considered that the first priority of the treatment of chondrosarcoma or bone sarcoma is given to raising survival rate by extensive excision, an object of improving ability to carry out everyday activities of patients suffering from giant cell tumor occurring in bones and soft tissues, chondrosarcoma, or bone sarcoma is not recognized.

PRIOR ART REFERENCES

Patent Documents

Patent document 1: WO2008/026729
Patent document 2: Japanese Patent Unexamined Publication (Kokai) No. 2005-200419
Patent document 3: Japanese Patent Unexamined Publication (Kohyo) No. 2009-533467
Patent document 4: Japanese Patent Unexamined Publication (Kokai) No. 2005-343802
Patent document 5: Japanese Patent Unexamined Publication (Kohyo) No. 2006-501136

Non-Patent Documents

Non-patent document 1: Jpn. J. Cancer Res., 1999; 90:75-80
Non-patent document 2: Cancer Lett., 2010; 297:65-74
Non-patent document 3: FEBS Lett., 1999; 455:135-139
Non-patent document 4: Zhongguo yishi zazhi 2010; 12(6): 743-747
Non-patent document 5: Mol. Pharmacol., 2007; 72674-685
Non-patent document 6: British Journal of Cancer, 2002; 86:1303-1309
Non-patent document 7: Medical Oncology, 2006; 23(3): 393-402
Non-patent document 8: Biochem. Pharmacol., 2011; 82:464-475
Non-patent document 9: Tumor Biology, 2010; 31:427-436

Non-patent document 10: J. Pharmacol. Exp. Ther., 2002; 3021.8-25
Non-patent document 11: The Journal of the Japanese Orthopedic Association, 2012; 86(8):S1319:2-9-18
Non-patent document 12: The Journal of the Japanese Orthopedic Association, 2013; 87(8):1-8-22
Non-patent document 13: 2013 AAOS (American Association of Orthopedic Surgeons) Annual Meeting Abstract Paper 341
Non-patent document 14: 26th Eur. Musculoskeletal Oncology Society Meeting 2013, Abstract P4:103
Non-patent document 15: The Journal of the Japanese Orthopedic Association, 2013; 87(6):1-2-FP3-8
Non-patent document 16: ISOLS 2013 Abstract N° 205 (Annual Meeting of International Society of Limb Salvage 2013, Abstract N° 310)
Non-patent document 17: Anticancer Research, 2013; 33:2169-2174
Non-patent document 18: The Journal of the Japanese Orthopedic Association, 2013; 87(8):1-8-20
Non-patent document 19: ISOLS 2013 Abstract N° 205 (Annual Meeting of International Society of Limb Salvage 2013, Abstract N° 205)

SUMMARY OF THE INVENTION

Object to be Achieved by the Invention

An object of the present invention is to provide a method for prophylactic treatment, therapeutic treatment, or prevention of metastasis of giant cell tumor occurring in a bone and soft tissue, chondrosarcoma, or bone sarcoma, which is not based on surgical operation. Another object of the present invention is to provide an agent for prophylactic treatment, therapeutic treatment, or prevention of metastasis of giant cell tumor occurring in a bone and soft tissue, chondrosarcoma, or bone sarcoma, which can be orally administered, and can suppress proliferation of tumor, per se. A further object of the present invention is to provide an agent for prophylactic treatment, therapeutic treatment, or prevention of metastasis of giant cell tumor occurring in a bone and soft tissue, chondrosarcoma, or bone sarcoma, which can be orally administered, and can eliminate the tumor and/or induce the tumor to differentiate into fat cells.

A still further object of the present invention is to provide a medicament that can suppress recurrence and/or metastasis of giant cell tumor occurring in a bone and soft tissue, chondrosarcoma, or bone sarcoma. A still further object of the present invention is to provide a medicament that can recover motor functions of a patient of giant cell tumor occurring in a bone and soft tissue, chondrosarcoma, or bone sarcoma to improve quality of life of the patient.

A still further object of the present invention is to provide a local infusion for artery embolization and/or artificial bone that can cure giant cell tumor occurring in a bone and soft tissue, chondrosarcoma, or bone sarcoma, and can suppress recurrence and/or metastasis of them. A still further object of the present invention is to provide a method for screening for an agent for prophylactic treatment, therapeutic treatment, or prevention of metastasis of giant cell tumor occurring in a bone and soft tissue, chondrosarcoma, or bone sarcoma.

Means for Achieving the Object

The inventors of the present invention, who are orthopedic surgeons, incidentally encountered, at the time of ablative operation of giant cell tumor of bone (GCTB), which is the sole radical therapy of GCTB, a case where cells characteristic to bone giant cells did not exist in the excised bone tissues, but instead, fat cell-like cells existed in them. While it was hardly surprising to overlook the reason for the spontaneous recovery as a unique case, the inventors of the present invention carefully investigated the pathological and therapeutic history of the patient and heard symptoms and life conditions from the patient himself as faithfully adhering to the basics. During this process, the inventors of the present invention noted the fact that the patient had taken zaltoprofen over four weeks at a dose of 240 mg per day, which is the standard dose indicated in the package insert, in order to ameliorate pain of joints caused by giant cell tumor of bone, hit an idea that the fact had somehow related to the spontaneous recovery, and got a concept of the present invention that non-steroidal anti-inflammatory and sedative agents might suppress proliferation of giant cell tumor occurring in a bone and soft tissue, chondrosarcoma, or bone sarcoma, and induce it to differentiate into fat cells.

Then, the inventors of the present invention contacted various non-steroidal anti-inflammatory and sedative agents to cells excised from patients suffering from giant cell tumor occurring in a bone and soft tissue, chondrosarcoma, or bone sarcoma, and confirmed that the agents inhibited proliferation thereof, induced expression of PPARγ, and induced the tumor to differentiate into fat cell-like cells. They further confirmed that PPARγ agonists other than non-steroidal anti-inflammatory and sedative agents also inhibited proliferation of giant cell tumor of bone (GCTB), giant cell tumor of tendon sheath (GCTT), PVNS, and chondrosarcoma, and came to accomplish the present invention.

The present invention thus provides the followings.

[1] An agent for prophylactic treatment, therapeutic treatment, or prevention of metastasis of giant cell tumor occurring in a bone and soft tissue, chondrosarcoma, or bone sarcoma, which comprises a substance having a PPARγ-agonistic activity and/or a PPARγ expression-inducing activity as an active ingredient.

[2] The agent for prophylactic treatment, therapeutic treatment, or prevention of metastasis according to [1], wherein the substance having a PPARγ-agonistic activity and/or a PPARγ expression-inducing activity consists of one or more kinds of PPARγ agonists selected from the group consisting of a non-steroidal anti-inflammatory agent, a thiazolidinedione derivative, an angiotensin II receptor antagonist having a PPARγ-agonistic activity, and an endogenous PPARγ agonist.

[3] The agent for prophylactic treatment, therapeutic treatment, or prevention of metastasis according to [1] or [2], wherein the substance having a PPARγ-agonistic activity and/or a PPARγ expression-inducing activity consists of one or more kinds of non-steroidal anti-inflammatory agents selected from the group consisting of zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, nabumetone, ketoprofen, acetylsalicylic acid, ibuprofen, pranoprofen, and sulindac.

[4] The agent for prophylactic treatment, therapeutic treatment, or prevention of metastasis according to any one of [1] to [3], wherein the substance having a PPARγ-agonistic activity and/or a PPARγ expression-inducing activity consists of one or more kinds of thiazolidinedione derivatives selected from the group consisting of troglitazone, rosiglitazone, pioglitazone, balaglitazone, rivoglitazone, isaglitazone, netoglitazone, lobeglitazone, englitazone, and ciglitazone.

[5] The agent for prophylactic treatment, therapeutic treatment, or prevention of metastasis according to any one of [1] to [4], wherein the substance having a PPARγ-agonistic activity and/or a PPARγ expression-inducing activity consists of one or more kinds of angiotensin II receptor antagonists having a PPARγ agonistic activity selected from the group consisting of irbesartan and telmisartan.

[6] The agent for prophylactic treatment, therapeutic treatment, or prevention of metastasis according to any one of [1] to [5], wherein the substance having a PPARγ-agonistic activity and/or a PPARγ expression-inducing activity consists of one or more kinds of endogenous PPARγ agonists selected from the group consisting of 15-deoxy-Δ12,14-prostagladin J2, 15-hydroxyeicosatetraenoic acid, 9-hydroxyoctadecadienoic acid, 13-hydroxyoctadecadienoic acid, nitrolinoleic acid, and a long chain fatty acid.

[7] The agent for prophylactic treatment, therapeutic treatment, or prevention of metastasis according to any one of [1] to [6], wherein the giant cell tumor occurring in a bone and soft tissue is selected from the group consisting of giant cell tumor of bone, giant cell tumor of tendon sheath, and pigmented villonodular synovitis.

[8] The agent for prophylactic treatment, therapeutic treatment, or prevention of metastasis according to any one of [1] to [7], which further contains an anti-RANKL antibody.

[9] The agent for prophylactic treatment, therapeutic treatment, or prevention of metastasis according to [8], wherein the anti-RANKL antibody is denosumab.

[10] The agent for prophylactic treatment, therapeutic treatment, or prevention of metastasis according to any one of [1] to [9], which further contains a bisphosphonate.

[11] The agent for prophylactic treatment, therapeutic treatment, or prevention of metastasis according to [10], wherein the bisphosphonate consists of one or more kinds of bisphosphonates selected from the group consisting of etidronate, clodronate, tiludronate, pamidronate, neridronate, olpadronate, alendronate, ibandronate, tiludronate, incadronate, risedronate, minodronate, zoledronate, solvadronate, medronate, risendronate, amino-olpadronate, simadronate, pyridronate, rezidronate, EB1053, and YH 529.

[12] A local infusion for artery embolization or artificial bone, which comprises a substance having a PPARγ-agonistic activity and/or a PPARγ expression-inducing activity as an active ingredient.

[13] The local infusion for artery embolization or artificial bone according to [12], wherein the substance having a PPARγ-agonistic activity and/or a PPARγ expression-inducing activity consists of one or more kinds of PPARγ agonists selected from the group consisting of a non-steroidal anti-inflammatory agent, a thiazolidinedione derivative, an angiotensin II receptor antagonist having a PPARγ-agonistic activity, and an endogenous PPARγ agonist.

[14] The local infusion for artery embolization or artificial bone according to [12] or [13], wherein the substance having a PPARγ-agonistic activity and/or a PPARγ expression-inducing activity consists of one or more kinds of non-steroidal anti-inflammatory agents selected from the group consisting of zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, nabumetone, ketoprofen, acetylsalicylic acid, ibuprofen, pranoprofen, and sulindac.

[15] The local infusion for artery embolization or artificial bone according to any one of [12] to [14], wherein the substance having a PPARγ-agonistic activity and/or a PPARγ expression-inducing activity consists of one or more kinds of thiazolidinedione derivatives selected from the group consisting of troglitazone, rosiglitazone, pioglitazone, balaglitazone, rivoglitazone, isaglitazone, netoglitazone, lobeglitazone, englitazone, and ciglitazone.

[16] The local infusion for artery embolization or artificial bone according to any one of [12] to [15], wherein the substance having a PPARγ-agonistic activity and/or a PPARγ expression-inducing activity consists of one or more kinds of angiotensin II receptor antagonists having a PPARγ agonistic activity selected from the group consisting of irbesartan and telmisartan.

[17] The local infusion for artery embolization or artificial bone according to any one of [12] to [16], wherein the substance having a PPARγ-agonistic activity and/or a PPARγ expression-inducing activity consists of one or more kinds of endogenous PPARγ agonists selected from the group consisting of 15-deoxy-Δ12,14-prostagladin J2, 15-hydroxyeicosatetraenoic acid, 9-hydroxyoctadecadienoic acid, 13-hydroxyoctadecadienoic acid, nitrolinoleic acid, and a long chain fatty acid.

[18] The local infusion for artery embolization or artificial bone according to any one of [12] to [17], which further contains an anti-RANKL antibody.

[19] The local infusion for artery embolization or artificial bone according to [18], wherein the anti-RANKL antibody is denosumab.

[20] The local infusion for artery embolization or artificial bone according to any one of [12] to [19], which further contains a bisphosphonate.

[21] The local infusion for artery embolization or artificial bone according to [20], wherein the bisphosphonate consists of one or more kinds of bisphosphonates selected from the group consisting of etidronate, clodronate, tiludronate, pamidronate, neridronate, olpadronate, alendronate, ibandronate, tiludronate, incadronate, risedronate, minodronate, zoledronate, solvadronate, medronate, risendronate, amino-olpadronate, simadronate, pyridronate, rezidronate, EB1053, and YH 529.

[22] A substance having a PPARγ-agonistic activity and/or a PPARγ expression-inducing activity, or a combination thereof for use in prophylactic treatment, therapeutic treatment, or prevention of metastasis of giant cell tumor occurring in a bone and soft tissue, chondrosarcoma, or bone sarcoma.

[23] The substance having a PPARγ-agonistic activity and/or a PPARγ expression-inducing activity, or a combination thereof according to [22], which consists of one or more kinds of substances selected from the group consisting of a non-steroidal anti-inflammatory agent, a thiazolidinedione derivative, an angiotensin II receptor antagonist having a PPARγ-agonistic activity, and an endogenous PPARγ agonist.

[24] The substance having a PPARγ-agonistic activity and/or a PPARγ expression-inducing activity, or a combination thereof according to [22] or [23], wherein the substance having a PPARγ-agonistic activity and/or a PPARγ expression-inducing activity consists of one or more kinds of non-steroidal anti-inflammatory agents selected from the group consisting of zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, nabumetone, ketoprofen, acetylsalicylic acid, ibuprofen, pranoprofen, and sulindac.

[25] The substance having a PPARγ-agonistic activity and/or a PPARγ expression-inducing activity, or a combination thereof according to any one of [22] to [24], wherein the substance having a PPARγ-agonistic activity and/or a PPARγ expression-inducing activity consists of one or more kinds of thiazolidinedione derivatives selected from the group consisting of troglitazone, rosiglitazone, pioglitazone, balaglitazone, rivoglitazone, isaglitazone, netoglitazone, lobeglitazone, englitazone, and ciglitazone.

[26] The substance having a PPARγ-agonistic activity and/or a PPARγ expression-inducing activity, or a combination thereof according to any one of [22] to [25], wherein the substance having a PPARγ-agonistic activity and/or a PPARγ expression-inducing activity consists of one or more kinds of angiotensin II receptor antagonists having a PPARγ agonistic activity selected from the group consisting of irbesartan and telmisartan.

[27] The substance having a PPARγ-agonistic activity and/or a PPARγ expression-inducing activity, or a combination thereof according to any one of [22] to [26], wherein the substance having a PPARγ-agonistic activity and/or a PPARγ expression-inducing activity consists of one or more kinds of endogenous PPARγ agonists selected from the group consisting of 15-deoxy-Δ12,14-prostagladin J2, 15-hydroxyeicosatetraenoic acid, 9-hydroxyoctadecadienoic acid, 13-hydroxyoctadecadienoic acid, nitrolinoleic acid, and a long chain fatty acid.

[28] The substance having a PPARγ-agonistic activity and/or a PPARγ expression-inducing activity, or a combination thereof according to any one of [22] to [27], wherein the giant cell tumor occurring in a bone and soft tissue is selected from the group consisting of giant cell tumor of bone, giant cell tumor of tendon sheath, and pigmented villonodular synovitis.

[29] The substance having a PPARγ-agonistic activity and/or a PPARγ expression-inducing activity, or a combination thereof according to any one of [22] to [28], which further contains an anti-RANKL antibody.

[30] The substance having a PPARγ-agonistic activity and/or a PPARγ expression-inducing activity, or a combination thereof according to [29], wherein the anti-RANKL antibody is denosumab.

[31] The substance having a PPARγ-agonistic activity and/or a PPARγ expression-inducing activity, or a combination thereof according to any one of [22] to [30], which further contains a bisphosphonate.

[32] The substance having a PPARγ-agonistic activity and/or a PPARγ expression-inducing activity, or a combination thereof according to [31], wherein the bisphosphonate consists of one or more kinds of bisphosphonates selected from the group consisting of etidronate, clodronate, tiludronate, pamidronate, neridronate, olpadronate, alendronate, ibandronate, tiludronate, incadronate, risedronate, minodronate, zoledronate, solvadronate, medronate, risendronate, aminoolpadronate, simadronate, pyridronate, rezidronate, EB1053, and YH 529.

[33] A method for prophylactic treatment, therapeutic treatment, or prevention of metastasis of giant cell tumor occurring in a bone and soft tissue, chondrosarcoma, or bone sarcoma, which comprises administering an effective amount of a substance having a PPARγ-agonistic activity and/or a PPARγ expression-inducing activity to an object.

[34] The method for prophylactic treatment, therapeutic treatment, or prevention of metastasis of giant cell tumor occurring in a bone and soft tissue, chondrosarcoma, or bone sarcoma according to [33], wherein the substance having a PPARγ-agonistic activity and/or a PPARγ expression-inducing activity consists of one or more kinds of PPARγ agonists selected from the group consisting of a non-steroidal anti-inflammatory agent, a thiazolidinedione derivative, an angiotensin II receptor antagonist having a PPARγ-agonistic activity, and an endogenous PPARγ agonist.

[35] The method for prophylactic treatment, therapeutic treatment, or prevention of metastasis of giant cell tumor occurring in a bone and soft tissue, chondrosarcoma, or bone sarcoma according to [33] or [34], wherein the substance having a PPARγ-agonistic activity and/or a PPARγ expression-inducing activity consists of one or more kinds of non-steroidal anti-inflammatory agents selected from the group consisting of zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, nabumetone, ketoprofen, acetylsalicylic acid, ibuprofen, pranoprofen, and sulindac.

[36] The method for prophylactic treatment, therapeutic treatment, or prevention of metastasis of giant cell tumor occurring in a bone and soft tissue, chondrosarcoma, or bone sarcoma according to any one of [33] to [35], wherein the substance having a PPARγ-agonistic activity and/or a PPARγ expression-inducing activity consists of one or more kinds of thiazolidinedione derivatives selected from the group consisting of troglitazone, rosiglitazone, pioglitazone, balaglitazone, rivoglitazone, isaglitazone, netoglitazone, lobeglitazone, englitazone, and ciglitazone.

[37] The method for prophylactic treatment, therapeutic treatment, or prevention of metastasis of giant cell tumor occurring in a bone and soft tissue, chondrosarcoma, or bone sarcoma according to any one of [33] to [36], wherein the substance having a PPARγ-agonistic activity and/or a PPARγ expression-inducing activity consists of one or more kinds of angiotensin II receptor antagonists having a PPARγ agonistic activity selected from the group consisting of irbesartan and telmisartan.

[38] The method for prophylactic treatment, therapeutic treatment, or prevention of metastasis of giant cell tumor occurring in a bone and soft tissue, chondrosarcoma, or bone sarcoma according to any one of [33] to [37], wherein the substance having a PPARγ-agonistic activity and/or a PPARγ expression-inducing activity consists of one or more kinds of endogenous PPARγ agonists selected from the group consisting of 15-deoxy-Δ12,14-prostagladin J2, 15-hydroxyeicosatetraenoic acid, 9-hydroxyoctadecadienoic acid, 13-hydroxyoctadecadienoic acid, nitrolinoleic acid, and a long chain fatty acid.

[39] The method for prophylactic treatment, therapeutic treatment, or prevention of metastasis of giant cell tumor occurring in a bone and soft tissue, chondrosarcoma, or bone sarcoma according to any one of [33] to [38], wherein the giant cell tumor occurring in a bone and soft tissue is selected from the group consisting of giant cell tumor of bone, giant cell tumor of tendon sheath, and pigmented villonodular synovitis.

[40] The method for prophylactic treatment, therapeutic treatment, or prevention of metastasis of giant cell tumor occurring in a bone and soft tissue, chondrosarcoma, or bone sarcoma according to any one of [33] to [39], wherein the substance further contains an anti-RANKL antibody.

[41] The method for prophylactic treatment, therapeutic treatment, or prevention of metastasis of giant cell tumor occurring in a bone and soft tissue, chondrosarcoma, or bone sarcoma according to [40], wherein the anti-RANKL antibody is denosumab.

[42] The method for prophylactic treatment, therapeutic treatment, or prevention of metastasis of giant cell tumor occurring in a bone and soft tissue, chondrosarcoma, or bone sarcoma according to any one of [33] to [41], wherein the substance further contains a bisphosphonate.

[43] The method for prophylactic treatment, therapeutic treatment, or prevention of metastasis of giant cell tumor occurring in a bone and soft tissue, chondrosarcoma, or bone sarcoma according to [42], wherein the bisphosphonate consists of one or more kinds of bisphosphonates selected from the group consisting of etidronate, clodronate, tiludronate, pamidronate, neridronate, olpadronate, alendronate, ibandronate, tiludronate, incadronate, risedronate, minodronate, zoledronate, solvadronate, medronate, risendronate, amino-olpadronate, simadronate, pyridronate, rezidronate, EB1053, and YH 529.

[44] A method for screening for an agent for prophylactic treatment, therapeutic treatment, or prevention of metastasis of giant cell tumor occurring in a bone and soft tissue, chondrosarcoma, or bone sarcoma, which comprises the following steps:
(1) the step of culturing a cell or tissue derived from giant cell tumor occurring in a bone and soft tissue, chondrosarcoma, or bone sarcoma in the presence or absence of a test substance,
(2) the step of measuring one or more kinds of indices selected from the group consisting of those defined in (a) to (g) mentioned below in the presence or absence of the test substance;
(a) one or more indices selected from the group consisting of gene expression amount of PPARγ, and protein amount of PPARγ,
(b) one or more indices selected from the group consisting of gene expression amount of an apoptosis-related gene, protein amount of a translation product of an apoptosis-related gene, and biological activity of a translation product of an apoptosis-related gene,
(c) one or more indices selected from the group consisting of gene expression amount of a fat cell differentiation-related gene, protein amount of a translation product of a fat cell differentiation-related gene, and biological activity of a translation product of a fat cell differentiation-related gene,
(d) one or more indices selected from the group consisting of gene expression amount of an arteriosclerosis-related gene, protein amount of a translation product of an arteriosclerosis-related gene, and biological activity of a translation product of an arteriosclerosis-related gene,
(e) one or more indices selected from the group consisting of gene expression amount of an anti-inflammation-related gene, protein amount of a translation product of an anti-inflammation-related gene, and biological activity of a translation product of an anti-inflammation-related gene,
(f) an index consisting of a PPARγ-agonistic activity that can promote transcription of one or more kinds of genes selected from the group consisting of an apoptosis-related gene, a fat cell differentiation-related gene, an arteriosclerosis-related gene, and an anti-inflammation-related gene,
(g) amount of lipid contained in a fat cell or fat tissue, and
(3) the step of selecting a test substance that changes a value or values of the intracellular index or indices in the presence of a test substance compared with the value or values of the intracellular index or indices observed in the absence of the test substance.

[45] The screening method according to [44], wherein the giant cell tumor occurring in a bone and soft tissue is selected from the group consisting of giant cell tumor of bone, giant cell tumor of tendon sheath, and pigmented villonodular synovitis.

Effect of the Invention

With the agent for prophylactic treatment, therapeutic treatment, or prevention of metastasis of the present invention, giant cell tumor occurring in a bone and soft tissue, chondrosarcoma, or bone sarcoma can be treated without carrying out surgical operation. Where the agent for prophylactic treatment, therapeutic treatment, or prevention of metastasis of the present invention is used with ablative operation of giant cell tumor occurring in a bone and soft tissue, chondrosarcoma, or bone sarcoma, recurrence or metastasis of the tumor caused by tumor that could not be excised can be prevented. Furthermore, the agent for prophylactic treatment, therapeutic treatment, or prevention of metastasis of the present invention can be orally administered.

The agent for prophylactic treatment, therapeutic treatment, or prevention of metastasis and the local infusion for artery embolization or the artificial bone of the present invention are a radical therapeutic agent or radical therapeutic material that can cause apoptosis in giant cell tumor occurring in a bone and soft tissue, chondrosarcoma, or bone sarcoma to make the tumor disappear, and can induce differentiation of the tumor into fat cells to make the tumor disappear. The agent for prophylactic treatment, therapeutic treatment, or prevention of metastasis, and the local infusion for artery embolization, or the artificial bone of the present invention can suppress recurrence and metastasis of giant cell tumor occurring in a bone and soft tissue, chondrosarcoma, or bone sarcoma. The agent for prophylactic treatment, therapeutic treatment, or prevention of metastasis, and the local infusion for artery embolization, or the artificial bone of the present invention can restore motor functions of patients of giant cell tumor occurring in a bone and soft tissue, chondrosarcoma, or bone sarcoma, prevent nerve damages in the patients, and can dramatically improve quality of life of the patients.

Even if tumor cannot be disappeared with the agent for prophylactic treatment, therapeutic treatment, or prevention of metastasis, the local infusion for artery embolization, or the artificial bone of the present invention can improve or maintain the ability of patients to carry out everyday activities. Even if tumor cannot be disappeared with the agent for prophylactic treatment, therapeutic treatment, or prevention of metastasis, the local infusion for artery embolization, or the artificial bone of the present invention can promote restoration, formation, or hardening of bones to improve or maintain motor functions.

When the therapeutic agent or therapeutic material of the present invention contains a non-steroidal anti-inflammatory agent, it also has efficacies for ameliorating inflammation of affected part and reducing pain of the affected part.

The agent for prophylactic treatment, therapeutic treatment, or prevention of metastasis of the present invention can also be used as a chemotherapeutic agent to be used before or after a surgical operation.

Moreover, according to the present invention, by selecting a test substance that controls PPARγ and apoptosis or differentiation into fat cells, a novel agent for prophylactic treatment, therapeutic treatment, or prevention of metastasis of giant cell tumor occurring in a bone and soft tissue, chondrosarcoma, or bone sarcoma can be searched for.

BRIEF DESCRIPTION OF THE DRAWINGS

FIG. 79 A table summarizing cases of giant cell tumor of bone of patients who took zaltoprofen (Soleton Tablet (registered trademark)). There are shown age, sex, occurring part of giant cell tumor of bone, differentiation of incipience or recurrence, follow-up period, response rate, postoperative period, treatment/drug exposure period, presence or absence of postoperative recurrence, and comment for each case, as well as number of drawing showing photograph of affected part for the cases for which such a photograph is shown. The symbol "PR" in the column of response rate means "partial response", "SD" means "stable disease", and "PD" means "progressive disease". Zometa (registered trademark) mentioned in the column of comment is zoledronic acid hydrate Injection, and "Denosumab" is "anti-RANKL human monoclonal antibody (trade name, Ranmark)".

FIG. 80 A graph showing shrinking ratios of giant cell tumor of bone of giant cell tumor of bone patients who took zaltoprofen (Soleton Tablet (registered trademark)). The vertical axis represents shrinking ratio. A shrinking ratio of 70% means that the giant cell tumor of bone shrank to a size of 30% of the size observed before taking zaltoprofen, and a shrinking ratio of −20% means that the giant cell tumor of bone grew to a size of 120% of the size observed before taking zaltoprofen. The alphabets mentioned under the horizontal axis are alphabets for specifying the cases (see FIG. 79). In this specification, the shrinking ratio means a ratio of shrinkage of tumor observed after continuous administration of zaltoprofen, based on the size of the tumor observed before the administration of zaltoprofen. More specifically, in this specification, the shrinking ratio means a value obtained by subtracting 100 from a value calculated by dividing a length for one direction of tumor in the maximum cut surface thereof on an MRI image or X-ray CT image observed after continuous administration of zaltoprofen as the numerator with the corresponding length on such an image as mentioned above observed before continuous administration of zaltoprofen as the denominator, and represented in terms of percentage. For example, if a length of tumor for one direction in the maximum cut surface thereof of 50 mm observed before administration of zaltoprofen shrinks to 35 mm after the administration of zaltoprofen, the shrinking ratio is 30%.

FIG. 83 Photographs showing transversal X-ray CT images of affected part (lung metastasis part) of a giant cell tumor of bone patient (case e) who took zaltoprofen (Soleton Tablet (registered trademark)), which photographs were obtained before (Jan. 17, 2013) and after (Sep. 19, 2013) taking zaltoprofen. It can be seen that, as a result of taking zaltoprofen over about 35 weeks, the diameter of the giant cell tumor of bone that metastasized to the lung shrank from 8.2 mm to 7.9 mm.

FIG. 84 A table showing evaluation criteria of Karnofsky Performance Status (KPS). KPS is an evaluation method for classifying patient's conditions into ten stages of 100 to 0 according to the criteria shown in FIG. 84, and a higher score means better performance of the patient for everyday activities.

FIG. 85 A table summarizing effects of continuous taking of zaltoprofen (Soleton Tablet (registered trademark)) on giant cell tumor of bone. There are mentioned KPS determined before the start of taking zaltoprofen and after continuous taking of zaltoprofen, presence or absence of osteosclerosis determined by radiographic examination, presence or absence of osteosclerosis determined by CT, and shrinking ratio of giant cell tumor of bone for each case.

FIG. 86 A table summarizing cases of PVNS of patients who took zaltoprofen (Soleton Tablet (registered trademark)). There are shown age, sex, occurring part of PVNS, differentiation of incipience or recurrence, treatment period, drug exposure period, response rate, and comment for each case, as well as number of drawing showing photograph of affected part for the cases for which such a photograph is shown. The symbol "PR" in the column of response rate means "partial response", "SD" means "stable disease", and "PD" means "progressive disease".

MODES FOR CARRYING OUT THE INVENTION

Figure 1:
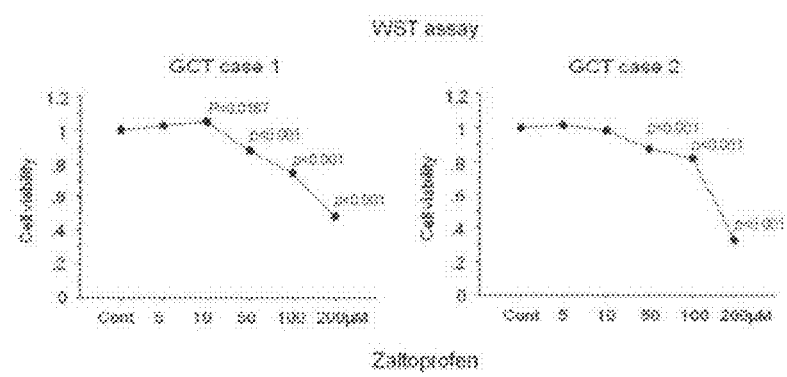
FIG. 1 Graphs showing results of suppression of proliferation of GCTB cultured cells that were cultured in a zaltoprofen-containing medium. The indications of GCT case 1 and GCT case 2 mean giant cell tumor of bone cultured cells from different origins. The indication of WST assay means that the cell proliferation was measured by using Cell Counting Kit-8 (CCK-8, Dojindo) using a tetrazolium salt WST-8 as a chromophoric substrate. The horizontal axes represent the concentration of zaltoprofen, and the vertical axes represent the live cell count measured on the basis of absorbance at 450 nm. The numerals on the right side of P< indicate the significance levels obtained as a result of statistical analysis.
Figure 2:
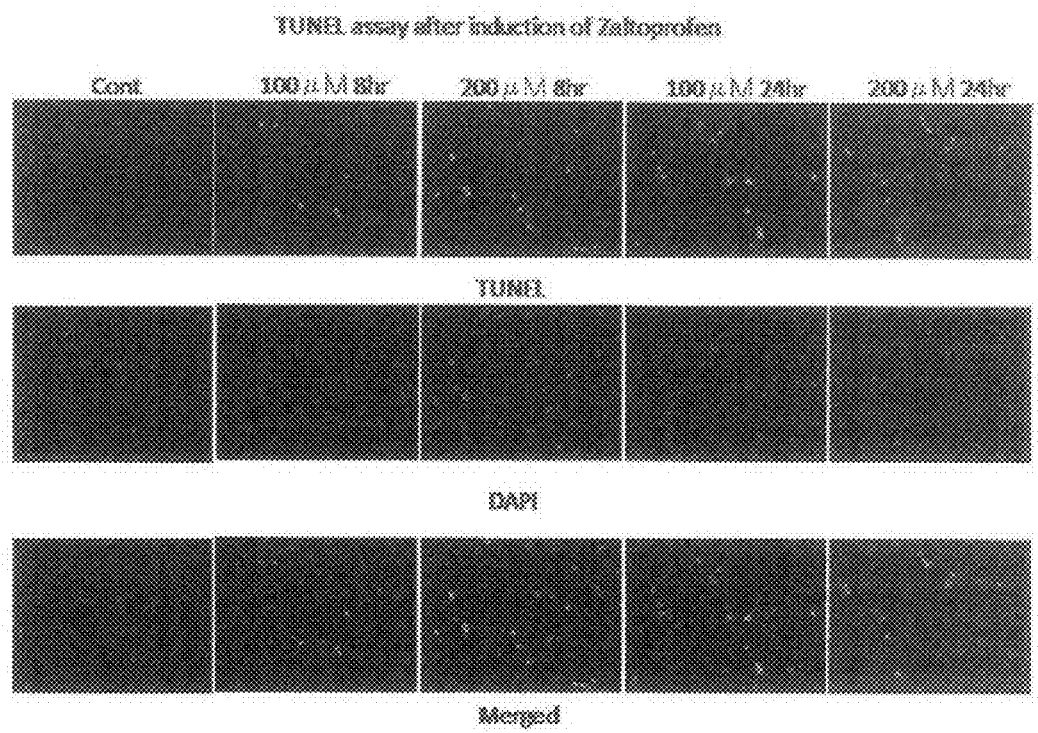
FIG. 2 Photographs showing results of Tunel assay performed with GCTB cultured cells that were cultured in a zaltoprofen-containing medium. In the Tunel assay, fragmented DNAs produced in the process of apoptosis were detected by the TdT-mediated dUTP nick end labeling method (TUNEL). The concentrations are the concentrations of zaltoprofen, and the times are the times of culture performed in the presence of zaltoprofen. The indication of DAPI means that the results are results of nuclear staining with DAPI, which is a fluorescent dye.
Figure 3:
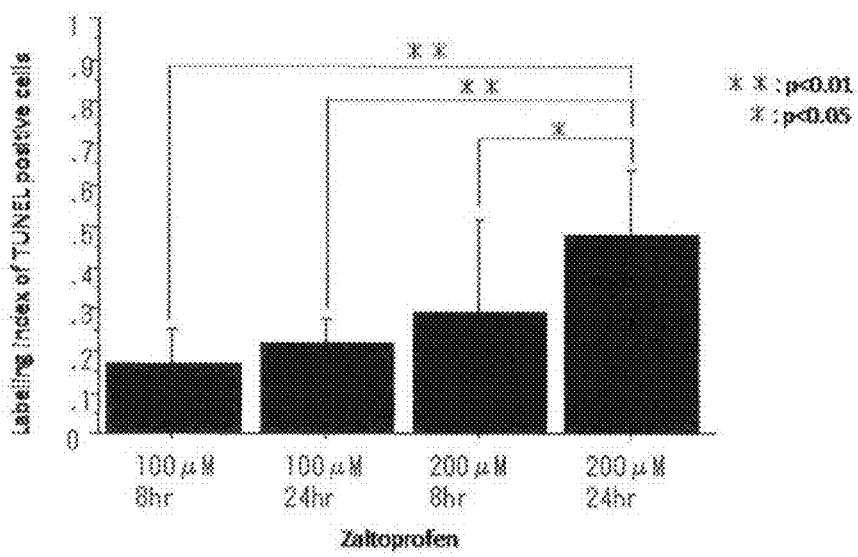
FIG. 3 A graph showing ratios of Tunel-positive cells in GCTB cultured cells that were cultured in a zaltoprofen-containing medium. The concentrations are the concentrations of zaltoprofen, and the times are the times of culture performed in the presence of zaltoprofen. The vertical axis represents the ratio of Tunel-positive cells. The numerals on the right side of P< indicate the significance levels obtained as a result of statistical analysis.
Figure 4:
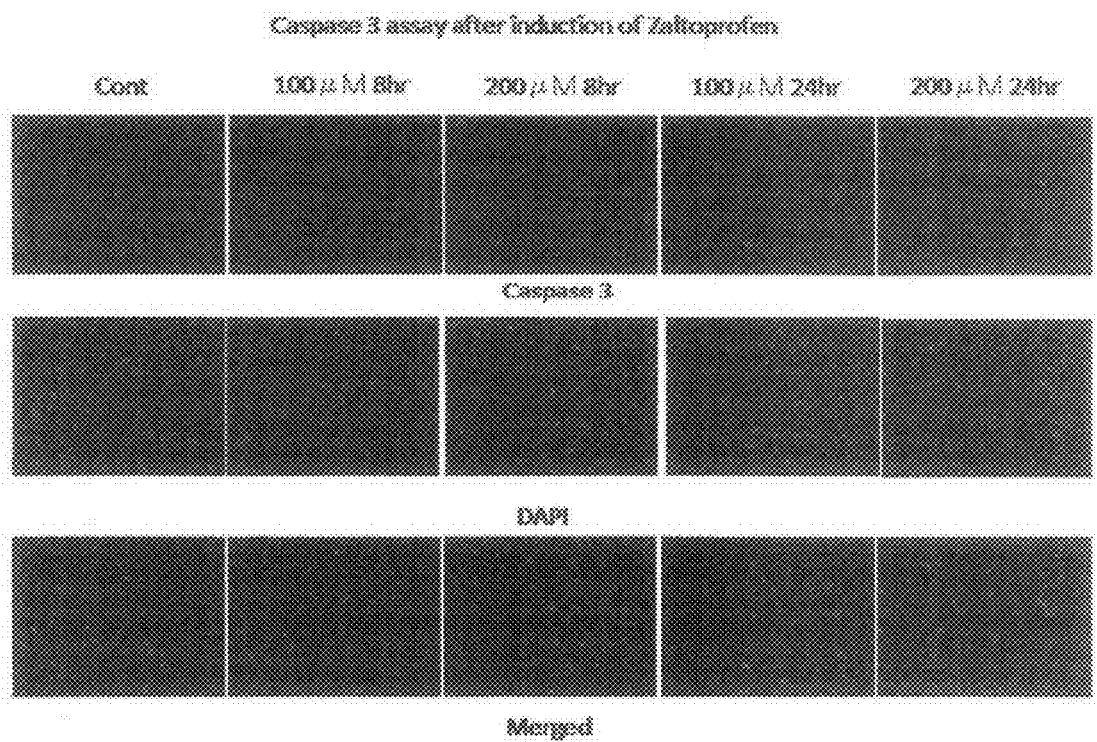
FIG. 4 Photographs showing results of caspase 3 staining of GCTB cultured cells that were cultured in a zaltoprofen-containing medium. The concentrations are the concentrations of zaltoprofen, and the times are the times of culture performed in the presence of zaltoprofen. The indication of DAPI means that the results are results of nuclear staining with DAPI, which is a fluorescent dye.
Figure 5:
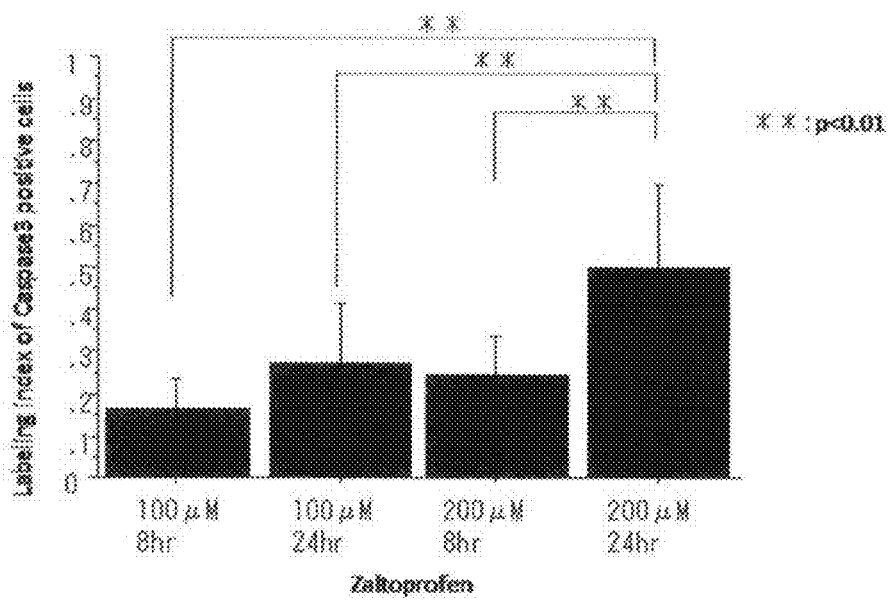
FIG. 5 A graph showing ratios of caspase 3-positive cells in GCTB cultured cells that were cultured in a zaltoprofen-containing medium. The concentrations are the concentrations of zaltoprofen, and the times are the times of culture performed in the presence of zaltoprofen. The vertical axis represents the ratio of caspase 3-positive cells. The numerals on the right side of P< indicate the significance levels obtained as a result of statistical analysis.

The present invention can be carried out by producing a drug containing a substance having a PPARγ-agonistic activity and/or a PPARγ expression-inducing activity as an active ingredient for the purpose of therapeutic treatment of a patient suffering from giant cell tumor occurring in a bone and soft tissue, chondrosarcoma, or bone sarcoma, prophylactic treatment for such a disease, or prevention of metastasis in such a patient as mentioned above.

The present invention can also be carried out by administering a drug containing a substance having a PPARγ-agonistic activity and/or a PPARγ expression-inducing activity as an active ingredient to a patient suffering from giant cell tumor occurring in a bone and soft tissue, chondrosarcoma, or bone sarcoma.

The object to which the present invention can be applied is not particularly limited, so long as a vertebrate is chosen as the object, and the object is preferably a mammal, more preferably human, ape, canine, feline, bovine, equine, swine, ovine, caprine, or lagomorph, most preferably human.

When the object to which the present invention can be applied is human, the present invention can be applied not only to a patient who has been clinically diagnosed to have giant cell tumor occurring in a bone and soft tissue, chondrosarcoma, or bone sarcoma, but also to a person who is suspected to have, or predicted to develop such a disease in future. The present invention can also be applied to a patient suffering from metastasis of cells of giant cell tumor occurring in a bone and soft tissue, chondrosarcoma, or bone sarcoma as a primary disease.

Embodiments of the agent for prophylactic treatment, therapeutic treatment, or prevention of metastasis of the present invention include those for use in restoration or formation of a bone in a patient suffering from giant cell tumor occurring in a bone and soft tissue, chondrosarcoma, or bone sarcoma. Embodiments of the agent for prophylactic treatment, therapeutic treatment, or prevention of metastasis of the present invention also include those for use in improving ability to carry out everyday activities of a patient suffering from giant cell tumor occurring in a bone and soft tissue, chondrosarcoma, or bone sarcoma.

The giant cell tumor occurring in a bone and soft tissue to which the present invention can be applied is not particularly limited, so far as giant cells developed in a bone and soft tissue are observed in the tumor. In particular, the present invention can be preferably applied to a tumor that generates giant cells in circumferences of bone, joint, or tendon sheath. The tumor in which giant cells developed in a bone and soft tissue are observed is preferably a benign tumor. Examples of such a tumor include, for example, giant cell tumor of bone (GCTB), giant cell tumor of tendon sheath (GCTT), pigmented villonodular synovitis (PVNS), and the like. Examples of benign giant cell tumor occurring in a bone and soft tissue also include chondroblastoma, nonossifying fibroma, osteoblastoma, aneurysmal bone cyst, and the like.

Examples of the chondrosarcoma to which the present invention can be applied include conventional chondrosarcoma, periosteal chondrosarcoma, mesenchymal chondrosarcoma, dedifferentiated chondrosarcoma, clear-cell chondrosarcoma, extraskeletal myxoid chondrosarcoma, and the like.

Examples of the bone sarcoma to which the present invention can be applied include those of osteoblast type called conventional type, chondroblast type, fibroblast type, vasodilatation type, small cellular type, parosteal bone sarcoma, and the like.

The present invention can also be applied to a tumor in which expression of PPARγ is observed. Examples of such a tumor in which expression of PPARγ is observed include breast cancer, colon cancer, lung cancer, thyroid gland cancer, esophageal cancer, gastric cancer, pancreatic cancer, liver cancer, kidney cancer, vesical cancer, ovarian cancer, uterine cervix carcinoma, prostate cancer, malignant melanoma, leukemia, malignant lymphoma, liposarcoma, leiomyosarcoma, bone sarcoma, and the like.

PPARγ is a transcriptional factor protein belonging to the intranuclear receptor superfamily, and a substance having a PPARγ-agonistic activity and/or a PPARγ expression-inducing activity can induce apoptosis or fat cell differentiation mediated by PPARγ in giant cell tumors occurring in a bone and soft tissue, chondrosarcoma, or bone sarcoma.

Therefore, in the present invention, as a substance that can be used as the agent for prophylactic treatment, therapeutic treatment, or prevention of metastasis of giant cell tumor occurring in bone and soft tissue, chondrosarcoma, or bone sarcoma, a substance having a PPARγ expression-inducing activity and/or a PPARγ-agonistic activity is desirable.

In the present invention, the PPARγ-agonistic activity means an activity for binding to PPARγ to promote transcription of a gene existing downstream from the PPAR response element (PPRE). Any substance having this activity can be regarded as a PPARγ agonist. Examples of gene existing downstream from the PPAR response element (PPRE) include an apoptosis-related gene, fat cell differentiation-related gene, arteriosclerosis-related gene, and anti-inflammation-related gene.

However, in the present invention, PPARγ agonist refers to a substance that can bind to PPARγ to promote transcription of a gene existing downstream from the PPAR response element (PPRE), or a substance selected from the group consisting of a non-steroidal anti-inflammatory agent, a thiazolidinedione derivative, an angiotensin II receptor antagonist having a PPARγ-agonistic activity, and an endogenous PPARγ agonist.

In the present invention, the PPARγ agonists exemplified below include pharmacologically acceptable salts, solvates, tautomers, and stereoisomers thereof in addition to the exemplified substances themselves, even if there are not explicitly indicated as "salt", "solvate", "tautomer", "stereoisomer", and the like In the present invention, substance having a PPARγ expression-inducing activity refers to a substance that can promote transcription of a PPARγ gene from a genome gene.

In the present invention, as a substance having a PPARγ expression-inducing activity, non-steroidal anti-inflammatory agents can be mentioned.

Non-steroidal anti-inflammatory agents have a PPARγ expression-inducing activity, and a PPARγ-agonistic activity.

In the present invention, the non-steroidal anti-inflammatory agent means a non-steroidal anti-inflammatory agent in a general meaning, and it is not particularly limited so long as it is a substance having anti-inflammatory activity, analgesic action, and antipyretic action based on inhibition of cyclooxygenase 1 and/or cyclooxygenase 2.

Examples of the non-steroidal anti-inflammatory agent include, for example, zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, nabumetone, ketoprofen, acetylsalicylic acid, ibuprofen, pranoprofen, and sulindac.

Among them, non-steroidal anti-inflammatory agents especially preferred for the present invention are zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, naproxen, loxoprofen, rofecoxib, ethenzamide, diflunisal, aluminoprofen, and nabumetone.

For the present invention, more preferred non-steroidal anti-inflammatory agents are zaltoprofen, diclofenac, indomethacin, proglumetacin, indometacin farnesil, celecoxib, etodolac, meloxicam, mofezolac, acemetacin, oxaprozin, acetaminophen, lornoxicam, ampiroxicam, piroxicam, and naproxen.

For the present invention, most preferred non-steroidal anti-inflammatory agents are zaltoprofen, diclofenac, indomethacin, proglumetacin, indometacin farnesil, celecoxib, etodolac, meloxicam, mofezolac, and acemetacin.

In the present invention, the thiazolidinedione derivative is not particularly limited so long as it is a substance having the thiazolidinedione structure and having a PPARγ-agonistic activity.

Examples of the thiazolidinedione derivative include pioglitazone, rosiglitazone, troglitazone, isaglitazone, netoglitazone, rivoglitazone, balaglitazone, lobeglitazone, englitazone, ciglitazone, and the like.

In the present invention, the angiotensin II receptor antagonist having a PPARγ-agonistic activity is not particularly limited so long as it is a substance having an angiotensin II receptor antagonistic activity and an activity as a PPARγ agonist. As the angiotensin II receptor antagonist having a PPARγ-agonistic activity, irbesartan and telmisartan are especially preferred.

In the present invention, the endogenous PPARγ agonist is not particularly limited so long as it is a substance endogenously possessed by an organism in the organism's own body, and is a substance having an activity as a PPARγ agonist. As the endogenous PPARγ agonist, 15-deoxy-Δ12, 14-prostagladin J2, 15-hydroxyeicosatetraenoic acid, 9-hydroxyoctadecadienoic acid, 13-hydroxyoctadecadienoic acid, nitrolinoleic acid, or a long chain fatty acid is preferred.

The response rate used as an index of effect of an anticancer agent is a ratio representing effectiveness of drug therapy such as those using anticancer agent. It means the total of the ratio of "complete response (CR)", which means complete disappearance of tumor, and the ratio of "partial response (PR)", which means 30% or more of shrinkage of tumor, determined according to the general standards (RECIST) using diagnostic imaging such as CT for an evaluation object. The "complete response (CR)" mentioned above means a state that tumor has completely disappeared, and the "partial response (PR)" means a state that the total of sizes of tumor has decreased by 30% or more. "Stable disease (SD)" means a state that size of tumor has not changed, and "progressive disease (PD)" means a state that the total of sizes of tumor has increased by 20% or more, and increased by 5 mm or more in terms of absolute value, or a state that new lesion has appeared. Although it is desirable for anticancer agents to provide complete response or partial response, if the ability to carry out everyday activities is maintained, the therapeutic effect can be regarded desirable, even if the disease is determined to be "stable disease" or "progressive disease".

In the present invention, the ability to carry out everyday activities can be determined according to, for example, the Karnofsky performance status (henceforth referred to as "KPS"). The score of KPS ranges from zero point to 100 points, and a higher score means better performance of the patient for everyday activities. KPS is used for judging prognosis of patient, measuring change of activity ability, determining whether patient can participate in a clinical trial, and the like. KPS is also useful as one of indices for determining quality of life.

The close of the agent for prophylactic treatment, therapeutic treatment, or prevention of metastasis of the present invention can be appropriately chosen depending on type of active ingredient, object of administration, age, body weight, sex, and conditions (general condition, pathological condition, presence or absence of complication, and the like) of the object of administration, administration period, dosage form, administration method, and the like. For example, the dose of zaltoprofen for oral administration to a human adult is preferably 80 to 1200 mg/day, more preferably 160 to 960 mg/day, further preferably 240 to 720 mg/day, most preferably 480 mg/day.

The agent for prophylactic treatment, therapeutic treatment, or prevention of metastasis of the present invention can be prepared by conventional methods for producing pharmaceutical preparations, for example, the production methods described in Japanese Pharmacopoeia 16th Edition, or similar methods, using, besides the active ingredient, carrier component, additives, and the like, as required.

The administration method of the agent for prophylactic treatment, therapeutic treatment, or prevention of metastasis of the present invention may be oral administration, or parenteral administration. Examples of the parenteral administration include, for example, intramuscular administration, enteral administration, transmucosal administration, transpulmonary administration, dermal administration, transnasal administration, vaginal administration, intraoral administration, epidural administration, intravenous administration, intrathecal administration, sublingual administration, rectum administration, instillation administration, intraarterial administration, intraurethral administration, subcutaneous administration, intracutaneous administration, and intraperitoneal administration. Examples of the dosage form for parenteral administration include injection (solution, lyophilized preparation, suspension, and the like), suppository (anus suppository, vaginal suppository, and the like), liquid for external use (infusion, poultice, aerosol, and the like), inhalant, patch, percutaneous absorption tape, cataplasm, skin external preparation, cream, gel, ointment (dermatologic paste, liniment, lotion, and the like), and the like. As the dosage form for oral administration, for example, gummi, syrup, jelly, chewable tablet, troche, dry syrup, buccal tablet, film-coated tablet, film preparation, pill, solution or suspension for oral administration, oral disintegrating tablet, hard capsule, subtilized granule, powder, sublingual tablet, uncoated tablet, enteric coated tablet, sugar-coated tablet, soft capsule, emulsion, adhesive tablet, powder, granule, and the like can be used.

In the preparation of the agent for prophylactic treatment, therapeutic treatment, or prevention of metastasis of the present invention, known additives can be used as required according to administration route, dosage form, and the like. As such additives, for example, lubricant, disintegrating aid, oxidation inhibitor or antioxidant, emulsifier, dispersing agent, suspending agent, dissolving agent, dissolving aid, thickener, pH adjustor or buffering agent, stabilizer, antiseptic or preservative, bacteriocide or antibacterial agent, antistatic agent, corrigent or masking agent, colorant, odor-masking agent or perfume, refrigerant, antifoam, isotonic agent, soothing agent, and the like can be used. These additives can be used independently or in a combination of two or more kinds of them.

For the agent for prophylactic treatment, therapeutic treatment, or prevention of metastasis of the present invention, a carrier or excipient chosen as required depending on administration route and use of preparation from the ingredients (for example, excipients, binders, disintegrating agents, lubricants, coating agents, and the like) described in, for example, besides Japanese Pharmacopoeia, (1) Handbook of Pharmaceutical Additives, Maruzen Co., Ltd., 1989, (2) "Encyclopedia of Pharmaceutical Additive 2007" (Yakuji Nippo, published on July, 2007), (3) Pharmaceutics, 5th revised edition, Nankodo Co., Ltd., 1997, (4) Japan Pharmaceutical Excipient Standards 2003 (Yakuji Nippo, August, 2003), and the like can be used.

As the carrier or excipient used for such pharmaceutical preparations, for example, saccharides or sugar alcohols such as lactose, glucose, sucrose, mannitol, sorbitol and xylitol, starches such as potato starch and corn starch, calcium carbonate, calcium phosphate, calcium sulfate, polysaccharides such as crystalline cellulose (including microcrystalline cellulose), silicon oxide or silicate such as light anhydrous silicic acid, glycyrrhizae radix pulverata, gentianae radix pulverata, and the like can be used.

As the binder used for the pharmaceutical preparations, for example, gelatin, soluble starches such as pregelatinized starch and partially pregelatinized starch, gum arabic, tragacanth gum, polysaccharides such as dextrin and sodium arginate; synthetic polymers such as polyvinylpyrrolidone (PVP), polyvinyl ether, polyvinyl alcohol (PVA), carboxyvinyl polymer, polyacrylic polymer, polylactic acid, and polyethylene glycol; cellulose ethers such as methylcellulose (MC), ethylcellulose (EC), carboxymethylcellulose (CMC), carboxymethylcellulose sodium, hydroxyethylcellulose (HEC), hydroxypropylcellulose (HPC), and hydroxypropylmethylcellulose (HPMC), and the like can be used.

As the disintegrating agent, sodium arginate, carboxymethyl starch sodium, carmellose, carmellose calcium, carmellose sodium, croscarmellose sodium, crospovidone, gelatin powder, starch, agar, crystalline cellulose, calcium carbonate, sodium hydrogencarbonate, low-substituted hydroxypropylcellulose, and the like can be used.

As the lubricant used for the pharmaceutical preparations, for example, magnesium stearate, talc, hydrogenated vegetable oil, Macrogoal, and the like can be used.

When an injection is prepared, it can be prepared with adding a pH adjuster, buffering agent, stabilizer, solubilizer, and the like as required.

When tablets or granules are prepared, as coating agent, for example, saccharides, hydroxypropylcellulose, sorbitol, purified shellac, gelatin, cellulose derivatives such as ethylcellulose, hydroxypropylmethylcellulose, and hydroxymethylcellulose, polyoxyethylene glycol, cellulose acetate phthalate, hydroxypropylmethylcellulose phthalate, methyl methacrylate/(meth)acrylate copolymer, Eudragit (methacrylic acid/acrylic acid copolymer), and the like can be used. The coating agent may be an enteric component such as cellulose phthalate, hydroxypropylmethylcellulose phthalate, and methyl methacrylate/(meth)acrylic acid copolymer, or gastric soluble component consisting of a polymer containing a basic component such as dialkylaminoalkyl (meth) acrylate (Eudragit and the like). The pharmaceutical preparation may also be a capsule of which capsule itself contains these enteric components and gastric soluble components.

The present invention can also be implemented by injecting or embedding a local infusion for artery embolization or artificial bone containing a substance having a PPARγ-agonistic activity and/or a PPARγ expression-inducing activity as an active ingredient into an artery of affected part at the time of surgical operation of a patient suffering from giant cell tumor occurring in a bone and soft tissue, chondrosarcoma, or bone sarcoma.

A substance having a PPARγ-agonistic activity and/or a PPARγ expression-inducing activity can be used in a state that it is contained in a local infusion for artery embolization or artificial bone. By injecting or embedding a local infusion for artery embolization or artificial bone containing a substance having a PPARγ-agonistic activity and/or a PPARγ expression-inducing activity as an active ingredient into an artery of affected part at the time of surgical operation of a patient suffering from giant cell tumor occurring in a bone and soft tissue, chondrosarcoma, or bone sarcoma, apoptosis can be induced in the giant cell tumor or chondrosarcoma to make the tumor disappear, or the tumor can be differentiated into fat cells, and thereby made to disappear. Furthermore, by using the local infusion for artery embolization or artificial bone containing a substance having a PPARγ-agonistic activity and/or a PPARγ expression-inducing activity as an active ingredient, recurrence and/or metastasis of giant cell tumor occurring in a bone and soft tissue, chondrosarcoma, or bone sarcoma can be prevented.

The artery embolization is a therapy for annihilating a tumor by injecting a substance that embolizes an artery upstream of giant cell tumor or chondrosarcoma so that nutrition and oxygen are not delivered to the giant cell tumor or chondrosarcoma.

Material of the local infusion for artery embolization is not particularly limited so long as a substance that can embolize arteries and adapts to living tissues is chosen, and various spherical particles including those of gelatin sponge and polyvinyl alcohol are clinically used.

Gelatin sponge consists of gelatin formed in a spongy shape, and is also known as Spongel (registered trademark) or Gelfoam (registered trademark). If a thin strip of gelatin sponge is injected into an artery, the gelatin sponge stagnates in the objective artery, and embolizes only the artery for a certain period of time together with thrombus formed there. The gelatin sponge strip integrated with the thrombus is gradually absorbed into the body on that spot, the artery is recanalized in about one or two weeks, and the gelatin sponge disappears from the inside of the body in one month.

A substance in the form of a fine strip of a size of about 100 to 300 μm, 300 to 500 μm, or 500 to 700 μm consisting of polyvinyl alcohol is a local infusion for artery embolization that eternally remains in an embolized blood vessel, and consists of a spherical substance of the standardized size, and therefore it does not clog a catheter, and is easily used.

Various spherical particles for artery embolization have been developed, and spherical PVA (Bead Block, Biocompatibles), non-water-absorptive spherical particles of acrylic copolymer impregnated and coated with pig gelatin (Embosphere, Biosphere Medical), spherical PVA imparted with drug dissolution ability (DC-Bead, Biocompatibles), water-absorptive and swellable bead consisting of polyvinyl alcohol/acrylic acid copolymer (Hepasphere, Biosphere Medical), acrylic hydrogel having special fluorine coating (Embozene, CeloNova), and the like are clinically used.

By preliminarily adding a substance having a PPARγ-agonistic activity and/or a PPARγ expression-inducing activity to such a local infusion for artery embolization as mentioned above, not only giant cell tumor or chondrosarcoma can be annihilated by stopping delivery of nutrition and oxygen to the giant cell tumor or chondrosarcoma, but also apoptosis can be induced in the giant cell tumor or chondrosarcoma to make the giant cell tumor or chondrosarcoma disappear, and the tumor can be differentiated into fat cells and thereby made to disappear. Therefore, a higher curative effect can be obtained.

Further, it is also frequently performed to, before the artery embolization, inject iodinated poppy seed oil fatty acid ethyl esters containing an anticancer agent into a tumor through a catheter inserted up to a position just before the tumor. Since iodinated poppy seed oil fatty acid ethyl esters constitute an oily contrast medium, the anticancer agent can be delivered into the inside of the tumor cells with confirming the injection state of the anticancer agent. Therefore, by injecting iodinated poppy seed oil fatty acid ethyl esters containing a substance having a PPARγ-agonistic activity and/or a PPARγ expression-inducing activity into giant cell tumor or chondrosarcoma through a catheter inserted into an artery, and then performing artery embolization, a higher curative effect can be obtained. Iodinated poppy seed oil fatty acid ethyl ester preparation is well known as Lipiodol (registered trademark).

In the present invention, the artificial bone means an artificial material for compensating a defective part of bone, and an artificial joint produced by using such a material. The material of the artificial bone is not limited to non-biological materials, and includes biological materials. The biological materials include autologous bone, homologous bone, and heterologous bone prepared through an artificial step such as adding a substance having a PPARγ-agonistic activity and/or a PPARγ expression-inducing activity.

When an ablative operation is performed as a radical therapy for giant cell tumor occurring in a bone and soft tissue, chondrosarcoma, or bone sarcoma, it is necessary to fill up the defective part formed after curettage or resection of a lesion with an artificial bone to secure bone strength. Further, since giant cell tumor occurring in a bone and soft tissue, chondrosarcoma, or bone sarcoma frequently occurs at a position near a joint, if an ablative operation is performed as a radical therapy, motor functions must be recovered by using an artificial joint after the curettage or resection of the lesion.

By using the artificial bone containing a substance having a PPARγ-agonistic activity and/or a PPARγ expression-inducing activity as an active ingredient, recurrence and/or metastasis of giant cell tumor occurring in a bone and soft tissue, chondrosarcoma, or bone sarcoma can be prevented.

In addition to strength, processability and compatibility with bone are required for the material of artificial bone, and as such a material of artificial bone, calcium phosphate type materials such as hydroxyapatite, metals such as titanium, titanium alloy, stainless steel, cobalt-chromium alloy, and tungsten, polymers such as polylactic acid, crosslinked polyethylene resin, silicon rubber, Teflon (registered trademark), polyester, and PVA hydrogel, glass, ceramics such as alumina and zirconia, bone cement such as polymethyl methacrylate, proteins such as collagen and fibrin, polysaccharides such as chitin and chitosan, coral materials, and composite materials of these can be used.

The artificial bone can be formed before surgical operation by scraping a material, molding, three-dimensional printing, or the like. As such artificial bone materials, calcium phosphate artificial bone materials similar to the bone components are most abundant in types, and various kinds of such materials are commercially produced and clinically used, including Apacerum (registered trademark), SuperPore (registered trademark), Biopex (registered trademark), Bonetight (registered trademark), Bonefill (registered trademark), Neobone (registered trademark), Regenos (registered trademark), OSferion (registered trademark), and the like.

The artificial joint is usually chosen from ready-made products consisting of a combination of such materials as metal, ceramics, and polyethylene resin, and used by embedding and fixing it in a bone.

Content of the substance having a PPARγ-agonistic activity and/or a PPARγ expression-inducing activity in the material of the artificial bone is preferably about 0.1 to 25%, more preferably about 1 to 20%, still more preferably about 5 to 15%, of the weight of the material of the artificial bone.

The screening method of the present invention can be implemented with the following steps:
(1) the step of culturing a cell or tissue originating in giant cell tumor occurring in a bone and soft tissue, chondrosarcoma, or bone sarcoma in the presence or absence of a test substance,
(2) the step of measuring one or more indices selected from the group consisting of those defined in (a) to (g) mentioned below in the presence or absence of the test substance;
(a) one or more indices selected from the group consisting of gene expression amount of PPARγ, and protein amount of PPARγ,
(b) one or more indices selected from the group consisting of gene expression amount of an apoptosis-related gene, protein amount of a translation product of an apoptosis-related gene, and biological activity of a translation product of an apoptosis-related gene,
(c) one or more indices selected from the group consisting of gene expression amount of a fat cell differentiation-related gene, protein amount of a translation product of a fat cell differentiation-related gene, and biological activity of a translation product of a fat cell differentiation-related gene,
(d) one or more indices selected from the group consisting of gene expression amount of an arteriosclerosis-related gene, protein amount of a translation product of an arteriosclerosis-related gene, and biological activity of a translation product of an arteriosclerosis-related gene,
(e) one or more indices selected from the group consisting of gene expression amount of an anti-inflammation-related gene, protein amount of a translation product of an anti-inflammation-related gene, and biological activity of a translation product of an anti-inflammation-related gene,
(f) an index consisting of a PPARγ-agonistic activity that can promote transcription of one or more kinds of genes selected from the group consisting of an apoptosis-related gene, a fat cell differentiation-related gene, an arteriosclerosis-related gene, and an anti-inflammation-related gene,
(g) amount of lipid contained in a fat cell or fat tissue, and
(3) the step of selecting a test substance that changes a value or values of the intracellular index or indices in the presence of a test substance compared with the value or values of the intracellular index or indices observed in the absence of the test substance.

As for the preparation of cells originating in giant cell tumor occurring in a bone and soft tissue, chondrosarcoma, or bone sarcoma used for the screening method of the present invention, those prepared by primarily culturing cells extracted by an ablative operation for tumor of a patient clinically diagnosed to have giant cell tumor occurring in a bone and soft tissue, chondrosarcoma, or bone sarcoma, or cells of a cell line established from such cells as mentioned above by a known method can be used.

A cell line can be established according to a method ordinarily performed in this field, or according to a description of published references. Further, the cells derived from giant cell tumor occurring in a bone and soft tissue, chondrosarcoma, or bone sarcoma may consist of an arbitrary tissue (for example, synovial membrane, joint, cartilage, and the like) containing the cells.

Although the culture condition for the cells originating in giant cell tumor occurring in a bone and soft tissue, chondrosarcoma, or bone sarcoma used for the screening method of the present invention can be appropriately adjusted in accordance with a known method, specifically, and for example, they can be cultured according to the methods described in the examples mentioned in this specification.

In the present invention, the PPARγ-agonistic activity and PPARγ expression-inducing activity can be confirmed by known methods.

Specifically, expression amount of the PPARγ gene can be measured by a method comprising extracting mRNAs from giant cell tumor occurring in a bone and soft tissue, chondrosarcoma, or bone sarcoma by a usual method, and performing a reverse transcription reaction and PCR using primers enabling amplification of the PPARγ transcription product. The transcription product and translation product of PPARγ are known, and for example, nucleotide sequence information of the transcription product is disclosed as GenBank accession No. BC006811.

Expression amount of each of the apoptosis-related gene, fat cell differentiation-related gene, arteriosclerosis-related gene, and anti-inflammation-related gene can also be measured by a known method on the basis of known gene information, like the measurement of expression amount of PPARγ gene already described.

Further, amount of the PPARγ protein can be measured by, for example, a PPAR antigen-antibody reaction using an antibody directed to the PPARγ protein, and a fixed specimen or disrupted cells of giant cell tumor occurring in a bone and soft tissue, chondrosarcoma, or bone sarcoma as a measurement sample. As for the translation product of the PPARγ gene, amino acid sequence information is disclosed as GenBank accession No. AAH06811.

Further, the PPARγ-agonistic activity can be confirmed by, for example, detecting dissociation of the co-repressor protein complex from the hetero-complex of PPARγ and RXR, or by detecting binding of the co-activator protein complex to the hetero-complex of PPARγ and RXR. Furthermore, the PPARγ-agonistic activity can also be confirmed by measuring expression level of a downstream gene, or expression level of a lipid.

Further, amount of protein as the translation product of the apoptosis-related gene, fat cell differentiation-related gene, arteriosclerosis-related gene, or anti-inflammation-related gene can also be measured by a known method on the basis of known information on each gene, as in the case of the measurement of amount of PPARγ protein already described.

As the method for measuring the PPARγ-agonistic activity, an ability to bind to PPARγ to change the conformation of the PPARγ protein can be measured, or amount of transcription product of a gene locating downstream from the PPAR response element (PPRE), or a translation product thereof can be measured. As for the method for measuring an ability to change the conformation of the PPARγ protein, competitive binding observed for a known agonist may be used as an index, or surface plasmon resonance may also be utilized.

Examples of the gene locating downstream from the PPAR response element (PPRE) include, for example, an apoptosis-related gene, fat cell differentiation-related gene, arteriosclerosis-related gene, anti-inflammation-related gene, and the like.

The apoptosis-related gene may be a gene carrying an apoptosis signal, or a marker gene for apoptosis. Examples of the apoptosis-related gene include, for example, those of caspase 3, p53, and the like.

As for the transcription product of caspase 3, for example, nucleotide sequence information is disclosed as GenBank accession No. BC016926, and as for the translation product thereof, amino acid sequence information is disclosed as GenBank accession No. AAH16926. The biological activity of the translation product of the caspase 3 gene can be measured on the basis of apoptosis, or can also be measured on the basis of the cysteine protease activity.

As for the transcription product of p53, for example, nucleotide sequence information is disclosed as GenBank accession No. NM_000546, and as for the translation product thereof, amino acid sequence information is disclosed as GenBank accession No. NP_000537. The biological activity of the translation product of the p53 gene can be measured on the basis of apoptosis, or can also be measured on the basis of change of control of cell cycle.

The fat cell differentiation-related gene may be a gene that induces differentiation into fat cells, or may be a marker gene for fat cell differentiation.

Examples of the fat cell differentiation-related gene include, for example, those of Setd8 (SET domain containing (lysine methyltransferase) 8), Setdb1 (SET domain, bifurcated 1), LPL (Lipoprotein Lipase), leptin, FABP4/aP2 (fatty acid-binding protein-4), adiponectin, a2Col6 (α chain 2 of type 6 collagen), and the like.

As for the transcription product of Setd8, for example, nucleotide sequence information is disclosed as GenBank accession No. NM_020382, and as for the translation product thereof, amino acid sequence information is disclosed as GenBank accession No. NP_065115. The biological activity of the translation product of the Setd8 gene can be measured on the basis of lipid production amount, or can also be measured on the basis of the enzyme activity for methylating the 20th lysine of the histone H4 protein.

As for the transcription product of Setdb1, for example, nucleotide sequence information is disclosed as GenBank accession No. NM_012432, and as for the translation product thereof, amino acid sequence information is disclosed as GenBank accession No. NP_036564. The biological activity of the translation product of the Setdb1 gene can be measured on the basis of lipid production amount, or can also be measured on the basis of the enzyme activity for methylating the 9th lysine of the histone H3 protein.

As for the transcription product of LPL, for example, nucleotide sequence information is disclosed as GenBank accession No. NM_000237, and as for the translation product thereof, amino acid sequence information is disclosed as GenBank accession No. NP_000228. The biological activity of the translation product of the LPL gene can be measured on the basis of the lipoprotein lipase activity.

As for the transcription product of leptin, for example, nucleotide sequence information is disclosed as GenBank accession No. NM_000230, and as for the translation product thereof, amino acid sequence information is disclosed as GenBank accession No. NP_000221. The biological activity of the translation product of the leptin gene can be measured on the basis of the appetite-suppressing activity observed when it is intravenously administered to a mammal, or can also be measured on the basis of the intracellular signal observed when the leptin protein binds to a cell that expresses a leptin receptor.

As for the transcription product of FABP4/aP2 (fat cell-specific fatty acid-binding protein), for example, nucleotide sequence information is disclosed as GenBank accession No. NM_001442, and as for the translation product thereof, amino acid sequence information is disclosed as GenBank accession No. NP_001433. The biological activity of the translation product of the FABP4/aP2 gene can be measured on the basis of efficiency of lipolysis of a cell that expresses the product.

As for the transcription product of adiponectin, for example, nucleotide sequence information is disclosed as GenBank accession No. NM_004797, and as for the translation product thereof, amino acid sequence information is disclosed as GenBank accession No. NP_004788. The biological activity of the translation product of the adiponectin gene can be measured on the basis of the AMP kinase-activating action, fatty acid-combusting action, or saccharide incorporation-promoting action exhibited when the product is allowed to act on cells of the liver or skeletal muscle.

As for the transcription product of a2Col6, for example, nucleotide sequence information is disclosed as GenBank accession No. BC065509, and as for the translation product thereof, amino acid sequence information is disclosed as GenBank accession No. AAH65509. The biological activity of the translation product of the a2Col6 gene can be measured on the basis of differentiation into fat cells as an index.

Examples of the arteriosclerosis-related gene include, for example, those of AT1R (angiotensin II receptor I), and the like. As for the transcription product of AT1R, nucleotide sequence information is disclosed as GenBank accession No. NM_000685, and as for the translation product thereof, amino acid sequence information is disclosed as GenBank accession No. NP_000676. The biological activity of the translation product of the AT1R gene can be measured on the basis of detection of expression cells using angiotensin II as a ligand.

Examples of the anti-inflammation-related gene include, for example, those of NF-κB (nuclear factor kappa-light-chain-enhancer of activated B cells), and the like. As for the transcription product of NF-κB, for example, nucleotide sequence information is disclosed as GenBank accession No. NM_003998, and as for the translation product thereof, amino acid sequence information is disclosed as GenBank accession No. NP_003989. The biological activity of the translation product of the NF-κB gene can be measured on the basis of dissociation thereof from IκB, and can also be measured on the basis of intranuclear transfer of NF-κB.

The lipid contained in fat cells or fat tissues is not particularly limited, and examples include phospholipids, glycolipids, lipoproteins, acylglycerols, ceramides, and the like.

Specifically, as for the measurement of the PPARγ expression-inducing activity, it can be examined by preparing an RNA (for example, total RNA, or mRNA) fraction from a cell, and detecting the transcription product of the PPARγ gene contained in the fraction. Such an RNA fraction can be prepared by a known method such as the guanidine-CsCl ultracentrifugation method and the AGPC method, and total RNA of high purity can be quickly and conveniently prepared from a small number of cells by using a commercial kit for RNA extraction (for example, RNeasy Mini Kit produced by QIAGEN and the like). Examples of the means for detecting a transcription product of a gene in an RNA fraction include, for example, a method of using hybridization (Northern blotting, dot blotting, DNA chip analysis, and the like), a method of using PCR (RT-PCR, competitive PCR, real-time PCR, and the like), and the like. The quantitative PCR method such as competitive PCR and real-time PCR is preferred, since it enables quick and convenient detection of change of expression of a gene from an extremely small amount of sample with good quantification ability.

As for the details of these measurement methods, they can be performed with reference to, for example, Molecular Cloning, 2nd edition (J. Sambrook et al., Cold Spring Harbor Lab. Press, 1989).

Expression of the PPARγ gene in a cell can be investigated by preparing a protein fraction from the cell, and detecting a translation product of the gene (namely, PPARγ protein) contained in the fraction. PPARγ can be detected by an immunoassay (for example, ELISA, FIA, RIA, Western blotting, and the like) using antibodies that specifically recognize the protein, or it can be detected by measuring the activity of the protein using a known method. Alternatively, the protein can also be detected by using mass spectrometry such as MALDI-TOFMS.

For the details of these general technical means, review articles, published books, and the like can be referred to. For example, "Radioimmunoassay", Edited by H. Irie (Kodansha, 1974), "Radioimmunoassay, Second Series", Edited by H. Irie (Kodansha, 1979), "Enzyme Immunoassay", Edited by E. Ishikawa et al. (Igaku-Shoin, 1978), "Enzyme Immunoassay", 2nd Edition, Edited by E. Ishikawa et al. (Igaku-Shoin, 1982), "Enzyme Immunoassay", 3rd Edition, Edited by E. Ishikawa et al. (Igaku-Shoin, 1987), "Methods in ENZYMOLOGY", Vol. 70 (Immunochemical Techniques (Part A)), ibid., Vol. 73 (Immunochemical Techniques (Part B)), ibid., Vol. 74 (Immunochemical Techniques (Part C)), ibid., Vol. 84 (Immunochemical Techniques (Part D: Selected immunoassays)), ibid., Vol. 92 (Immunochemical Techniques (Part E: Monoclonal Antibodies and General Immunoassay Methods)), ibid., Vol. 121 (Immunochemical Techniques (Part I: Hybridoma Technology and Monoclonal Antibodies)) (these are published by Academic Press), and the like can be referred to.

The PPARγ-agonistic activity can be measured in the same manner as that for the measurement of the PPARγ expression-inducing activity mentioned above, i.e., by preparing an RNA fraction, a protein fraction, or a lipid fraction from a cell, and detecting a transcription product, or a translation product of a gene locating downstream of the PPARγ gene (for example, apoptosis-related gene, fat cell differentiation-related gene, arteriosclerosis-related gene, anti-inflammation-related gene, and the like) or a lipid contained in the fraction. The methods for preparing the RNA fraction and the protein fraction and the methods for detecting them may be the same as the aforementioned methods explained for the measurement of the PPARγ expression-inducing activity.

As for the preparation method of a lipid, it may be prepared by using a known method, and there can be used, for example, the Folch method in which a lipid is extracted from a sample containing the lipid by adding several-fold volume of a solvent such as a mixture of chloroform and methanol to the sample, the Bligh-Dyer method in which a lipid is extracted by adding several-fold volume of a solvent such as a mixture of chloroform, methanol and water, or the like. Further, as for the method for detecting the separated lipid, it can be detected by using a known method such as liquid chromatography (LC), gas chromatography (GC), and high performance liquid chromatography (HPLC). Alternatively, a method of directly detecting a lipid contained in a fat cell or tissue may also be used. The reagents and the like usable for such a method are marketed, and for example, HCS LipidTOX Phospholipidosis and Steatosis Detection Kit (Invitrogen) and the like can be used.

Although change of value of an intracellular index measured in the screening method of the present invention may be increase in the value of intracellular index, or may be decrease in the value of intracellular index, increase in the value of intracellular index is preferred.

EXAMPLES

Hereafter, the present invention will be explained with reference to examples and reference examples. However, the present invention is not limited by the examples.

Example 1: Analysis of Suppression of Cell Proliferation and Apoptosis of Cultured Cells of Human Giant Cell Tumor of Bone (GCT) Observed after Culture with Addition of Zaltoprofen As for GCTB cultured cells (case 1, patient with giant cell tumor of bone in a distal part of the right femur, in twenties; case 2, patient with giant cell tumor of bone in a distal part of the right femur, in twenties), cells of tumor tissues derived from the patients were cultured by using the DMEM medium containing 2 mM L-glutamine, 10% fetal bovine serum (FBS), 100 U/mL of penicillin, and 100 μg/mL of streptomycin with reference to the report of Cheng Y Y et al. (Cheng Y Y, Huang L, Lee K M, et al., 2004, Bisphosphonates induce apoptosis of stromal tumor cells in giant cell tumor of bone, Calcif. Tissue Int., 75:71-77), repeatedly subcultured until there were only spindle-shaped cells, which state was gradually attained from the state that there were also multinucleated giant cells observed in an early stage, and then used for the following analysis. As for the analysis of suppression of cell proliferation, the cells were cultured overnight until the cells became sub-confluent on a 96-well culture plate using the DMEM medium containing 2 mM L-glutamine, 10% fetal bovine serum (FBS), 100 U/mL of penicillin, and 100 μg/mL of streptomycin in an incubator of 5% $CO_2$/95% air at 37° C., zaltoprofen was added to the cells at various concentrations (5, 10, 50, 100, and 200 μM), color development was attained with Cell Counting Kit-8 (CCK-8, Dojindo) 24 hours thereafter, and absorbance was measured at 450 nm further 3 hours thereafter (FIG. 1). As a result, zaltoprofen concentration-dependent suppression of the cell proliferation could be confirmed. Zaltoprofen was added as a solution in DMSO (dimethyl sulfoxide) prepared at a concentration 1000 times higher than the final concentration, and the solution was added in a volume of 0.1% of the volume of the medium. The same shall apply to the other drugs used in the following examples.

Further, the aforementioned GCTB cultured cells of the case 1 mentioned above were cultured on chamber cover slide glass, and zaltoprofen was added at different concentrations (100, and 200 μM) 24 hours afterward. Then, 8 hours and 24 hours afterward, the cells were fixed with 4% paraformaldehyde, staining with caspase 3 and Tunel assay were performed, and presence or absence of apoptosis was analyzed. In the Tunel assay, fragmented DNAs produced in the process of apoptosis were detected by the TdT-mediated dUTP nick end labeling method (TUNEL). Observation was performed with a fluorescence microscope (BZ-9000) of Keyence, and positive images for each concentration were quantitatively observed (FIGS. 2 to 5). As a result, zaltoprofen concentration and administration time-dependent increases of the Tunel-positive ratio and caspase 3-positive ratio could be confirmed.

Therefore, it was verified that zaltoprofen is useful for prophylactic treatment or therapeutic treatment of giant cell tumor of bone (GCT). It was also verified that suppression of proliferation of giant cell tumor of bone (GCT) by zaltoprofen is based on cell death caused by apoptosis.

Figure 6:
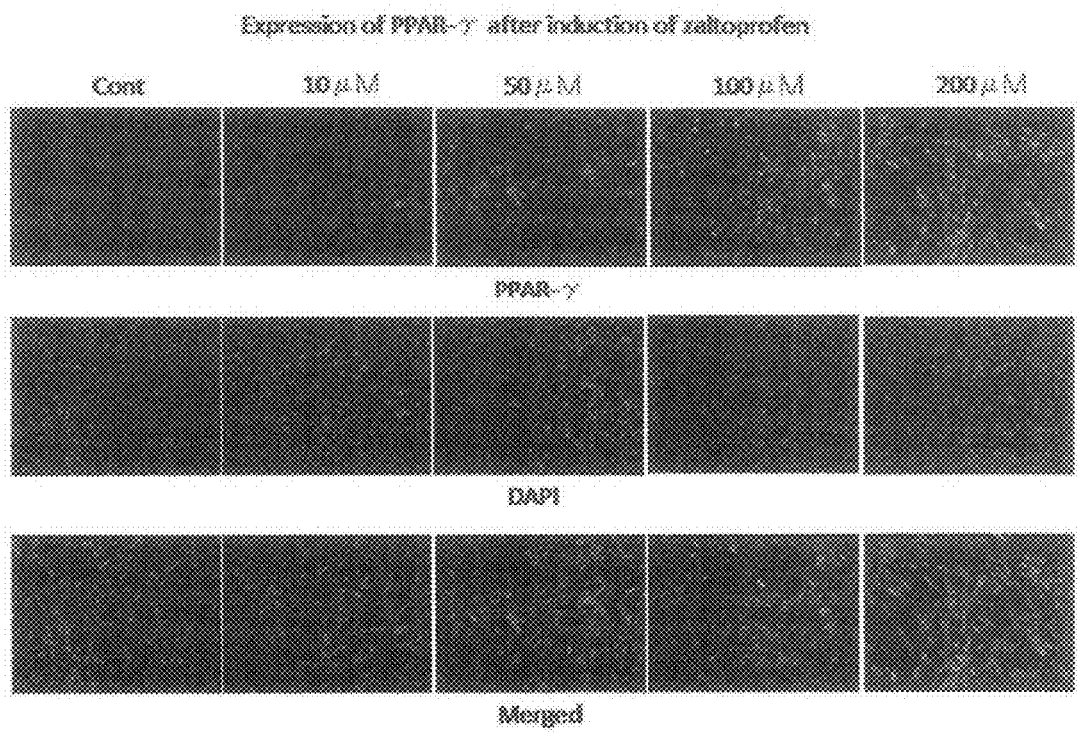
FIG. 6 Photographs showing results of PPARγ staining of GCTB cultured cells that were cultured in a zaltoprofen-containing medium. The concentrations are the concentrations of zaltoprofen. The indication of DAPI means that the results are results of nuclear staining with DAPI, which is a fluorescent dye.
Figure 7:
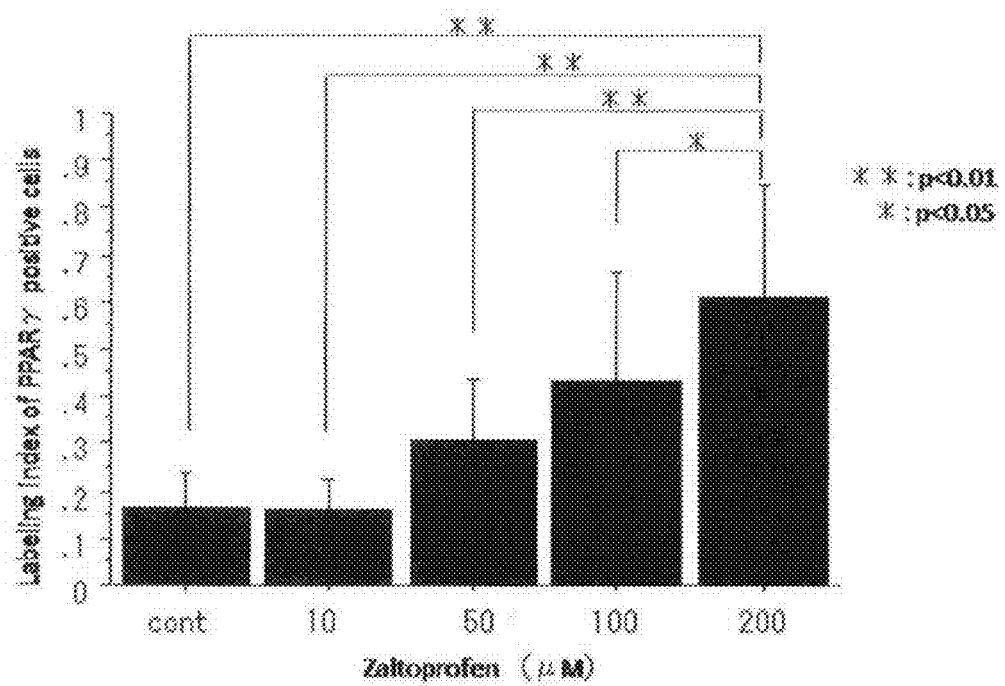
FIG. 7 A graph showing ratios of PPARγ-positive cells in GCTB cultured cells that were cultured in a zaltoprofen-containing medium. The concentrations indicated under the horizontal axis are the concentrations of zaltoprofen. The vertical axis represents the ratio of PPARγ-positive cells. The numerals on the right side of P< indicate the significance levels obtained as a result of statistical analysis.

Example 2: PPARγ Immunostaining of Cultured Cells of Human Giant Cell Tumor of Bone (GCTB) Performed after Culture with Addition of Zaltoprofen The GCTB cultured cells of the aforementioned case 1 were cultured on chamber cover slide glass, and 24 hours thereafter, zaltoprofen was added at various concentrations (10, 50, 100, and 200 μM). After 24 hours, the cells were fixed with 4% paraformaldehyde, and immunohistochemical staining of PPARγ was performed. The PPARγ protein was fluorescently detected by using the antibody SC-7273 of Santa Cruz Biotechnology, Inc. as the primary antibody and the rat anti-mouse IgG FITC (11-4011-85) of eBioscience as the secondary antibody. Observation was performed with a fluorescence microscope (BZ-9000) of Keyence, and positive images for each concentration were quantitatively observed (FIGS. 6 and 7). As a result, it was successfully confirmed that the expression of PPARγ was increased in a zaltoprofen concentration-dependent manner, while the expression of PPARγ was about 15% in the control.

Therefore, it was verified that zaltoprofen enables prophylactic treatment or therapeutic treatment of giant cell tumor of bone (GCTB) on the basis of promotion of expression of PPARγ.

Figure 8:
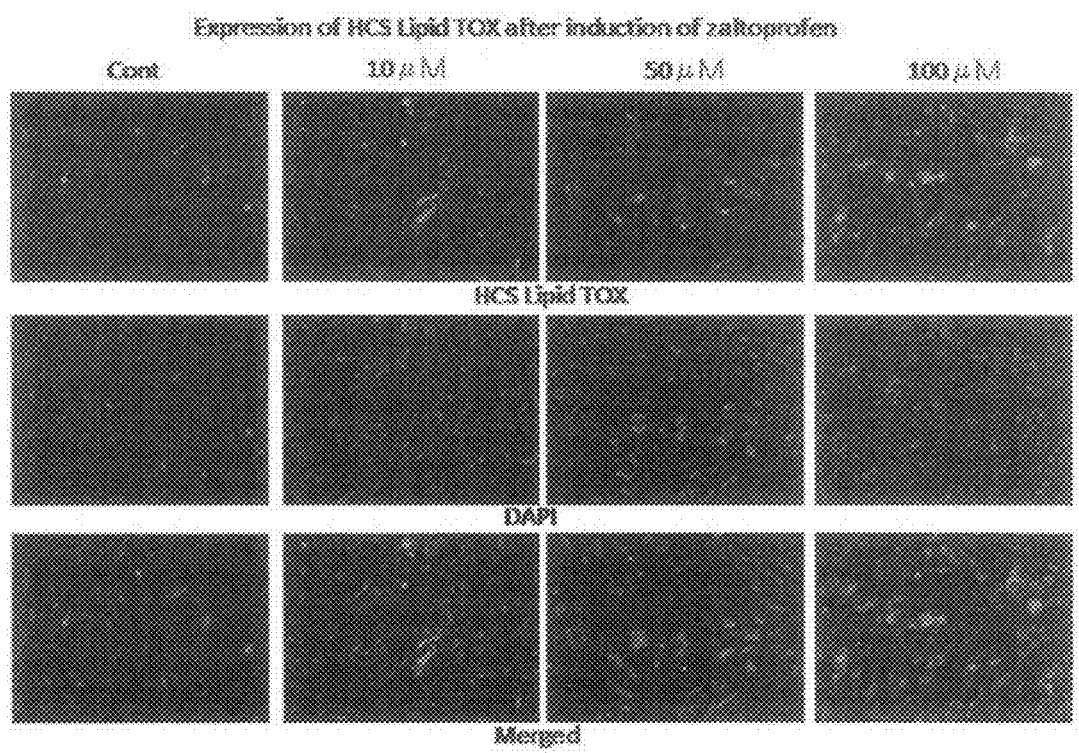
FIG. 8 Photographs showing results of lipid staining of GCTB cultured cells that were cultured in a zaltoprofen-containing medium. The concentrations are the concentrations of zaltoprofen. The indication of DAPI means that the results are results of nuclear staining with DAPI, which is a fluorescent dye.
Figure 9:
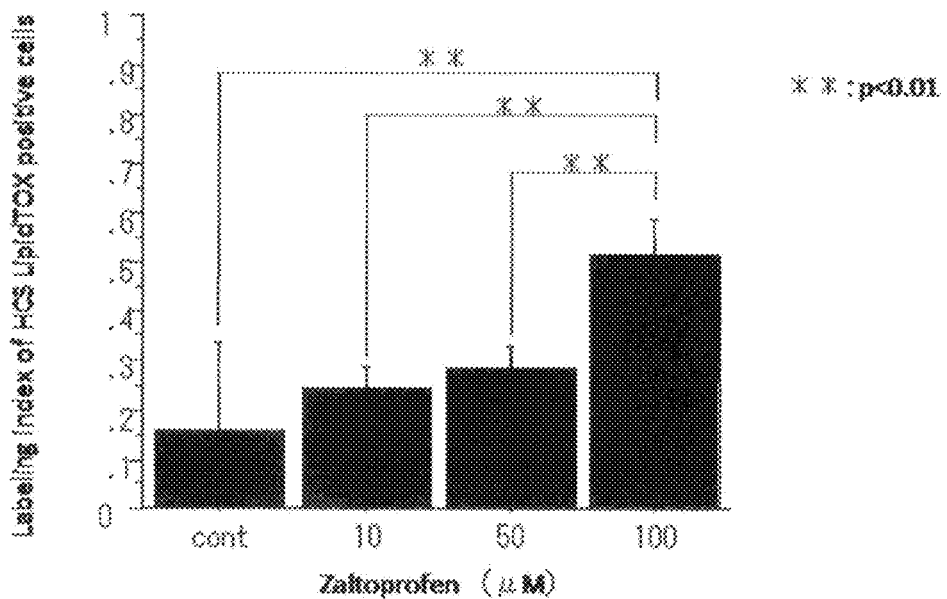
FIG. 9 A graph showing ratios of lipid-positive cells in GCTB cultured cells that were cultured in a zaltoprofen-containing medium. The concentrations indicated under the horizontal axis are the concentrations of zaltoprofen. The vertical axis represents the ratio of lipid-positive cells. The concentrations are the concentrations of zaltoprofen. The numerals on the right side of P< indicate the significance levels obtained as a result of statistical analysis.

Example 3: Analysis of Fat Cell Differentiation of Cultured Cells of Human Giant Cell Tumor of Bone (GCTB) Observed after Culture with Addition of Zaltoprofen to the GCTB Cultured Cells It has been reported that PPARγ is a transcription factor indispensable for fat cell differentiation. Therefore, the GCTB cultured cells of the aforementioned case 1 were cultured on chamber cover slide glass, and when they reached confluent, zaltoprofen was added to the cells at various concentrations (10, 50, and 100 μM). From 24 hours thereafter, the cells were cultured in a fat cell differentiation-inducing medium (STREMPRO Adipogenesis Differentiation Kit, Invitrogen) for 7 to 14 days, and differentiation into fat cells was analyzed with HCS Lipid TOX Green Neutral Lipid Stain (Invitrogen) (FIGS. 8 and 9). As a result, it was successfully confirmed that only a few positive images were obtained with HCS Lipid TOX Green Neutral Lipid Stain for the control, but positive images obtained with HCS Lipid TOX Green Neutral Lipid Stain were increased in a zaltoprofen concentration-dependent manner.

Therefore, it was verified that zaltoprofen enables prophylactic treatment or therapeutic treatment of giant cell tumor of bone (GCTB) by differentiating giant cell tumor of bone (GCTB) into fat cells, and thereby making the tumor disappear.

Figure 10:
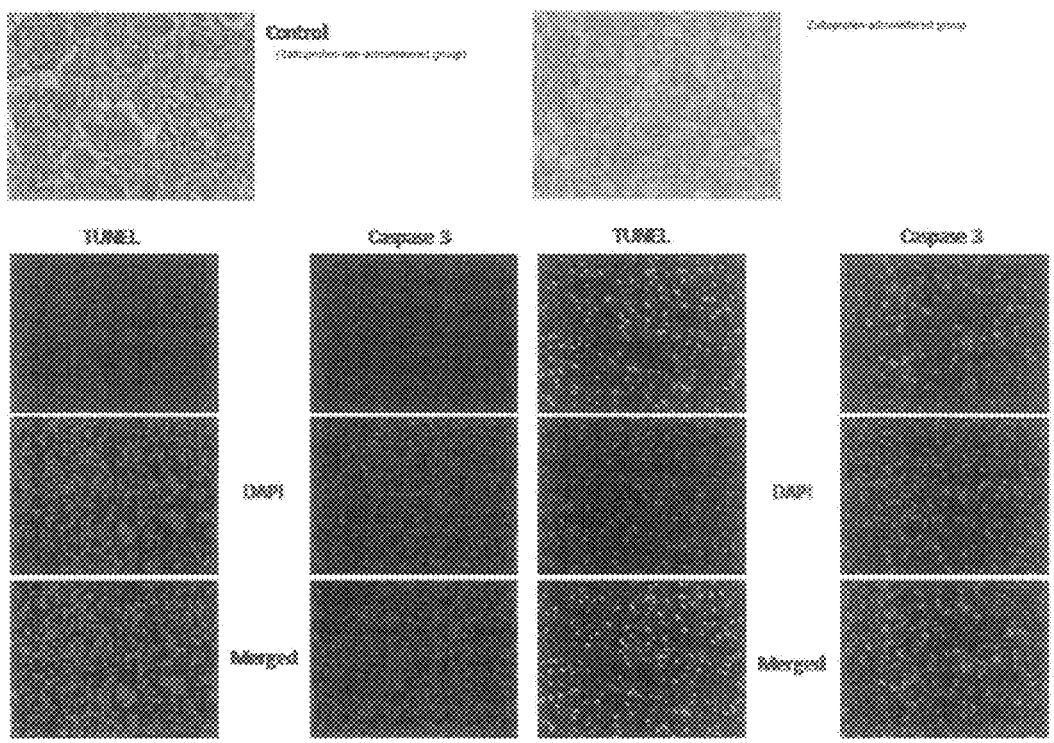
FIG. 10 Photographs showing results of Tunel assay and caspase 3 staining of GCTB samples derived from a GCTB patient administered with zaltoprofen. The indication of DAPI means that the results are results of nuclear staining with DAPI, which is a fluorescent dye.

Example 4: Analysis of Apoptosis of Cells Derived from Diseased Part of Patient with Giant Cell Tumor of Bone (GCTB) Administered with Zaltoprofen An operational excision sample of a man in his 30's who had been administered with 3 tablets per day of the zaltoprofen tablets, Soleton Tablet 80 (generic name: zaltoprofen, 80 mg, Nippon Chemiphar) for about 28 days for pain due to the tumor, and then subjected to the operation, and an operational excision sample of giant cell tumor of bone extracted from a patient with giant cell tumor of bone not administered with zaltoprofen (case in which tumor was excised by usual surgical operation according to standard therapy) as a control were subjected to caspase 3 staining and Tunel assay, and analyzed for the presence or absence of apoptosis. The caspase 3 protein was fluorescently detected by using Anti-ACTIVE Caspase-3-Ab (Roche) (G7481) (12-4739-81) as the primary antibody, and Donkey F2 Fragment anti-Rabbit IgG PE of eBioscience as the secondary antibody. Observation was performed with a fluorescence microscope (BZ-9000) produced by Keyence (FIG. 10). As a result, almost no Tunel-positive cells and caspase 3-positive cells could be confirmed among the cells derived from the GCTB patient not administered with zaltoprofen, whilst Tunel-positive cells and caspase 3-positive cells could be confirmed among the cells derived from the patient administered with zaltoprofen.

Therefore, it was verified in human that suppression of proliferation of giant cell tumor of bone (GCTB) by zaltoprofen is based on cell death caused by apoptosis.

Figure 11:
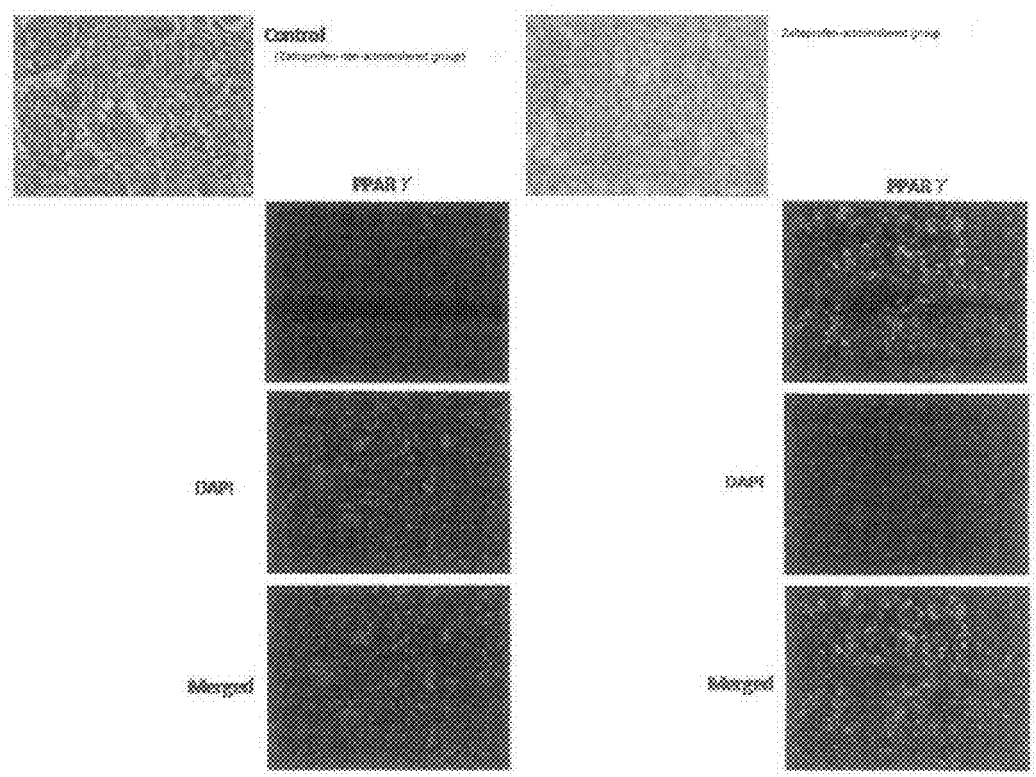
FIG. 11 Photographs showing results of PPARγ staining of GCTB samples derived from a GCTB patient administered with zaltoprofen. The indication of DAPI means that the results are results of nuclear staining with DAPI, which is a fluorescent dye.

Example 5: PPARγ Immunostaining of Cells Derived from Diseased Part of Patient with Giant Cell Tumor of Bone (GCTB) Administered with Zaltoprofen An operational excision sample of a man in his 30's who had been administered with 3 tablets per day of the zaltoprofen tablets, Soleton Tablet 80 (generic name: zaltoprofen, 80 mg, Nippon Chemiphar) for about 28 days for pain due to the tumor, and then subjected to the operation, and an operational excision sample of giant cell tumor of bone excised from a patient with giant cell tumor of bone not administered with zaltoprofen (case in which tumor was excised by usual surgical operation according to standard therapy) as a control were subjected to staining of PPARγ, and expression of PPARγ was analyzed by PCR. For PCR, Hs_PPARG_1_SGQuantiTect Primer Assay (200) (QT00029841) of QIAGEN was used. Observation was performed with a fluorescence microscope (BZ-9000) of Keyence (FIG. 11). As a result, almost no PPARγ-expressing cells could be confirmed among the cells derived from the GCTB patient not administered with zaltoprofen, whilst among the cells derived from the patient administered with zaltoprofen, PPARγ-expressing cells could be confirmed, and in addition, fat cell differentiation could be confirmed.

Therefore, it was verified in human that zaltoprofen enables prophylactic treatment or therapeutic treatment of giant cell tumor of bone (GCTB) by differentiating giant cell tumor of bone (GCTB) into fat cells on the basis of promotion of expression of PPARγ and thereby making the tumor disappear.

Figure 12:
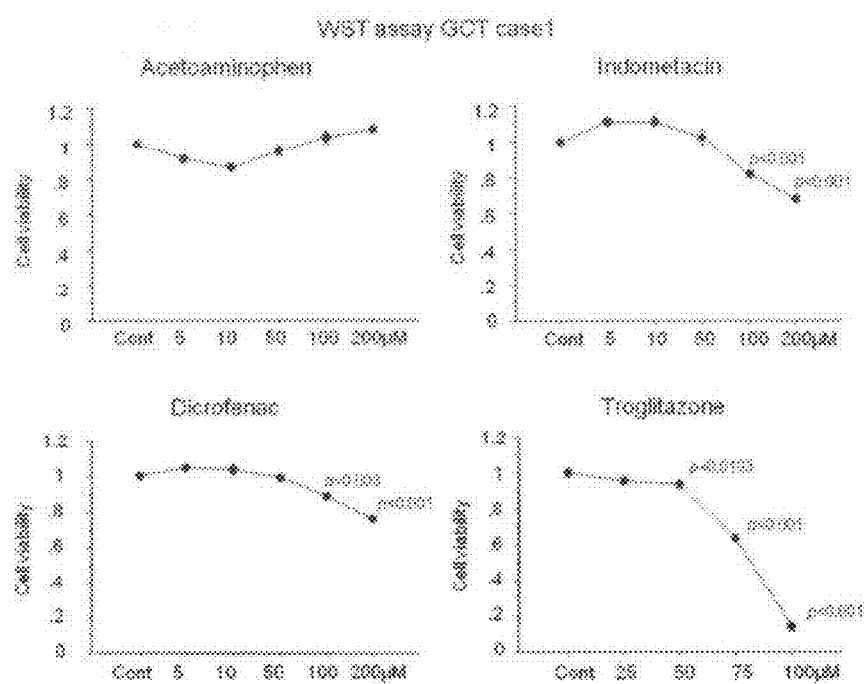
FIG. 12 Graphs showing results of suppression of proliferation of GCTB cultured cells that were cultured in an acetaminophen, indomethacin, diclofenac, or troglitazone-containing medium. The indication of GCT case 1 represents the origin of the cultured cells of giant cell tumor of bone. The indication of WST assay means that the cell proliferation was measured by using Cell Counting Kit-8 (CCK-8, Dojindo) using a tetrazolium salt WST-8 as a chromophoric substrate. The horizontal axes represent the concentration of each drug, and the vertical axes represent the live cell count measured on the basis of absorbance at 450 nm. The numerals on the right side of P< indicate the significance levels obtained as a result of statistical analysis.
Figure 13:
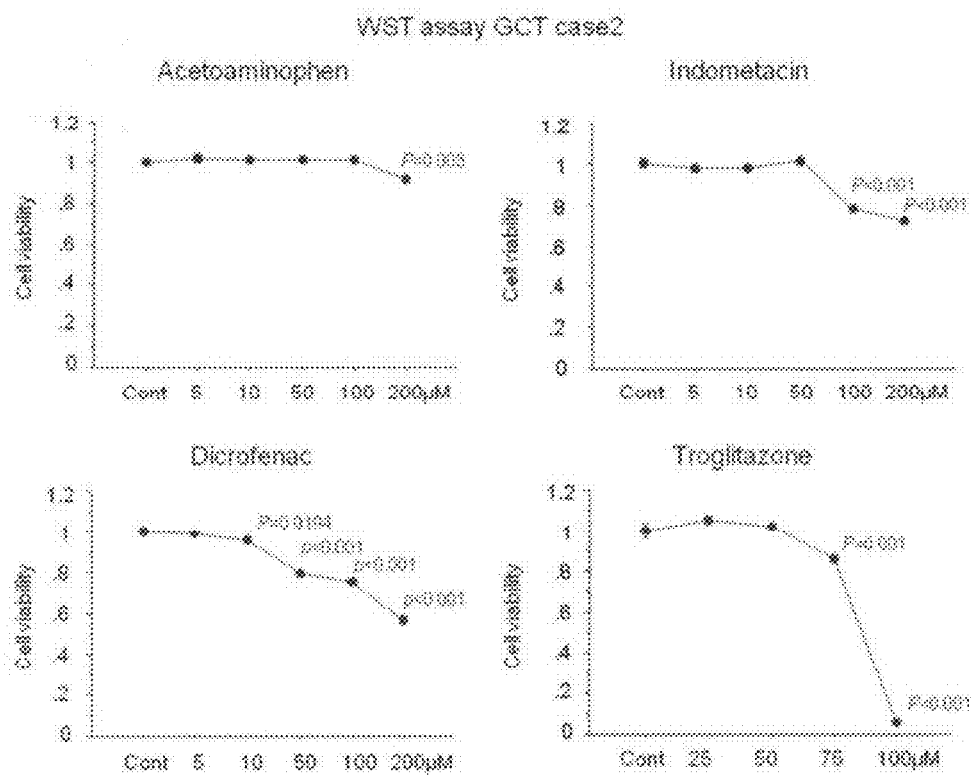
FIG. 13 Graphs showing results of suppression of proliferation of GCTB cultured cells that were cultured in an acetaminophen, indomethacin, diclofenac, or troglitazone-containing medium. The indication of GCT case 2 represents the origin of the cultured cells of giant cell tumor of bone. The indication of WST assay means that the cell proliferation was measured by using Cell Counting Kit-8 (CCK-8, Dojindo) using a tetrazolium salt WST-8 as a chromophoric substrate. The horizontal axes represent the concentration of each drug, and the vertical axes represent the live cell count measured on the basis of absorbance at 450 nm. The numerals on the right side of P< indicate the significance levels obtained as a result of statistical analysis.

Example 6: Analysis of Suppression of Cell Proliferation of Cultured Cells of Human Giant Cell Tumor of Bone (GCTB) Observed after Culture with Addition of Non-Steroidal Anti-Inflammatory Agent In the same manner as that of Example 1, the GCTB cultured cells (case 1, case 2) were cultured, a non-steroidal anti-inflammatory agent (acetaminophen, indomethacin, or diclofenac) or troglitazone was added at various concentrations, and absorbance was measured at 450 nm (FIGS. 12 and 13). As a result, it was successfully confirmed that the proliferation of cells was suppressed in a drug concentration-dependent manner.

Therefore, it was verified that these non-steroidal anti-inflammatory agents (acetaminophen, indomethacin, and diclofenac) and troglitazone enable prophylactic treatment or therapeutic treatment of giant cell tumor of bone (GCTB).

Figure 14:
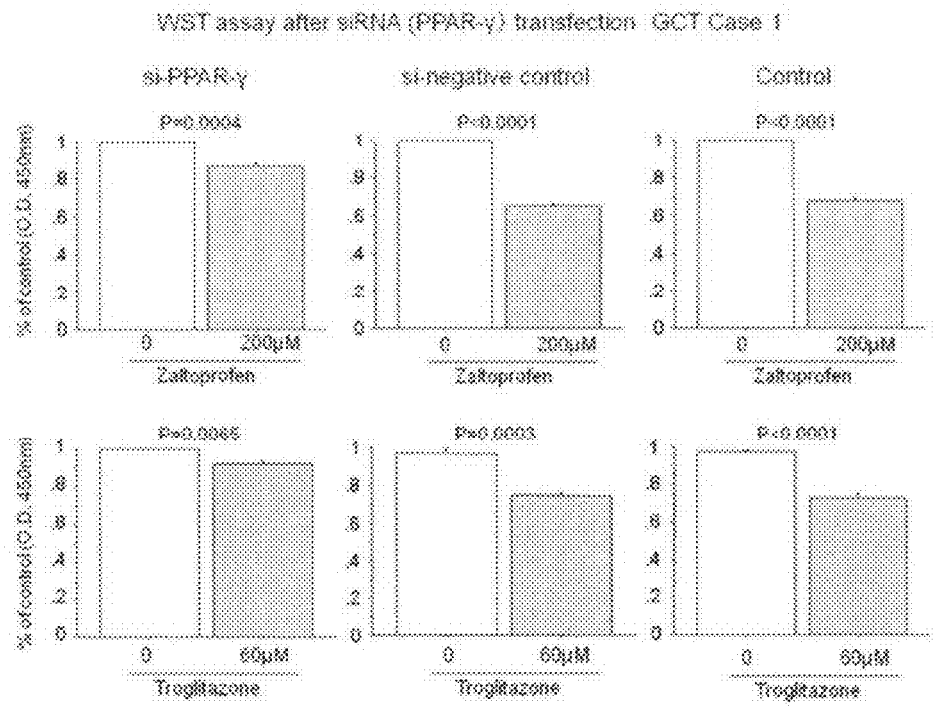
FIG. 14 Graphs showing effect of PPARγ siRNA on GCTB cultured cells that were cultured in a zaltoprofen or troglitazone-containing medium. The indication of GCT case 1 represents the origin of the cultured cells of giant cell tumor of bone. The indication of WST assay means that the cell proliferation was measured by using Cell Counting Kit-8 (CCK-8, Dojindo) using a tetrazolium salt WST-8 as a chromophoric substrate. The concentrations indicated under the horizontal axes are the concentrations of the drugs, and the vertical axes represent the live cell count measured on the basis of absorbance at 450 nm. The numerals on the right side of P indicate the significance levels obtained as a result of statistical analysis.
Figure 15:
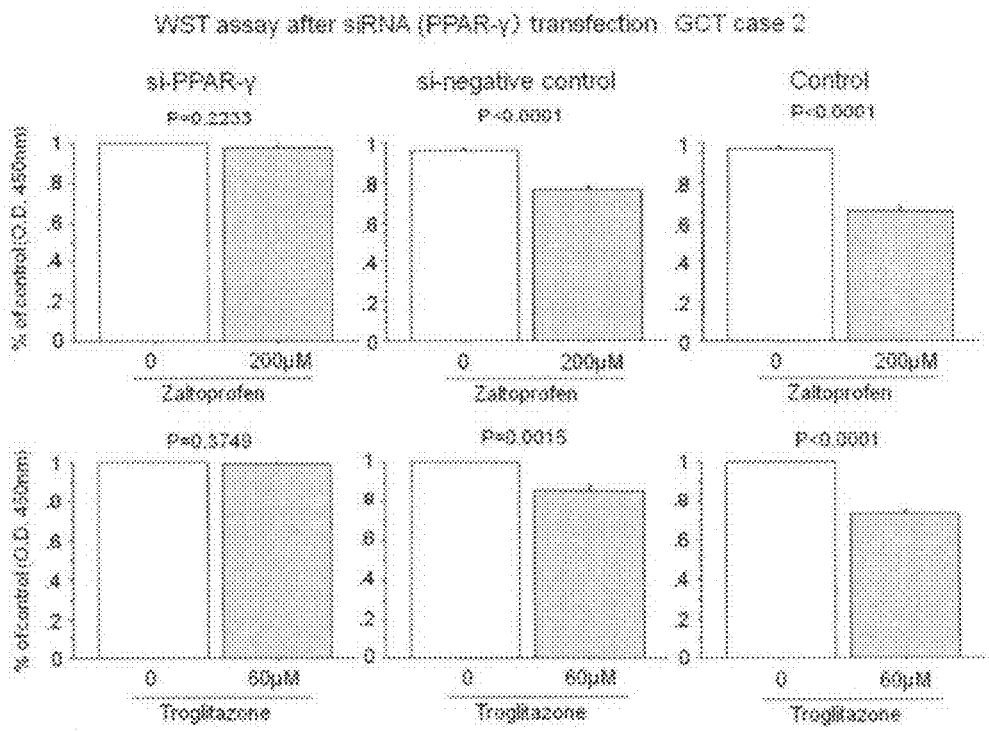
FIG. 15 Graphs showing effect of PPARγ siRNA on GCTB cultured cells that were cultured in a zaltoprofen or troglitazone-containing medium. The indication of GCT case 2 represents the origin of the cultured cells of giant cell tumor of bone. The indication of WST assay means that the cell proliferation was measured by using Cell Counting Kit-8 (CCK-8, Dojindo) using a tetrazolium salt WST-8 as a chromophoric substrate. The concentrations indicated under the horizontal axes are the concentrations of the drugs, and the vertical axes represent the live cell count measured on the basis of absorbance at 450 nm. The numerals on the right side of P indicate the significance levels obtained as a result of statistical analysis.

Example 7: Cell Proliferation-Inhibitory PPAR Effect of Zaltoprofen and Troglitazone on Cultured Cells of Human Giant Cell Tumor of Bone (GCTB) Cultured in the Presence or Absence of PPARγ siRNA The cells (case 1, case 2) were cultured on a 96-well culture plate, allowed to react with PPARγ siRNA (Dharmacon, catalog number M-003436-02-0005) that selectively inhibits expression of PPARγ, control siRNA (Dharmacon, catalog number D-001206-14-05, final concentration 100 nM), negative control siRNA designed so as not to have the gene expression inhibitory action, or only the transfection reagents (Thermo Scientific DharmaFECT, Thermo Scientific) for 48 hours, and further cultured in a usual culture medium for 48 hours. Then, 200 μM of zaltoprofen or 60 μM of troglitazone was added to the cells, 72 hours thereafter, color development was performed with Cell Counting Kit-8 (CCK-8, Dojindo), and 3 hours thereafter, absorbance was measured at 450 nm (FIGS. 14 and 15). As a result, it was successfully confirmed that the cell proliferation-inhibiting effect of zaltoprofen and troglitazone was significantly suppressed in the PPARγ siRNA addition group.

Therefore, it was verified that zaltoprofen and troglitazone are useful for prophylactic treatment or therapeutic treatment of giant cell tumor of bone (GCTB). It was also verified that expression of PPARγ is indispensable for suppression of proliferation of giant cell tumor of bone (GCTB) by zaltoprofen and troglitazone.

Figure 16:
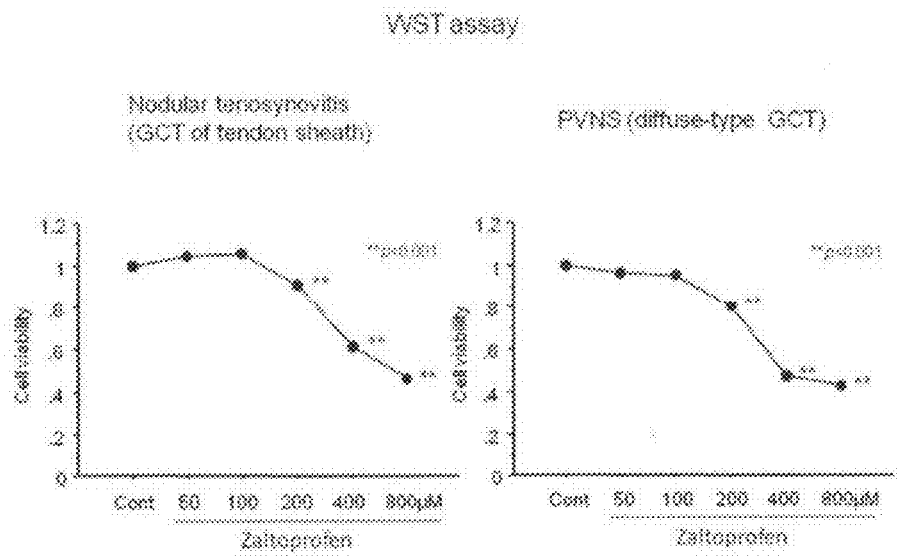
FIG. 16 Graphs showing results of suppression of proliferation of cultured cells derived from giant cell tumor of tendon sheath (GCTT) or cultured cells derived from pigmented villonodular synovitis (PVNS) cultured in a zaltoprofen-containing medium. The indication of WST assay means that the cell proliferation was measured by using Cell Counting Kit-8 (CCK-8, Dojindo) using a tetrazolium salt WST-8 as a chromophoric substrate. The horizontal axes represent the concentration of zaltoprofen, and the vertical axes represent the live cell count measured on the basis of absorbance at 450 nm. The numerals on the right side of P< indicate the significance levels obtained as a result of statistical analysis.
Figure 17:
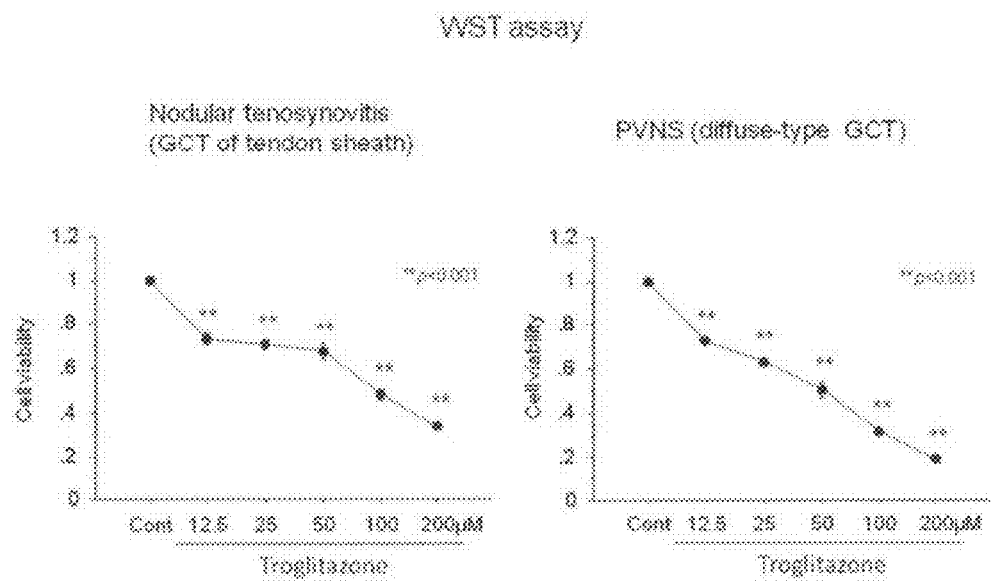
FIG. 17 Graphs showing results of suppression of proliferation of cultured cells derived from giant cell tumor of tendon sheath (GCTT) or cultured cells derived from pigmented villonodular synovitis (PVNS) cultured in a troglitazone-containing medium. The indication of WST assay means that the cell proliferation was measured by using Cell Counting Kit-8 (CCK-8, Dojindo) using a tetrazolium salt WST-8 as a chromophoric substrate. The horizontal axes represent the concentration of troglitazone, and the vertical axes represent the live cell count measured on the basis of absorbance at 450 nm. The numerals on the right side of P< indicate the significance levels obtained as a result of statistical analysis.
Figure 18:
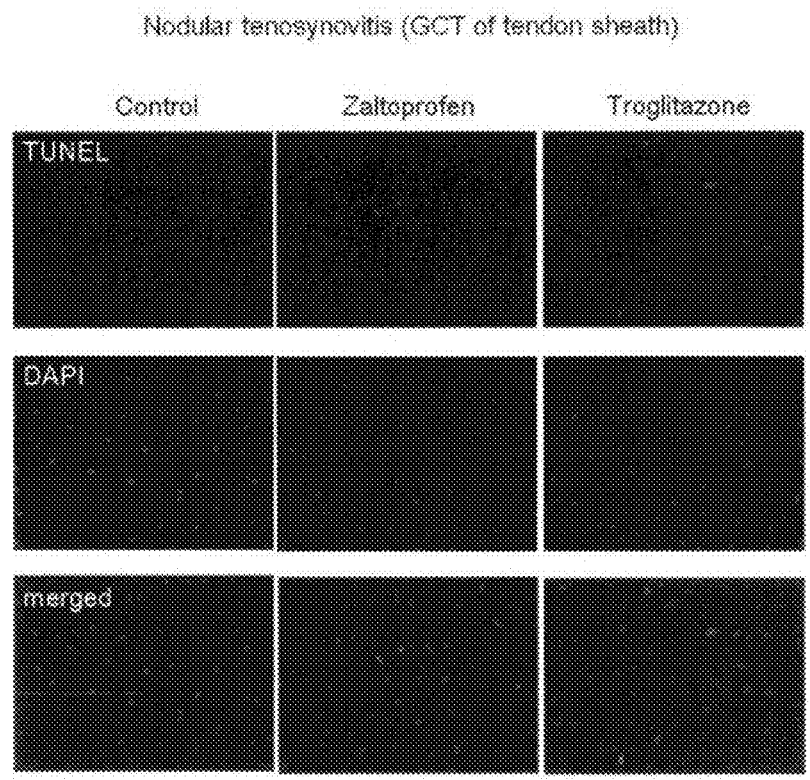
FIG. 18 Photographs showing results of Tunel assay of cultured cells derived from giant cell tumor of tendon sheath (GCTT) cultured in a zaltoprofen or troglitazone-containing medium. In the Tunel assay, fragmented DNAs produced in the process of apoptosis were detected by the TdT-mediated dUTP nick end labeling method (TUNEL). The indication of DAPI means that the results are results of nuclear staining with DAPI, which is a fluorescent dye.
Figure 19:
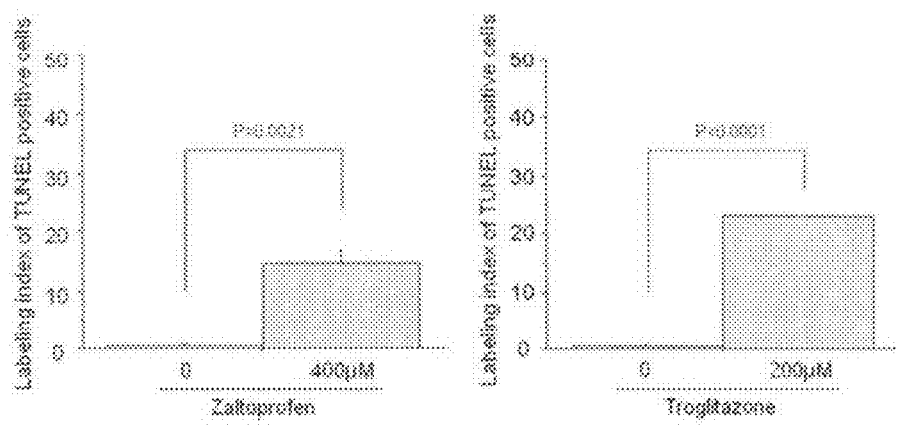
FIG. 19 Graphs showing ratios of Tunel-positive cells in cultured cells derived from giant cell tumor of tendon sheath (GCTT) cultured in a zaltoprofen or troglitazone-containing medium. The vertical axes represent the ratio of Tunel-positive cells, and the concentrations indicated under the horizontal axes are the concentrations of the drugs. The numerals on the right side of P indicate the significance levels obtained as a result of statistical analysis.
Figure 20:
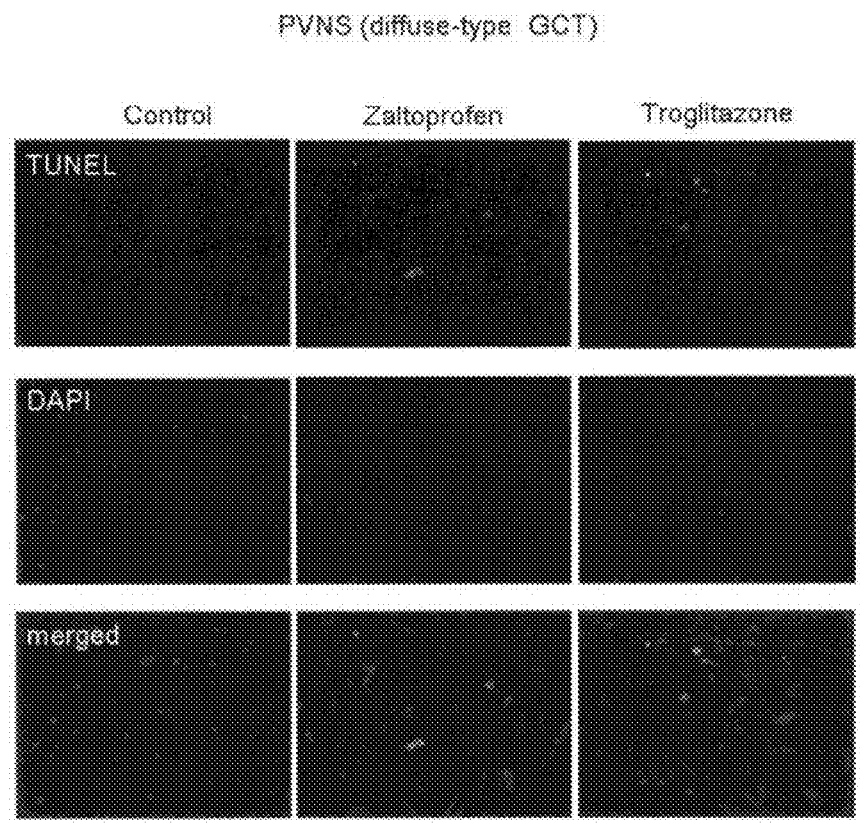
FIG. 20 Photographs showing results of Tunel assay of cultured cells derived from pigmented villonodular synovitis (PVNS) cultured in a zaltoprofen or troglitazone-containing medium. In the Tunel assay, fragmented DNAs produced in the process of apoptosis were detected by the TdT-mediated dUTP nick end labeling method (TUNEL). The indication of DAPI means that the results are results of nuclear staining with DAPI, which is a fluorescent dye.
Figure 21:
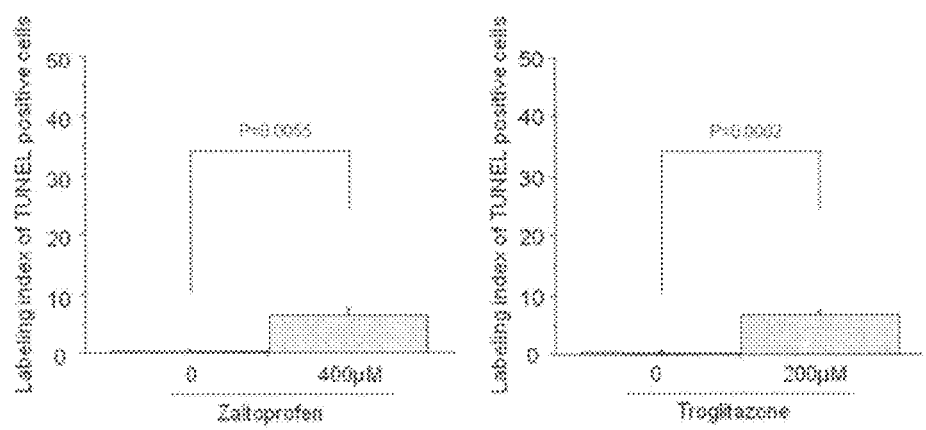
FIG. 21 Graphs showing ratios of Tanel-positive cells in cultured cells derived from pigmented villonodular synovitis (PVNS) cultured in a zaltoprofen or troglitazone-containing medium. The vertical axes represent the ratio of Tunel-positive cells, and the concentrations indicated under the horizontal axes are the concentrations of the drugs. The numerals on the right side of P indicate the significance levels obtained as a result of statistical analysis.
Figure 22:
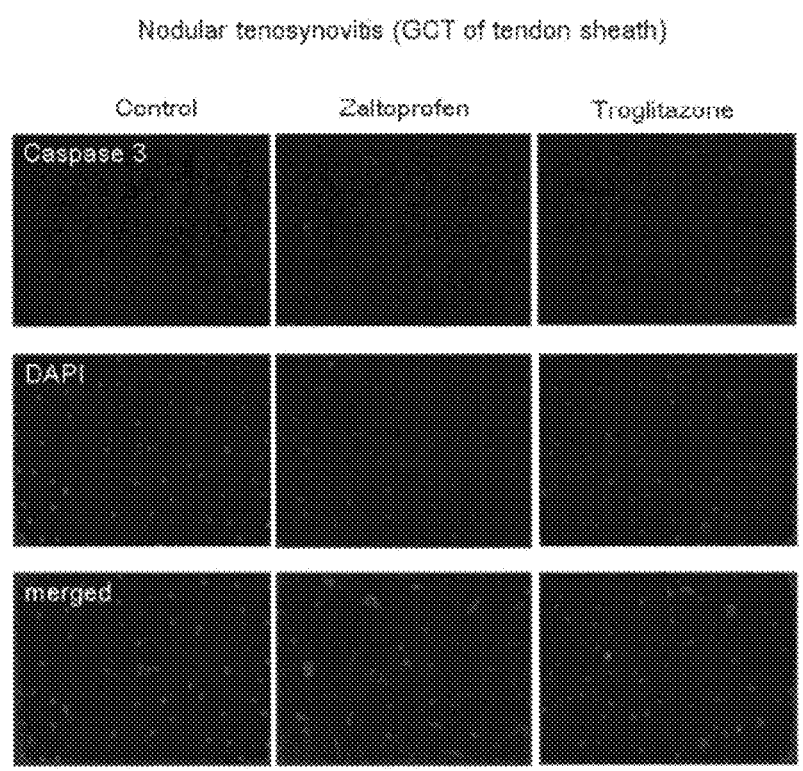
FIG. 22 Photographs showing results of caspase 3 staining of cultured cells derived from giant cell tumor of tendon sheath (GCTT) cultured in a zaltoprofen or troglitazone-containing medium. The indication of DAPI means that the results are results of nuclear staining with DAPI, which is a fluorescent dye.
Figure 23:
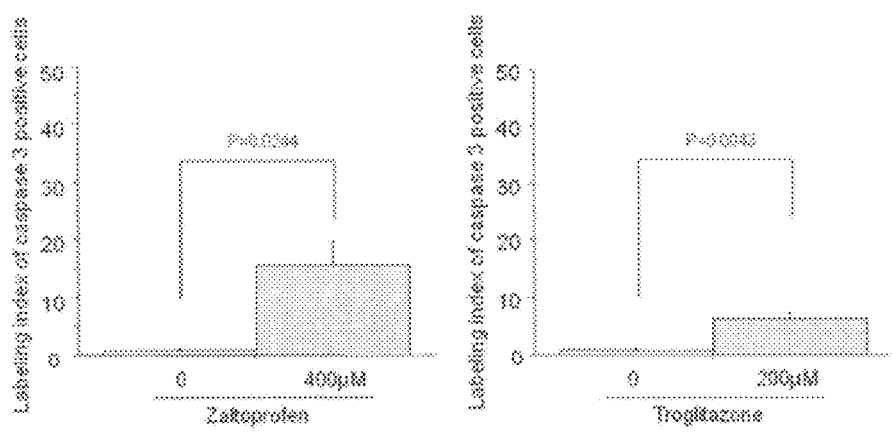
FIG. 23 Graphs showing ratios of caspase 3-positive cells in cultured cells derived from giant cell tumor of tendon sheath (GCTT) cultured in a zaltoprofen or troglitazone-containing medium. The vertical axes represent the ratio of caspase 3-positive cells, and the concentrations indicated under the horizontal axes are the concentrations of the drugs. The numerals on the right side of P indicate the significance levels obtained as a result of statistical analysis.
Figure 24:
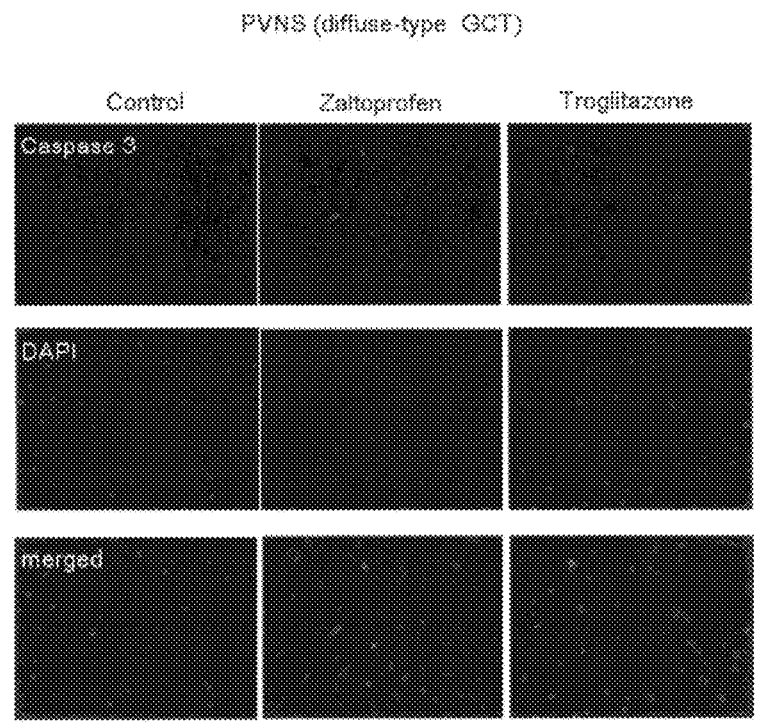
FIG. 24 Photographs showing results of caspase 3 staining of cultured cells derived from pigmented villonodular synovitis (PVNS) cultured in a zaltoprofen or troglitazone-containing medium. The indication of DAPI means that the results are results of nuclear staining with DAPI, which is a fluorescent dye.
Figure 25:
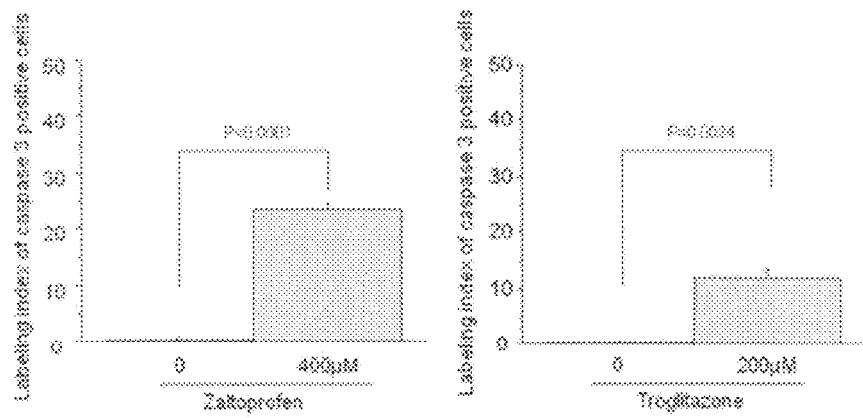
FIG. 25 Graphs showing ratios of caspase 3-positive cells in cultured cells derived from pigmented villonodular synovitis (PVNS) cultured in a zaltoprofen or troglitazone-containing medium. The vertical axes represent the ratio of caspase 3-positive cells, and the concentrations indicated under the horizontal axes are the concentrations of the drugs. The numerals on the right side of P indicate the significance levels obtained as a result of statistical analysis.
Figure 26:
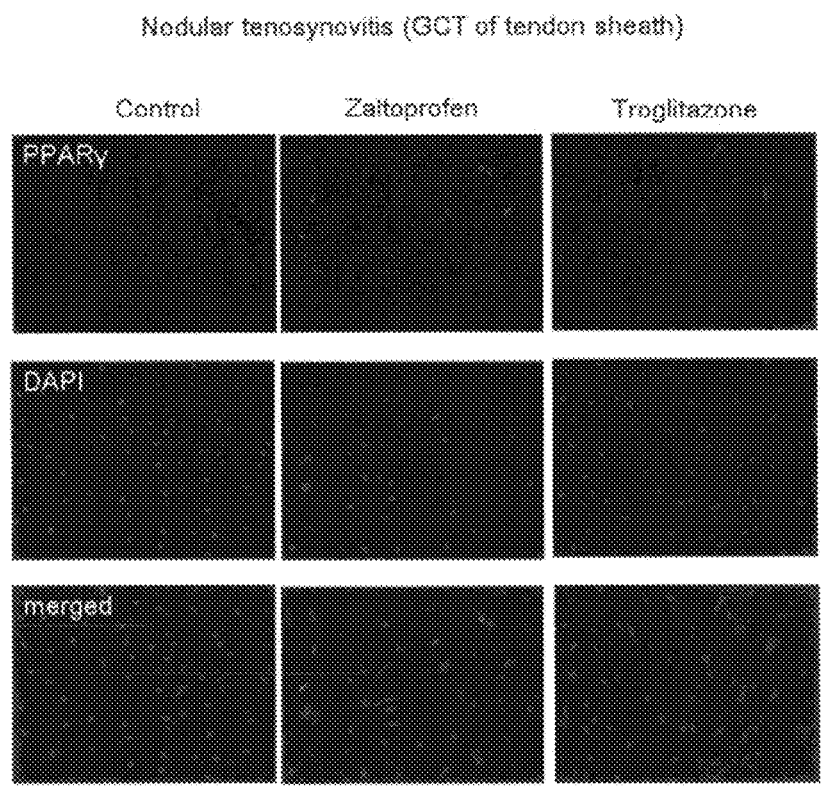
FIG. 26 Photographs showing results of PPARγ staining of cultured cells derived from giant cell tumor of tendon sheath (GCTT) cultured in a zaltoprofen or troglitazone-containing medium. The indication of DAPI means that the results are results of nuclear staining with DAPI, which is a fluorescent dye.
Figure 27:
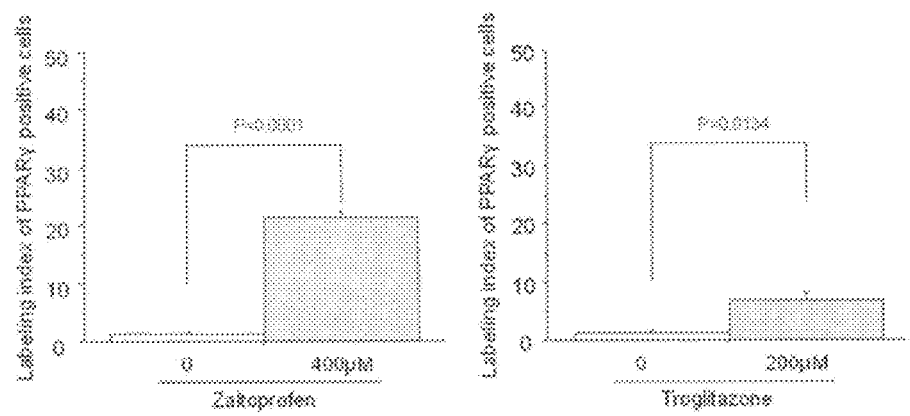
FIG. 27 Graphs showing ratios of PPARγ-positive cells in cultured cells derived from giant cell tumor of tendon sheath (GCTT) cultured in a zaltoprofen or troglitazone-containing medium. The vertical axes represent the ratio of PPARγ-positive cells, and the concentrations indicated under the horizontal axes are the concentrations of the drugs. The numerals on the right side of P indicate the significance levels obtained as a result of statistical analysis.
Figure 28:
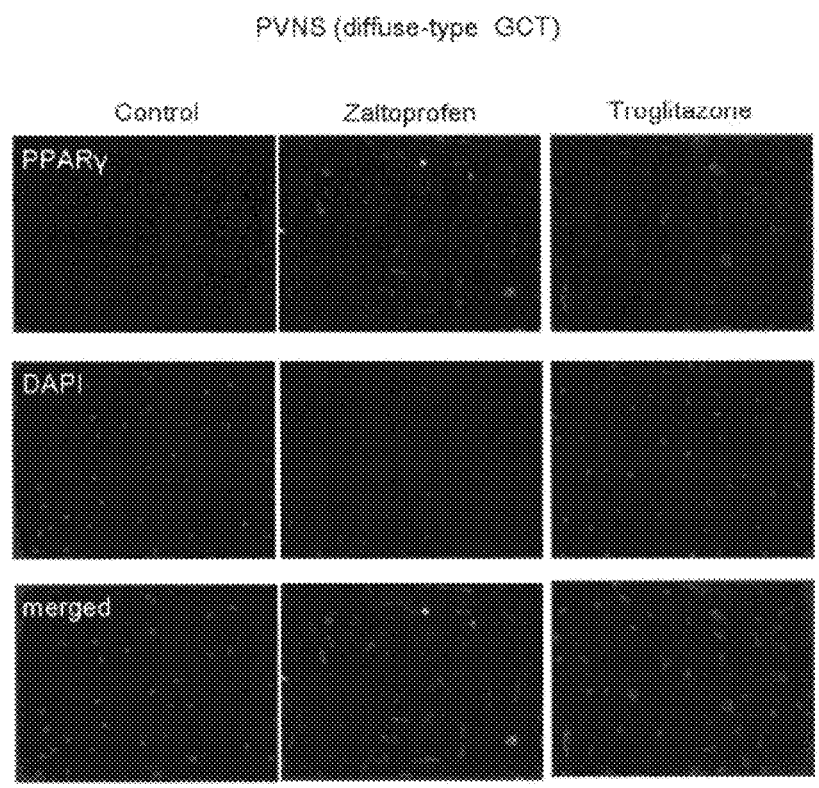
FIG. 28 Photographs showing results of PPARγ staining of cultured cells derived from pigmented villonodular synovitis (PVNS) cultured in a zaltoprofen or troglitazone-containing medium. The indication of DAPI means that the results are results of nuclear staining with DAPI, which is a fluorescent dye.
Figure 29:
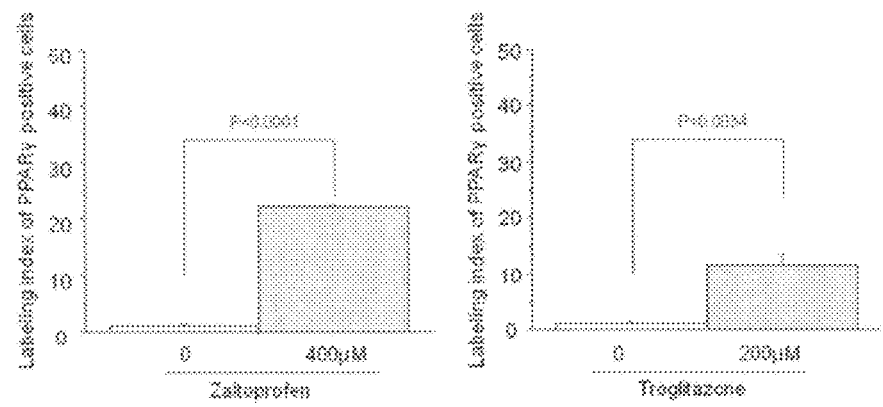
FIG. 29 Graphs showing ratios of PPARγ-positive cells in cultured cells derived from pigmented villonodular synovitis (PVNS) cultured in a zaltoprofen or troglitazone-containing medium. The vertical axes represent the ratio of PPARγ-positive cells, and the concentrations indicated under the horizontal axes are the concentrations of the drugs. The numerals on the right side of P indicate the significance levels obtained as a result of statistical analysis.

Example 8: Analysis of Suppression of Cell Proliferation and Apoptosis of Cells of Human Giant Cell Tumor of Tendon Sheath (GCTT) or Cells of Human Pigmented Villonodular Synovitis (PVNS) Observed after Culture with Addition of Non-Steroidal Anti-inflammatory Agent or Thiazolidine Derivative In the same manner as that of Example 1, cultured cells of giant cell tumor of tendon sheath (GCTT) (derived from a patient with giant cell tumor of tendon sheath in the right knee, in 30's, to whom only surgical operation was performed according to standard therapy) and cultured cells of pigmented villonodular synovitis (PVNS) (derived from the patient of case k with pigmented villonodular synovitis in the left knee, in 30's) were cultured from tumor tissues derived from the patients by using the DMEM medium containing 2 mM L-glutamine, 10% fetal bovine serum (FBS), 100 U/mL of penicillin, and 100 μg/mL of streptomycin with reference to the report of Cheng Y Y et al. (Cheng Y Y, Huang L, Lee K M, et al., 2004, Bisphosphonates induce apoptosis of stromal tumor cells in giant cell tumor of bone, Calcif Tissue Int., 75:71-77), repeatedly subcultured until there were only spindle-shaped cells, which state was gradually attained from the state that there were also multinucleated giant cells observed in an early stage, and then used for the following analysis. As for the analysis of suppression of cell proliferation, the cells were cultured overnight until they became sub-confluent on a 96-well culture plate using the DMEM medium containing 2 mM L-glutamine, 10% fetal bovine serum (FBS), 100 U/mL of penicillin, and 100 μg/mL of streptomycin in an incubator of 5% $CO_2$/95% air at 37° C., zaltoprofen (50, 100, 200, 400, and 800 μM) or troglitazone (12.5, 25, 50, 100, and 200 μM) was added to the cells, color development was performed with Cell Counting Kit-8 (CCK-8, Dojindo) 24 hours thereafter, and absorbance was measured at 450 nm further 3 hours thereafter (FIGS. 16 and 17). As a result, it was successfully confirmed that the cell proliferation was suppressed in a zaltoprofen or troglitazone concentration-dependent manner.

Therefore, it was verified that zaltoprofen and troglitazone are useful for prophylactic treatment or therapeutic treatment of giant cell tumor of tendon sheath (GCTT) and pigmented villonodular synovitis (PVNS).

Further, in the same manner as that of Example 1, the cultured cells of human giant cell tumor of tendon sheath (GCTT) and the cultured cells of human pigmented villonodular synovitis (PVNS) were subjected to staining with caspase 3 and Tunel assay, and presence or absence of apoptosis was analyzed (FIGS. 18 to 25). As a result, it was successfully confirmed that the Tunel-positive ratio and caspase 3-positive ratio increased in the cells added with zaltoprofen at a concentration of 400 µM or troglitazone at a concentration of 200 µM compared with those observed for the control.

Therefore, it was verified that zaltoprofen and troglitazone suppress proliferation of cells of giant cell tumor of tendon sheath (GCTT) and pigmented villonodular synovitis (PVNS) on the basis of cell death caused by apoptosis.

Example 9: PPARγ Immunostaining of Cells of Giant Cell Tumor of Tendon Sheath (GCTT) or Cells of Pigmented Villonodular Synovitis (PVNS) Performed after Culture with Addition of Non-Steroidal Anti-Inflammatory Agent or Thiazolidine Derivative In the same manner as that of Example 2, zaltoprofen or troglitazone was added at concentration of 400 µM or 200 µM, respectively, to the cells of giant cell tumor of tendon sheath (GCTT) or cells of pigmented villonodular synovitis (PVNS), and PPARγ-positive images was confirmed (FIGS. 26 to 29). As a result, expression of PPARγ was successfully observed in the zaltoprofen or troglitazone-added cells.

Therefore, it was verified that zaltoprofen and troglitazone enable prophylactic treatment or therapeutic treatment of giant cell tumor of tendon sheath (GCTT) and pigmented villonodular synovitis (PVNS) on the basis of promotion of expression of PPARγ.

Figure 30:
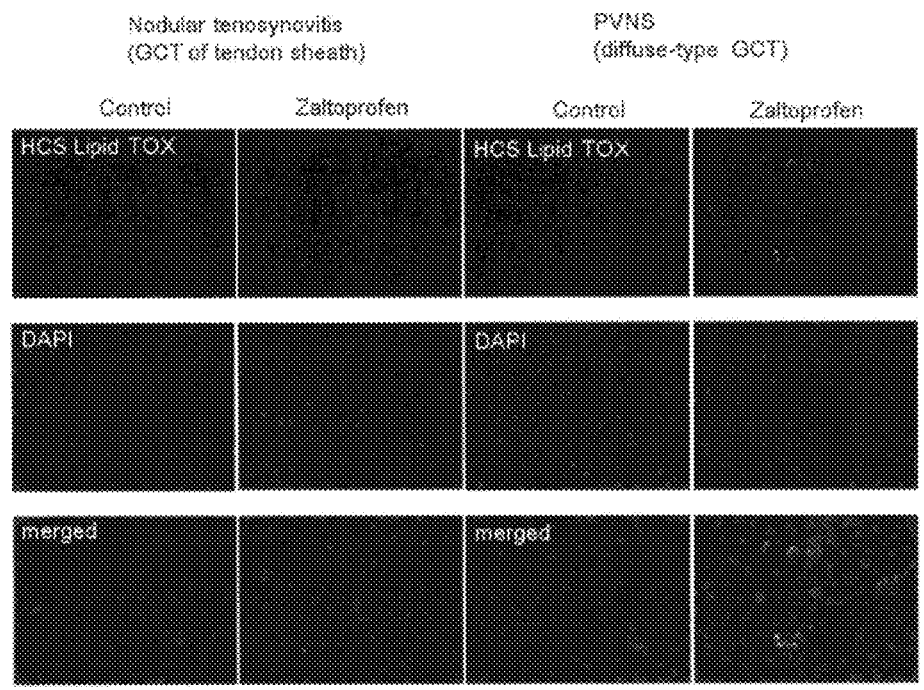
FIG. 30 Photographs showing results of lipid staining of cultured cells derived from giant cell tumor of tendon sheath (GCTT) or cultured cells derived from pigmented villonodular synovitis (PVNS) cultured in a zaltoprofen-containing medium. The indication of DAPI means that the results are results of nuclear staining with DAPI, which is a fluorescent dye.
Figure 31:
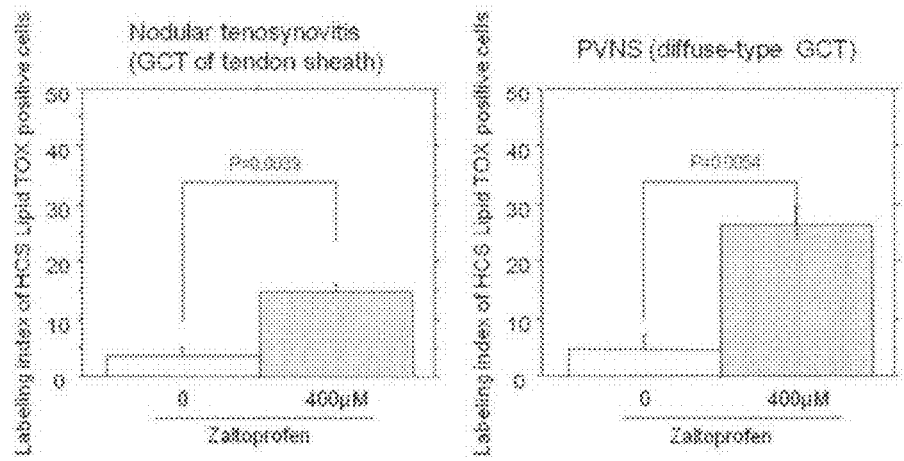
FIG. 31 Graphs showing ratios of lipid-positive cells in cultured cells derived from giant cell tumor of tendon sheath (GCTT) or cultured cells derived from pigmented villonodular synovitis (PVNS) cultured in a zaltoprofen-containing medium. The vertical axes represents the ratio of lipid-positive cells, and the concentrations indicated under the horizontal axes are the concentrations of the drugs. The numerals on the right side of P indicate the significance levels obtained as a result of statistical analysis.

Example 10: Analysis of Fat Cell Differentiation of Cells of Giant Cell Tumor of Tendon Sheath (GCTT) or Cells of Pigmented Villonodular Synovitis (PVNS) Observed after Culture with Addition of Non-Steroidal Anti-Inflammatory Agent It has been reported that PPARγ is a transcription factor indispensable for fat cell differentiation. Therefore, in the same manner as that of Example 3, zaltoprofen was added at a concentration of 400 µM to the cells of giant cell tumor of tendon sheath (GCTT) or cells of pigmented villonodular synovitis (PVNS), and differentiation into fat cells was analyzed (FIGS. 30 and 31). As a result, it was successfully confirmed that the positive images obtained with HCS LipidTOX Green increased in the zaltoprofen-added cells compared with the control.

Therefore, it was verified that zaltoprofen enables prophylactic treatment or therapeutic treatment of giant cell tumor of tendon sheath (GCTT) and pigmented villonodular synovitis (PVNS) by differentiating cells of giant cell tumor of tendon sheath (GCTT) and pigmented villonodular synovitis (PVNS) into fat cells, and thereby making the tumor disappear.

Figure 32:
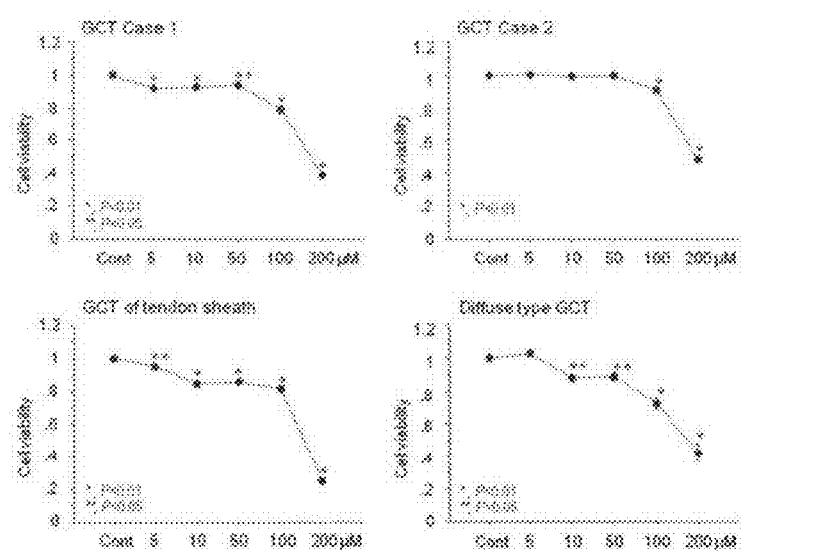
FIG. 32 Graphs showing results of suppression of proliferation of cultured cells derived from giant cell tumor of bone (GCTB), cultured cells derived from giant cell tumor of tendon sheath (GCTT), and cultured cells derived from pigmented villonodular synovitis (PVNS) cultured in a pioglitazone-containing medium. The indications of CT case 1 and GCT case 2 represent cultured cells of giant cell tumor of bone from different origins. The horizontal axes represent the concentration of pioglitazone, and the vertical axes represent the live cell count measured on the basis of absorbance at 450 nm using Cell Counting Kit-8 (CCK-8, Dojindo) using a tetrazolium salt WST-8 as a chromophoric substrate. The numerals on the right side of P< indicate the significance levels obtained as a result of statistical analysis.

Example 11: Analysis of Suppression of Cell Proliferation of Cultured Cells of Human Giant Cell Tumor of Bone (GCTB), Cultured Cells of Giant Cell Tumor of Tendon Sheath (GCTT), and Cultured Cells of Pigmented Villonodular Synovitis (PVNS) Observed after Culture with Addition of Pioglitazone In the same manner as that of Example 1, the GCTB cultured cells (case 1, case 2), the cells of giant cell tumor of tendon sheath (GCTT), or the cells of pigmented villonodular synovitis (PVNS) were cultured, and then pioglitazone, which is a thiazolidine derivative, was added at various concentrations, and absorbance was measured at 450 nm (FIG. 32). As a result, it was successfully confirmed that the proliferation of cells was suppressed in a pioglitazone concentration-dependent manner.

Therefore, it was verified that pioglitazone is useful for prophylactic treatment or therapeutic treatment of giant cell tumor of bone (GCTB), giant cell tumor of tendon sheath (GCTT), and pigmented villonodular synovitis (PVNS).

Figure 33:
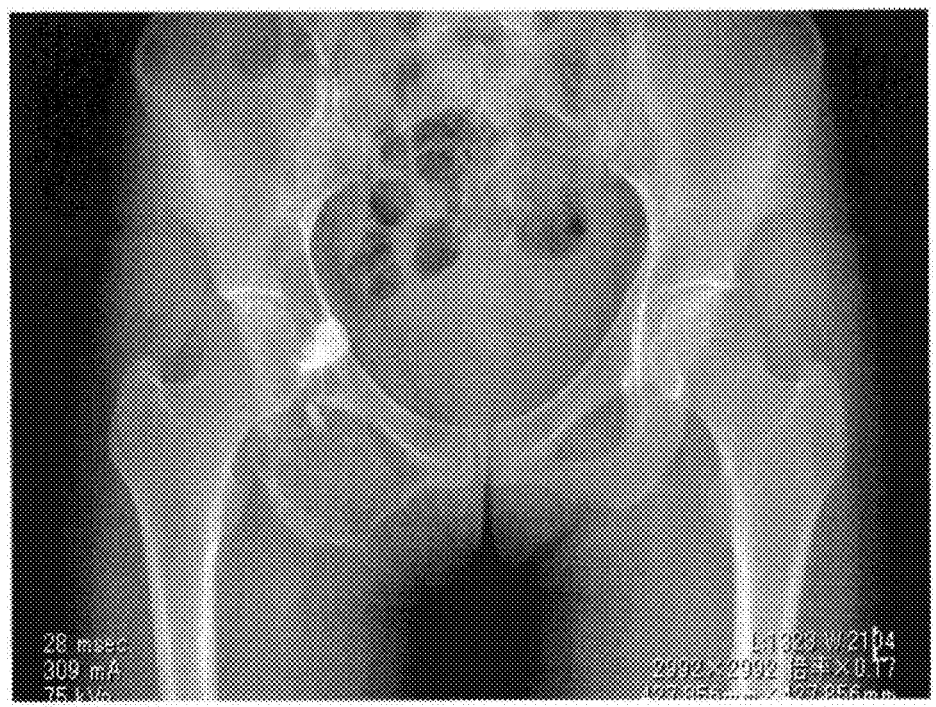
FIG. 33 A photograph showing an X-ray image of the pelvic part of a patient with recurrence of giant cell tumor of bone (GCTB) in the pelvic part obtained before the administration of zaltoprofen. This case is the same as the case a mentioned in the table of FIG. 79.
Figure 34:
FIG. 34 A photograph showing an MRI image of the pelvic part of a patient with recurrence of giant cell tumor of bone (GCTB) in the pelvic part obtained before the administration of zaltoprofen. This case is the same as the case a mentioned in the table of FIG. 79.
Figure 35:
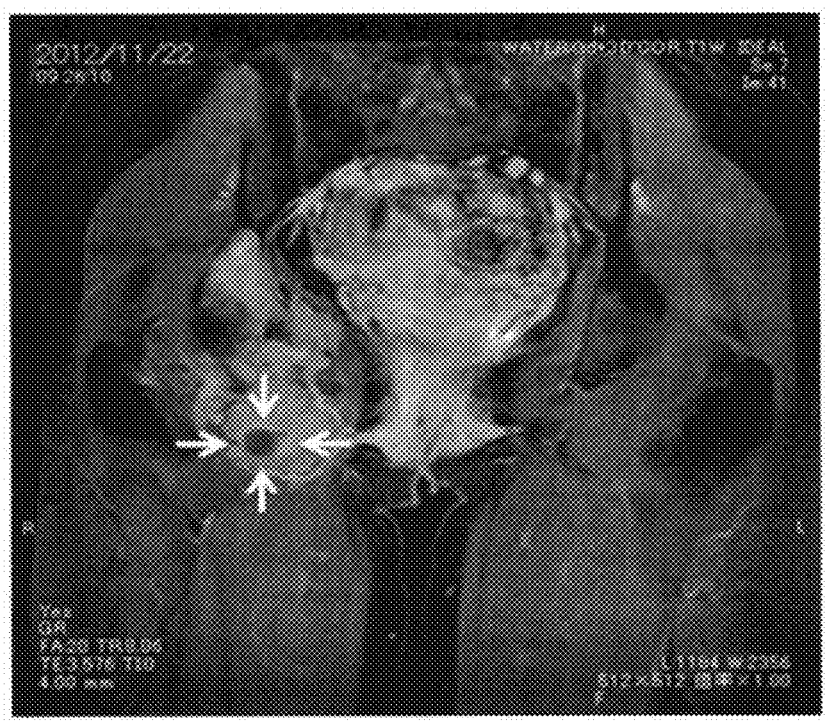
FIG. 35 A photograph showing an MRI image of the pelvic part of a patient with recurrence of giant cell tumor of bone (GCTB) in the pelvic part obtained after two months of the administration of zaltoprofen. The arrows indicate a tumor necrosis region. This case is the same as the case a mentioned in the table of FIG. 79.
Figure 36:
FIG. 36 A photograph showing an MRI image of the pelvic part of a patient with recurrence of giant cell tumor of bone (GCTB) in the pelvic part obtained after four months of the administration of zaltoprofen. The arrows indicate a tumor necrosis region. This case is the same as the case a mentioned in the table of FIG. 79.
Figure 37:
FIG. 37 A photograph showing a sagittal MRI image of the right knee part of a patient with recurrence of pigmented villonodular synovitis (PVNS) in the right knee part obtained before the administration of zaltoprofen. This case is the same as the case i mentioned in the table of FIG. 86.
Figure 38:
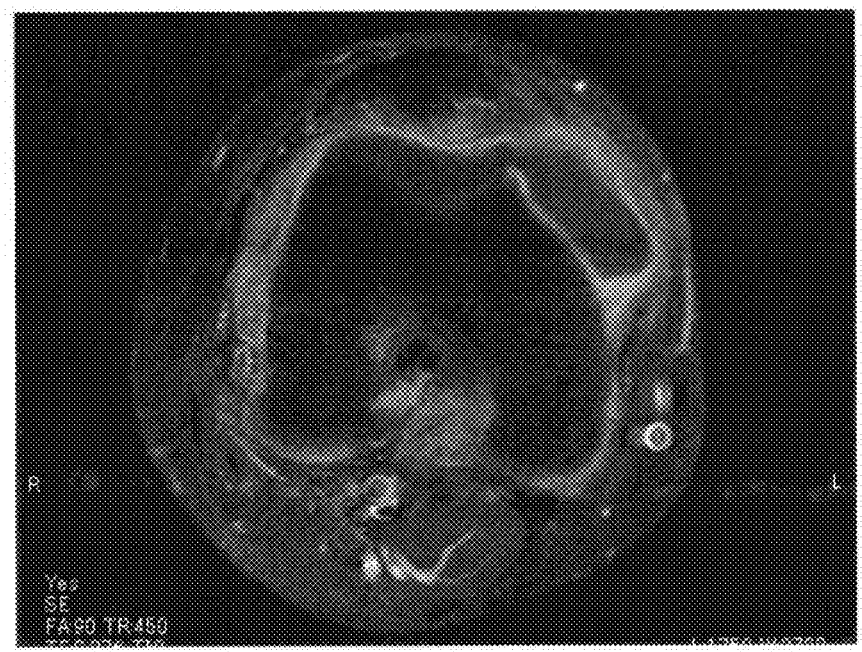
FIG. 38 A photograph showing a transversal MRI image of the right knee part of a patient with recurrence of pigmented villonodular synovitis (PVNS) in the right knee part obtained before the administration of zaltoprofen. This case is the same as the case i mentioned in the table of FIG. 86.
Figure 39:
FIG. 39 A photograph showing a sagittal MRI image of the right knee part of a patient with recurrence of pigmented villonodular synovitis (PVNS) in the right knee part obtained after three months of the administration of zaltoprofen. The arrows indicate attenuation of the MRI imaging effect. This case is the same as the case i mentioned in the table of FIG. 86.
Figure 40:
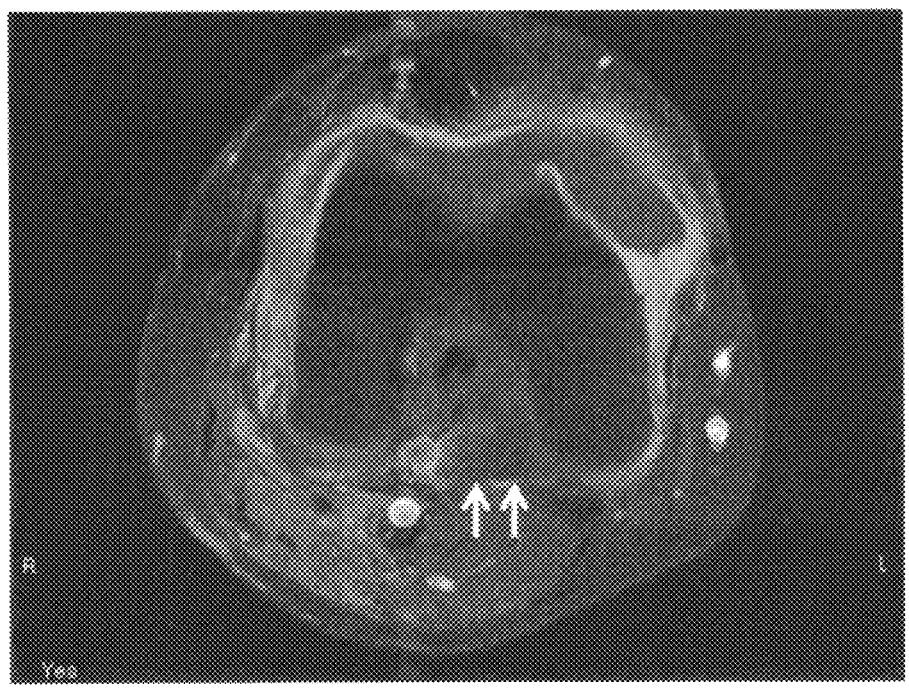
FIG. 40 A photograph showing a transversal MRI image of the right knee part of a patient with recurrence of pigmented villonodular synovitis (PVNS) in the right knee part obtained after three months of the administration of zaltoprofen. The arrows indicate attenuation of the MRI imaging effect. This case is the same as the case i mentioned in the table of FIG. 86.
Figure 41:
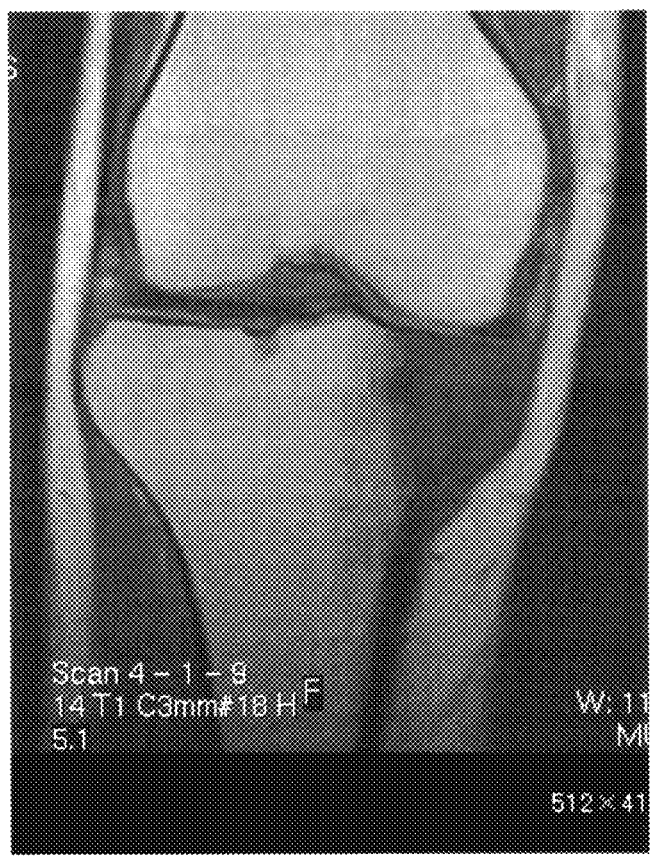
FIG. 41 A photograph showing a coronal MRI image of the right knee part of a patient with recurrence of pigmented villonodular synovitis (PVNS) in the right knee part obtained before the administration of zaltoprofen. This case is the same as the case b mentioned in the table of FIG. 86.
Figure 42:
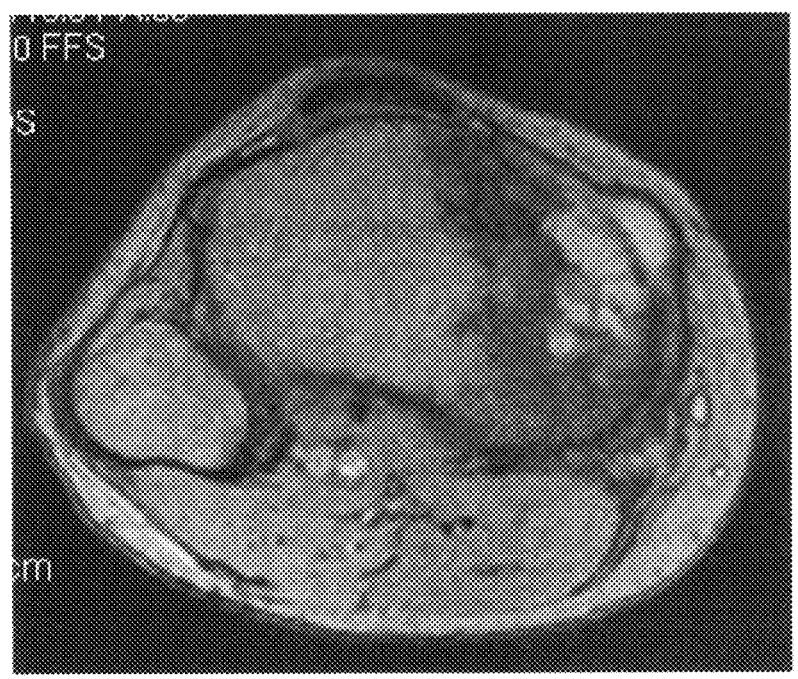
FIG. 42 A photograph showing a transversal MRI image of the right knee part of a patient with recurrence of pigmented villonodular synovitis (PVNS) in the right knee part obtained before the administration of zaltoprofen. This case is the same as the case b mentioned in the table of FIG. 86.
Figure 43:
FIG. 43 A photograph showing a coronal MRI image of the right knee part of a patient with recurrence of pigmented villonodular synovitis (PVNS) in the right knee part obtained after two months of the administration of zaltoprofen. The arrows indicate shrinkage of tumor. This case is the same as the case b mentioned in the table of FIG. 86.
Figure 44:
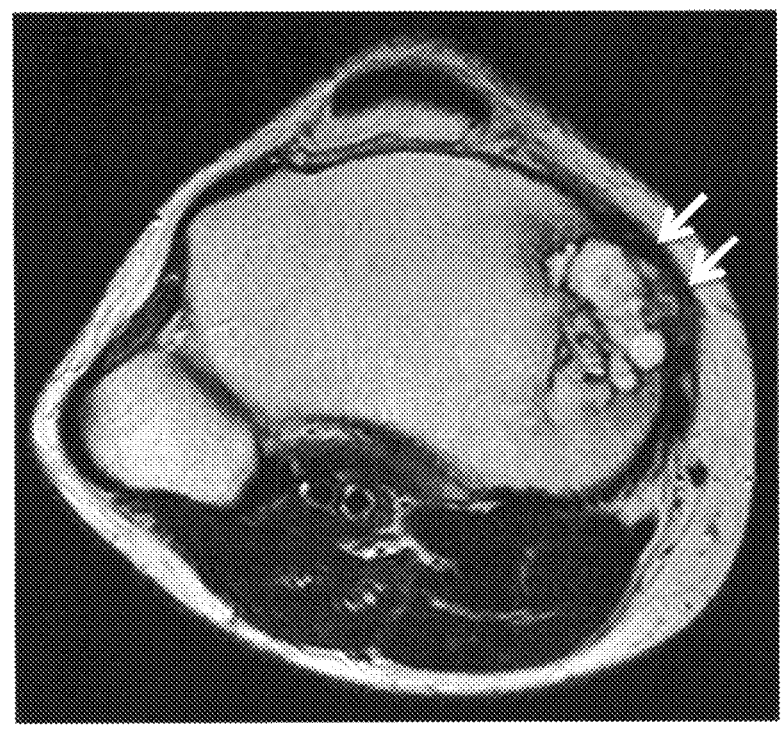
FIG. 44 A photograph showing a transversal MRI image of the right knee part of a patient with recurrence of pigmented villonodular synovitis (PVNS) in the right knee part obtained after two months of the administration of zaltoprofen. The arrows indicate shrinkage of tumor. This case is the same as the case b mentioned in the table of FIG. 86.

Example 12: Analysis of MRI Images of Patient with Giant Cell Tumor of Bone (GCTB), Patient with Giant Cell Tumor of Tendon Sheath (GCTT), or Patient with Pigmented Villonodular Synovitis (PVNS) Administered with Zaltoprofen Soleton Tablet 80 (generic name: zaltoprofen, 80 mg, Nippon Chemiphar) was administered to a patient with giant cell tumor of bone (GCTB), patient with giant cell tumor of tendon sheath (GCTT), or patient with pigmented villonodular synovitis (PVNS) at a dose of 3 tablets per day (one tablet was administered in the morning, at noon, and in the evening), and the tumor size was evaluated by MRI every several months. As a typical case, in a case of recurrence of giant cell tumor of bone (GCTB) in the pelvic part (34 years old, female, FIGS. 33 and 34), gradual shrinkage of the tumor could be confirmed after two months (FIG. 35) and four months (FIG. 36). Further, in a case of recurrence of pigmented villonodular synovitis (PVNS) in the right knee (26 years old, female, FIGS. 37 and 38), attenuation of MRI imaging effect was successfully observed after three months (FIGS. 39 and 40), and improvement was observed for pain and knee-joint excursion. Furthermore, in another case of recurrence of pigmented villonodular synovitis (PVNS) in the right knee (38 years old, female, FIGS. 41 and 42), shrinkage of tumor could be confirmed, and improvement of pain could be observed after two months (FIGS. 43 and 44).

Therefore, it was verified in human that zaltoprofen is useful for prophylactic treatment or therapeutic treatment of giant cell tumor of hone (GCTB), giant cell tumor of tendon sheath (GCTT), and pigmented villonodular synovitis (PVNS).

Figure 45:
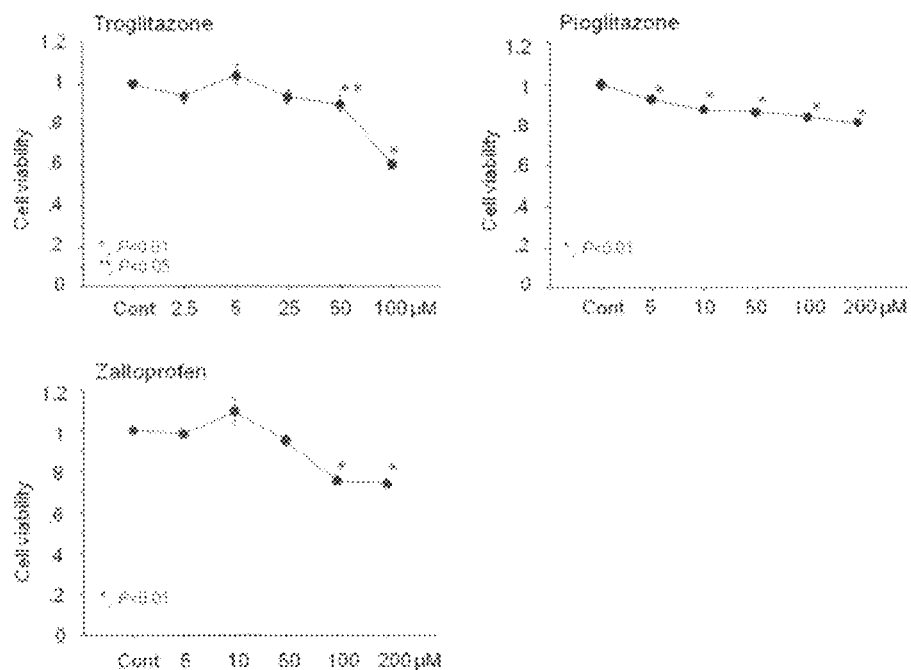
FIG. 45 Graphs showing results of suppression of proliferation of cells of a chondrosarcoma-derived cell line (H-EMC-SS) cultured in a zaltoprofen, troglitazone, or pioglitazone-containing medium. The cell proliferation was measured by using Cell Counting Kit-8 (CCK-8, Dojindo) using a tetrazolium salt WST-8 as a chromophoric substrate. The concentrations indicated under the horizontal axes are the concentrations of the drugs, and the vertical axis represent the live cell count measured on the basis of absorbance at 450 nm. The numerals on the right side of P< indicate the significance levels obtained as a result of statistical analysis.

Example 13: Analysis of Suppression of Cell Proliferation and Apoptosis of Cells of Human Chondrosarcoma-Derived Cell Line (H-EMC-SS) Observed after Culture with Addition of Non-Steroidal Anti-Inflammatory Agent or Thiazolidine Derivative In the same manner as that of Example 1, cells of the chondrosarcoma cell line were cultured, troglitazone, pioglitazone, or zaltoprofen was added at various concentrations, and absorbance was measured (FIG. 45). The H-EMC-SS cells were obtained from the Riken BioResource Center. As a result, it was successfully confirmed that the cell proliferation was suppressed in a troglitazone, pioglitazone, or zaltoprofen concentration-dependent manner.

Therefore, it was verified that troglitazone, pioglitazone, and zaltoprofen are useful for prophylactic treatment or therapeutic treatment of chondrosarcoma.

Figure 46:
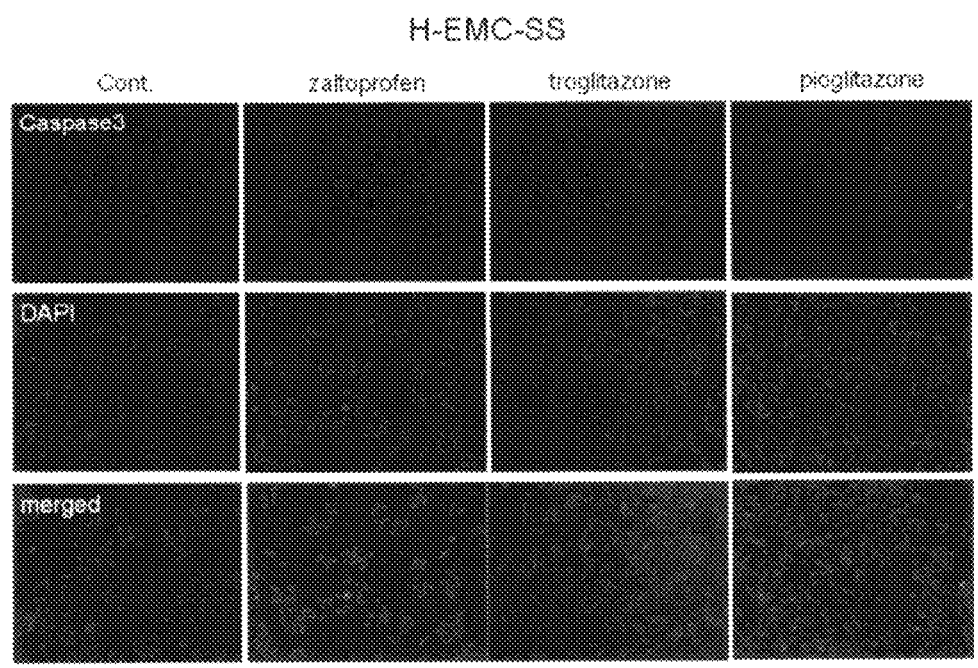
FIG. 46 Photographs showing results of caspase 3 staining of cells of a chondrosarcoma-derived cell line (H-EMC-SS) cultured in a zaltoprofen, troglitazone, or pioglitazone-containing medium. The indication of DAPI means that the results are results of nuclear staining with DAPI, which is a fluorescent dye.
Figure 47:
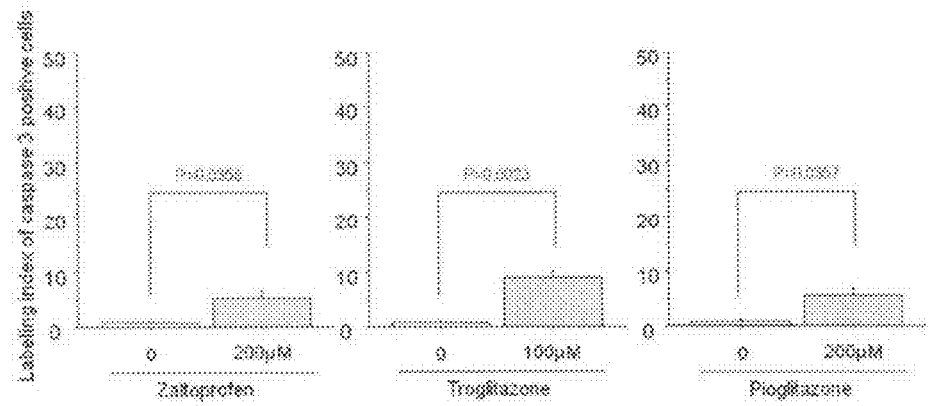
FIG. 47 Graphs showing ratios of caspase 3-positive cells in cells of a chondrosarcoma-derived cell line (H-EMC-SS) cultured in a zaltoprofen, troglitazone, or pioglitazone-containing medium. The vertical axes represent the ratio of caspase 3-positive cells, and the concentrations indicated under the horizontal axes are the concentrations of the drugs. The numerals on the right side of P indicate the significance levels obtained as a result of statistical analysis.

Further, in the same manner as that of Example 1, cells of the chondrosarcoma cell line were subjected to caspase 3 staining, and presence or absence of apoptosis was analyzed (FIGS. 46 and 47). As a result, it was successfully confirmed that the caspase 3-positive ratio increased in the cells added with zaltoprofen at a concentration of 200 µM, troglitazone at a concentration of 100 µM, or pioglitazone at a concentration of 200 µM, compared with the control.

Therefore, it was verified that suppression of proliferation of chondrosarcoma by troglitazone, pioglitazone, and zaltoprofen is based on cell death caused by apoptosis.

Figure 48:
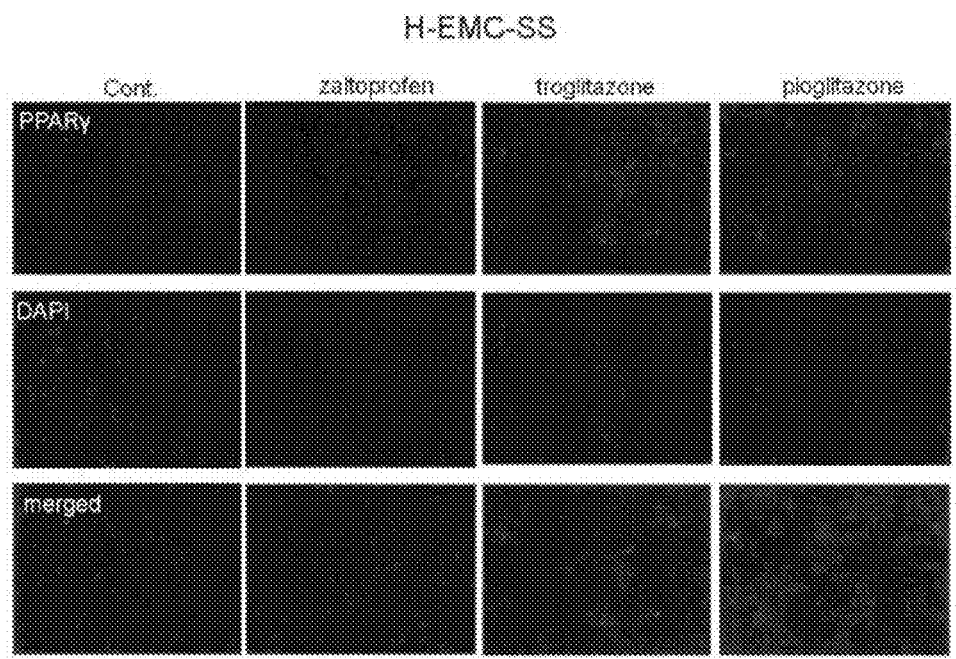
FIG. 48 Photographs showing results of PPARγ staining of cells of a chondrosarcoma-derived cell line (H-EMC-SS) cultured in a zaltoprofen, troglitazone, or pioglitazone-containing medium. The indication of DAPI means that the results are results of nuclear staining with DAPI, which is a fluorescent dye.
Figure 49:
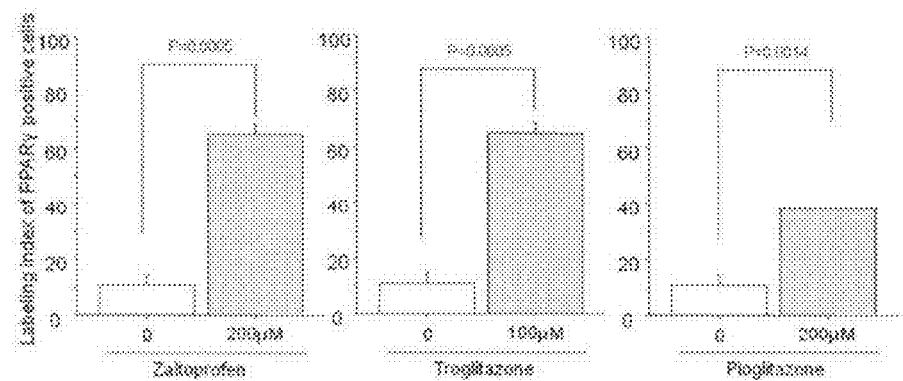
FIG. 49 Graphs showing ratios of PPARγ-positive cells in cells of a chondrosarcoma-derived cell line (H-EMC-SS) cultured in a zaltoprofen, troglitazone, or pioglitazone-containing medium. The vertical axes represent the ratio of PPARγ-positive cells, and the concentrations indicated under the horizontal axes are the concentrations of the drugs. The numerals on the right side of P indicate the significance levels obtained as a result of statistical analysis.

Example 14: PPARγ Immunostaining of Cells of Chondrosarcoma Cell Line (H-EMC-SS) Performed after Culture with Addition of Non-Steroidal Anti-Inflammatory Agent or Thiazolidine Derivative In the same manner as that of Example 2, to cells of the chondrosarcoma cell line was added zaltoprofen at a concentration of 200 μM, troglitazone at a concentration of 100 μM, or pioglitazone at a concentration of 200 μM, and the PPARγ-positive images were observed (FIGS. 48 and 49). As a result, expression of PPARγ could be confirmed in the zaltoprofen, troglitazone, or pioglitazone-added cells.

Therefore, it was verified that zaltoprofen, troglitazone, and pioglitazone enable prophylactic treatment or therapeutic treatment of chondrosarcoma on the basis of promotion of expression of PPARγ.

Example 15: Analysis of Cell Proliferation-Suppressing Effect of Various Thiazolidinedione Derivatives and Various Non-Steroidal Anti-Inflammatory Agents for Cells of Human Giant Cell Tumor of Bone (GCTB), Cells of Human Giant Cell Tumor of Tendon Sheath (GCTT), Cells of Human Pigmented Villonodular Synovitis (PVNS), and Cells of Human Chondrosarcoma Cell Lines In the same manners as those of Examples 1, 6, 8, 11, and 13, cell proliferation-suppressing effects of various kinds of thiazolidinedione derivatives and non-steroidal anti-inflammatory agents were analyzed. The analysis was performed in the same manners as those of Examples 1 and 6 for cells of giant cell tumor of bone (GCT-1, GCT-2), in the same manner as that of Example 8 for cells of giant cell tumor of tendon sheath and cells of pigmented villonodular synovitis, and in the same manner as that of Example 13 for cells of chondrosarcoma cell lines (H-EMC-SS, SW1353), and absorbance was measured at 450 nm. The H-EMC-SS cells were obtained from the Riken BioResource Center. As the SW1353 cells, those obtained from ATCC were used. As a result, the following results were obtained.

Figure 50:
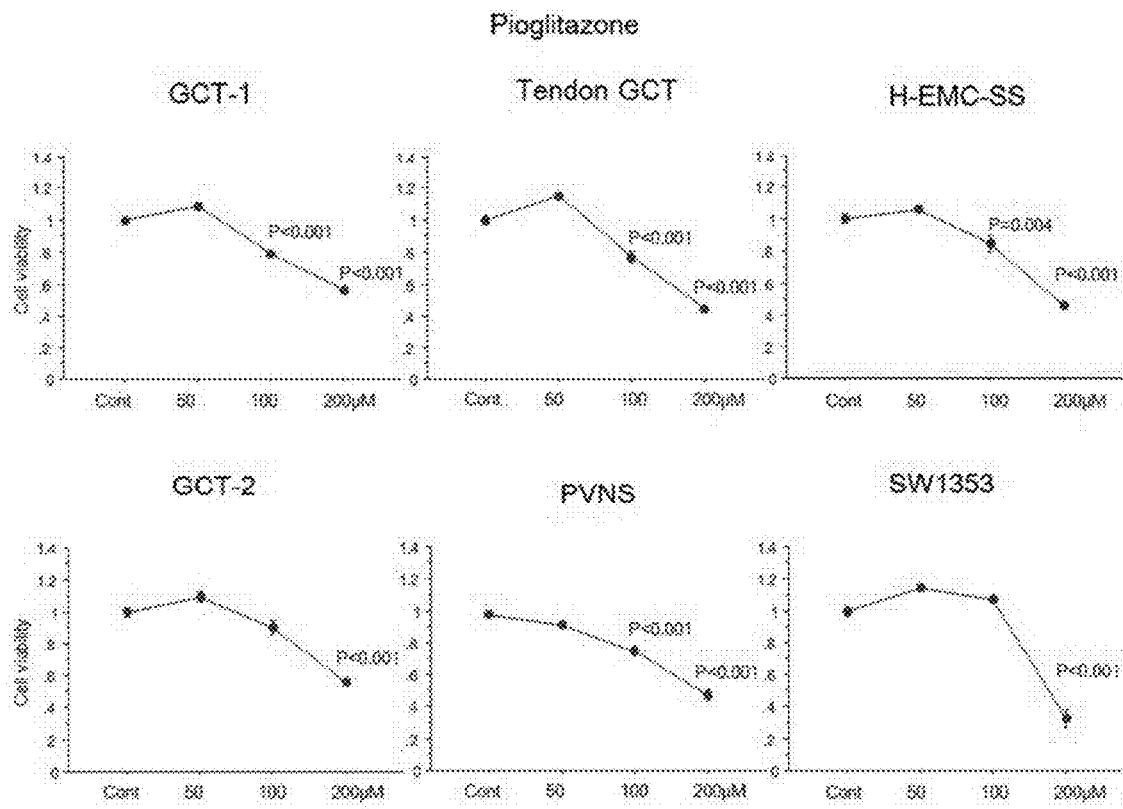
FIG. 50 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a pioglitazone-containing, medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that pioglitazone (50 μm, 100 μm, and 200 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 50).

Figure 51:
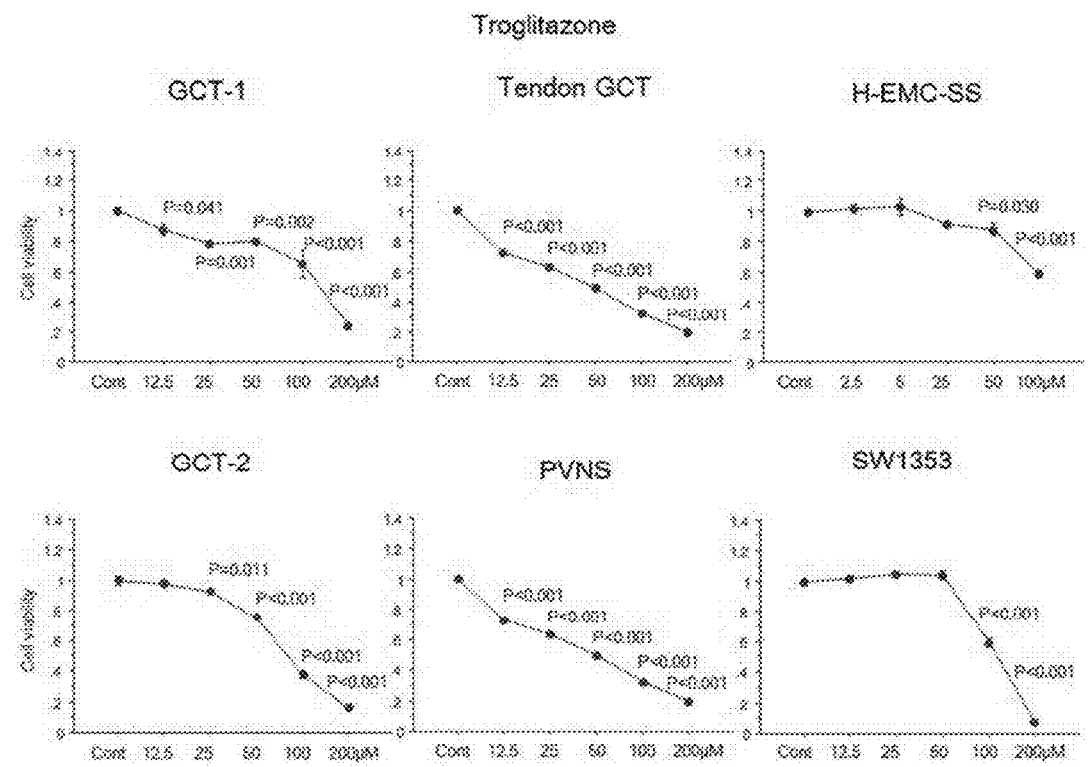
FIG. 51 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a troglitazone-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that troglitazone (12.5 μm, 25 μm, 50 μm, 100 μm, and 200 μm) suppressed proliferation of cells of giant cell tumor of bone (GCT-1, GCT-2), cells of giant cell tumor of tendon sheath, cells of pigmented villonodular synovitis, and cells of chondrosarcoma cell lines (H-EMC-SS, SW1353) in a concentration-dependent manner (FIG. 51).

Figure 52:
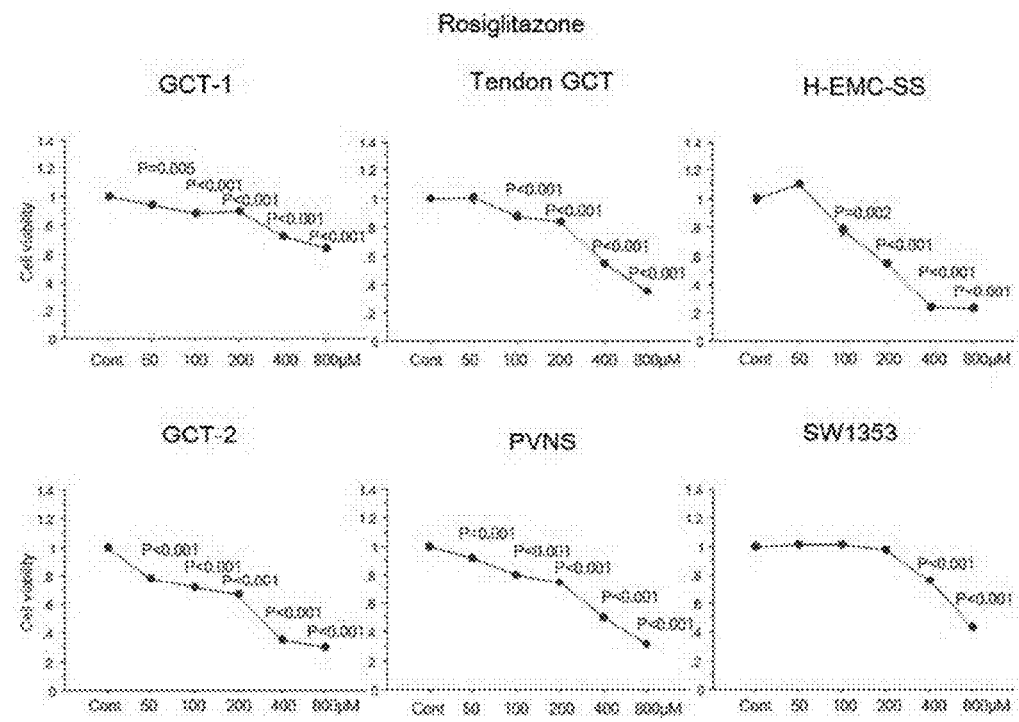
FIG. 52 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a rosiglitazone-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that rosiglitazone (50 μm, 100 μm, 200 μm, 400 μm, and 800 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 52).

Figure 53:
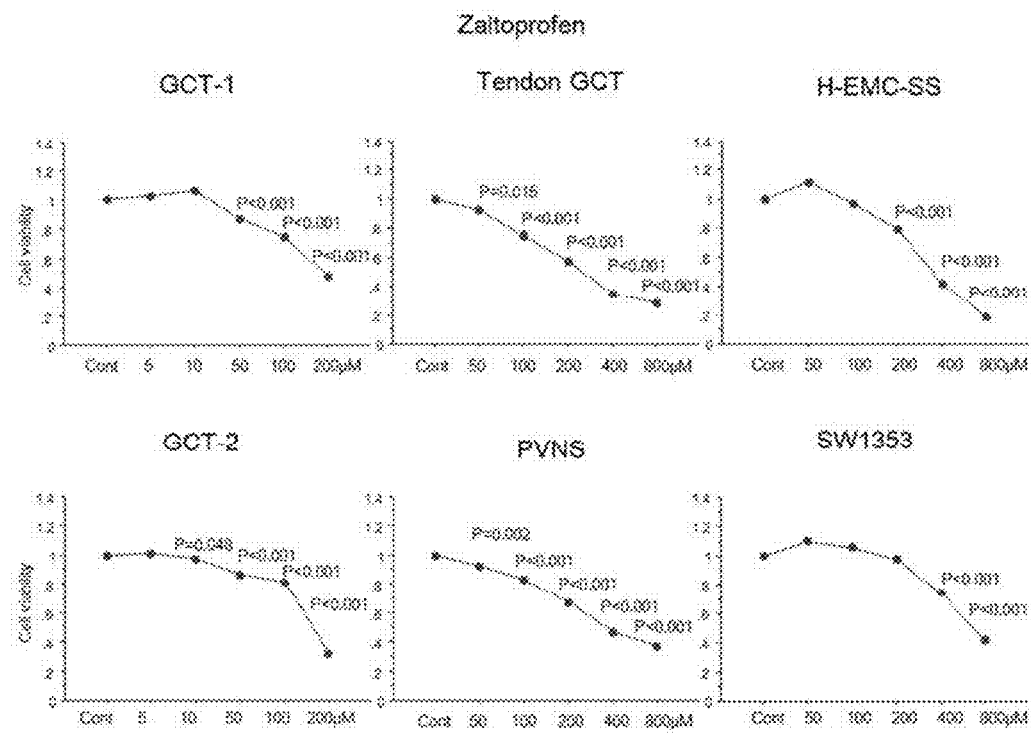
FIG. 53 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a zaltoprofen-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that zaltoprofen (5 μm, 10 μm, 50 μm, 100 μm, and 200 μm for cells of giant cell tumor of bone, 50 μm, 100 μm, 200 μm, 400 μm, and 800 μm for cells of giant cell tumor of tendon sheath, cells of pigmented villonodular synovitis, and cells of chondrosarcoma cell lines) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 53).

Figure 54:
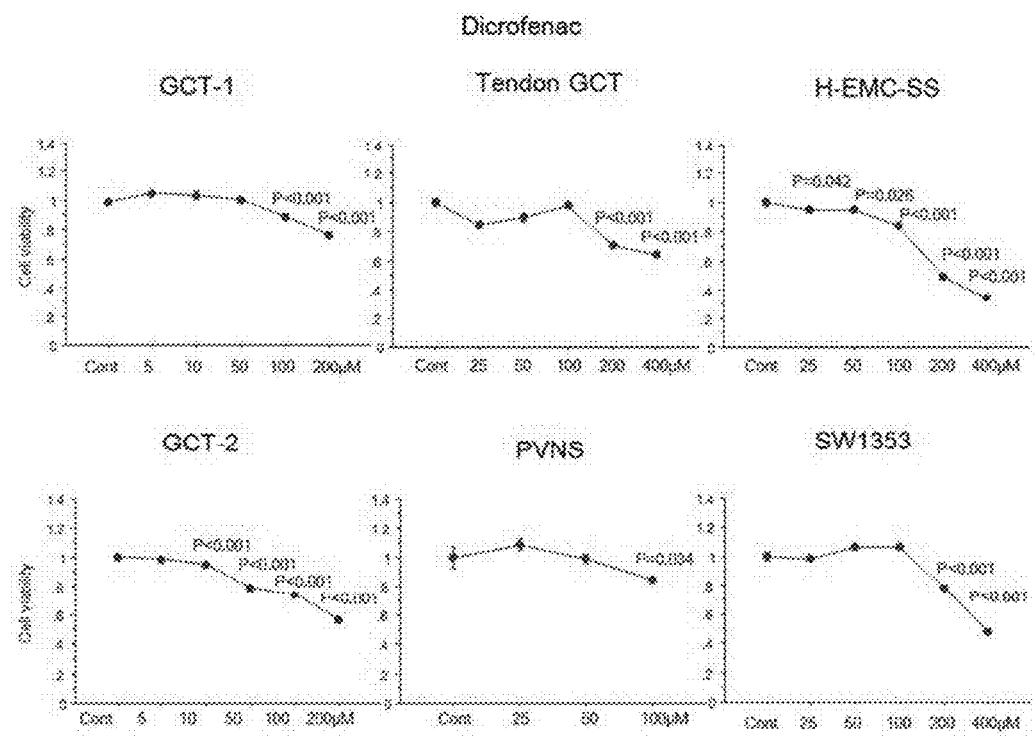
FIG. 54 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a diclofenac-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that diclofenac (5 μm, 10 μm, 50 μm, 100 μm, and 200 μm for cells of giant cell tumor of bone, 25 μm, 50 μm, and 100 μm for cells of giant cell tumor of tendon sheath (GCTT), 25 μm, 50 μm, 100 μm, 200 μm, and 400 μm for cells of pigmented villonodular synovitis, and cells of chondrosarcoma cell lines) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 54).

Figure 55:
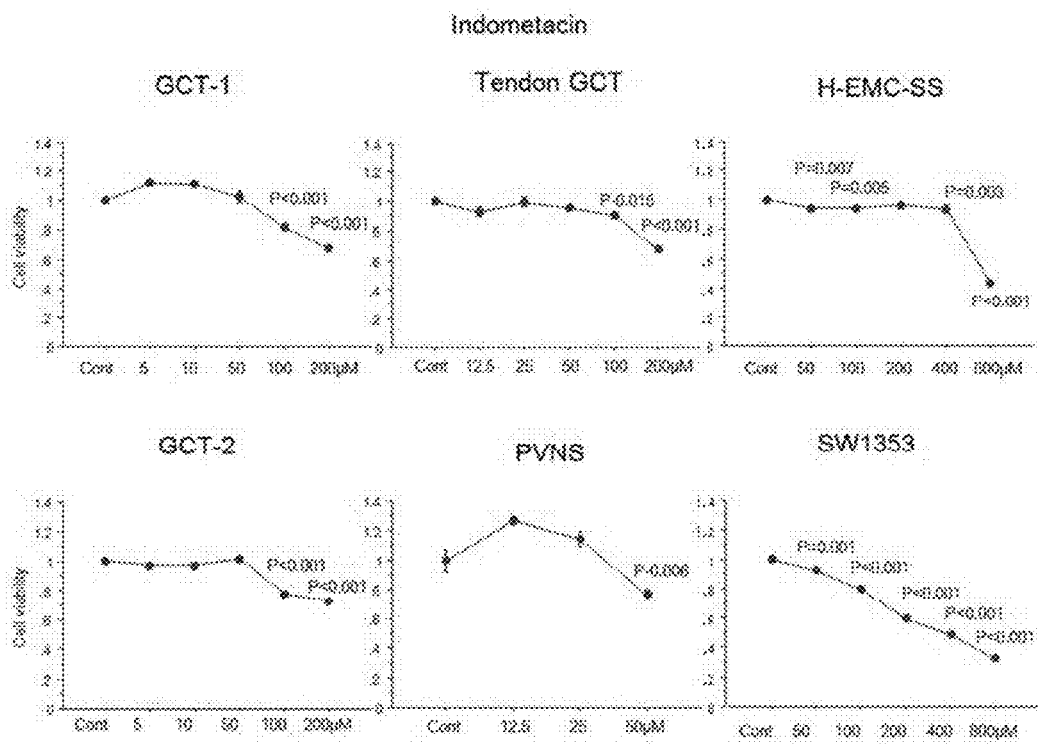
FIG. 55 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in an indomethacin-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that indomethacin (5 μm, 10 μm, 50 μm, 100 μm, and 200 μm for cells of giant cell tumor of bone; 12.5 μm, 25 μm, and 50 μm for cells of giant cell tumor of tendon sheath (GCTT); 12.5 μm, 25 μm, 50 μm, 100 μm, and 200 μm for cells of pigmented villonodular synovitis; 50 μm, 100 μm, 200 μm, 400 μm, and 800 μm for cells of chondrosarcoma cell lines) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 55).

Figure 56:
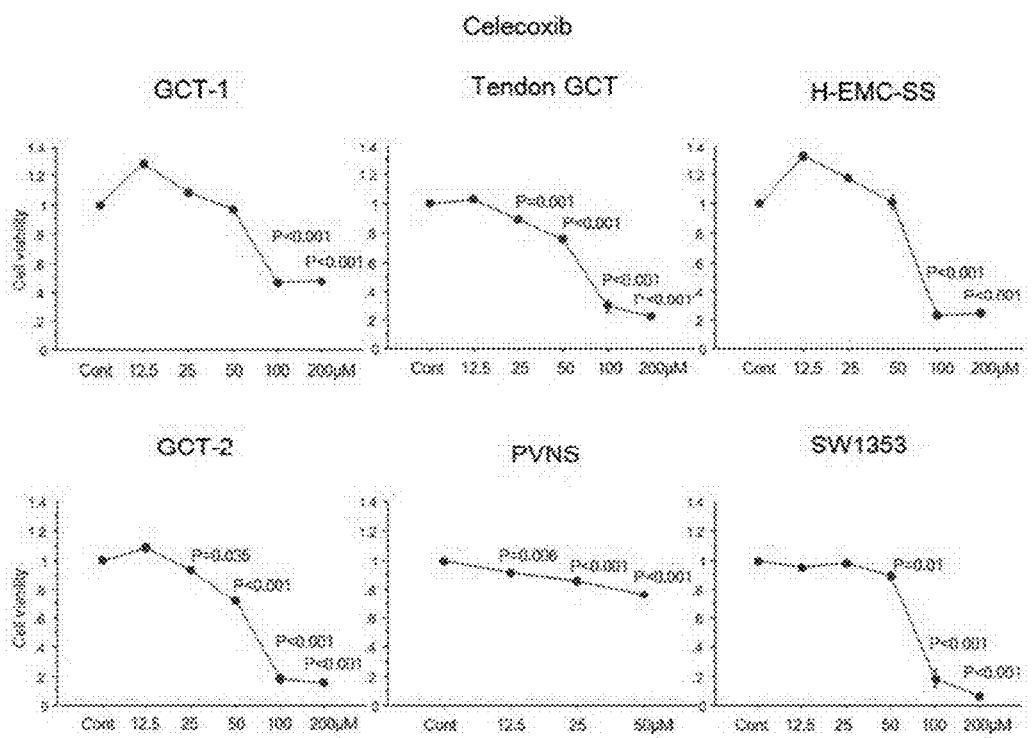
FIG. 56 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a celecoxib-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that celecoxib (12.5 μm, 25 μm, 50 μm, 100 μm, and 200 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 56).

Figure 57:
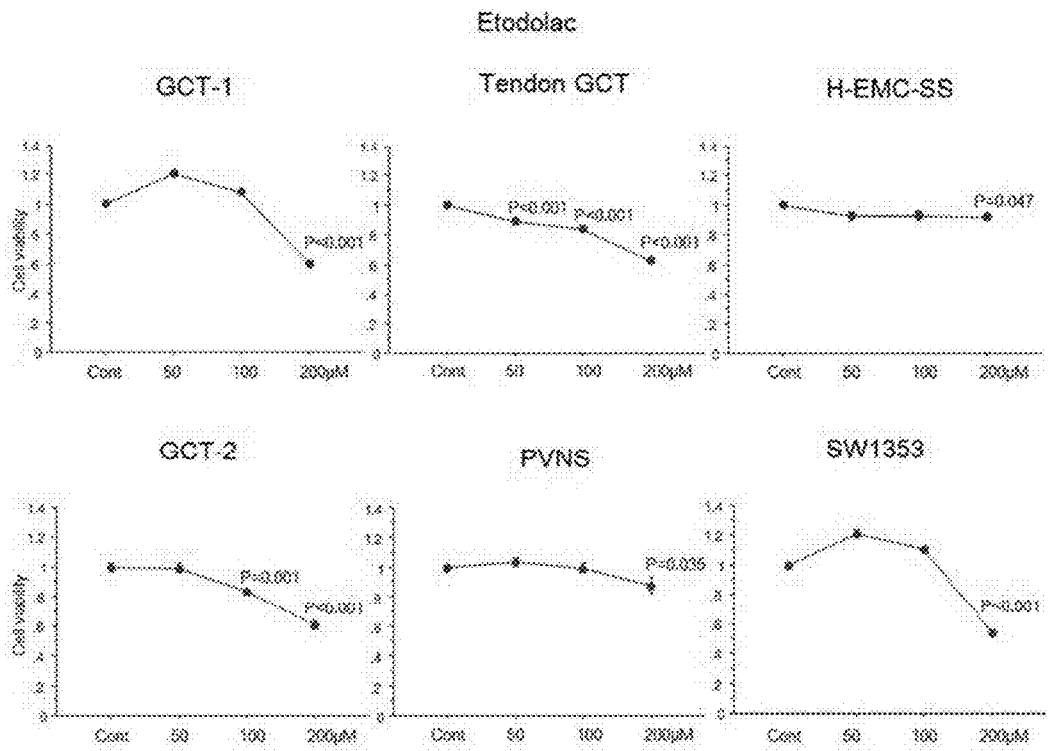
FIG. 57 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (R-EMC-SS, SW1353), which were cultured in an etodolac-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that etodolac (50 μm, 100 μm, and 200 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 57).

Figure 58:
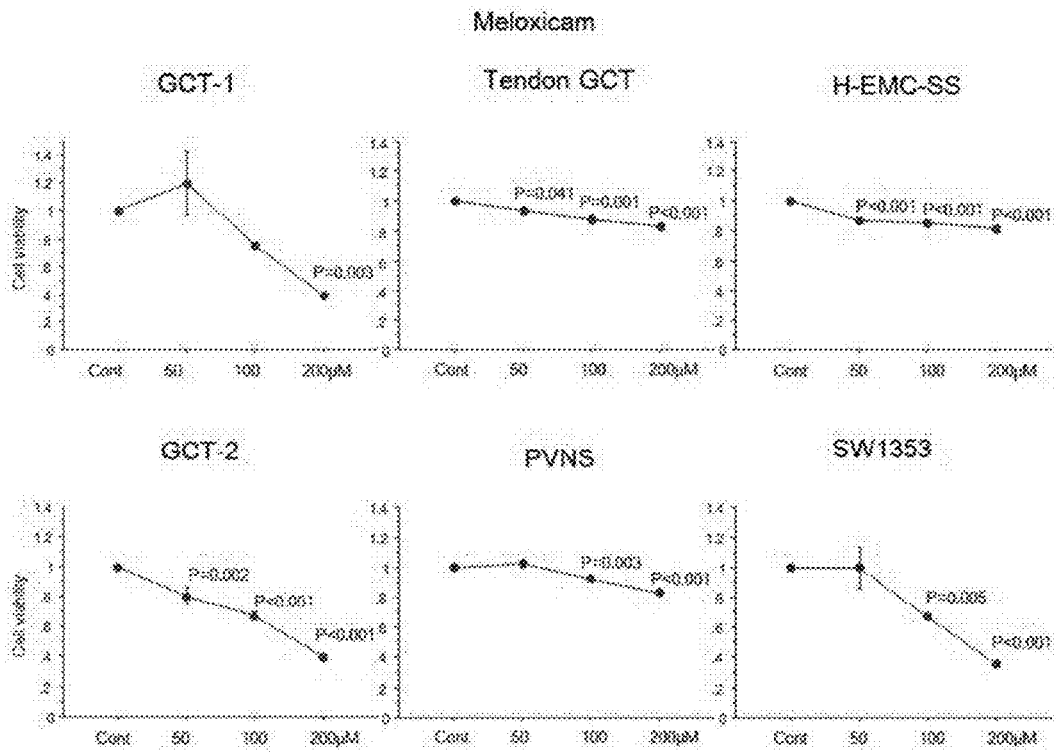
FIG. 58 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a meloxicam-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that meloxicam (50 μm, 100 μm, and 200 μm) suppressed proliferation of cells of giant cell tumor of bone (GCT-1, GCT-2), cells of giant cell tumor of tendon sheath, cells of pigmented villonodular synovitis, and cells of chondrosarcoma cell lines (H-EMC-SS, SW1353) in a concentration-dependent manner (FIG. 58).

Figure 59:
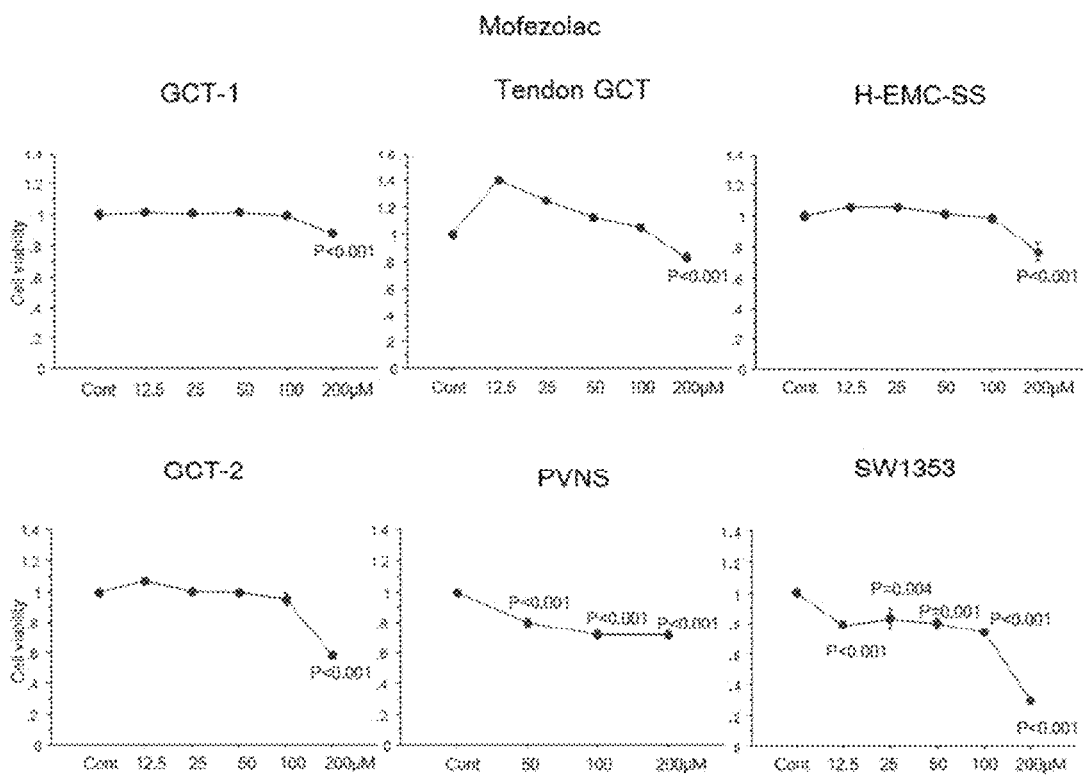
FIG. 59 Graphs showing results of suppression of proliferation of cultured cells of giant cell tumor of bone (GCT-GCT-2), cultured cells of giant cell tumor of tendon sheath (GCTT), cultured cells of pigmented villonodular synovitis, and cells of chondrosarcoma cell lines (H-EMC-SS, SW1353), which were cultured in a mofezolac-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that mofezolac (12.5 μm, 25 μm, 50 μm, 100 μm, and 200 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 59).

Figure 60:
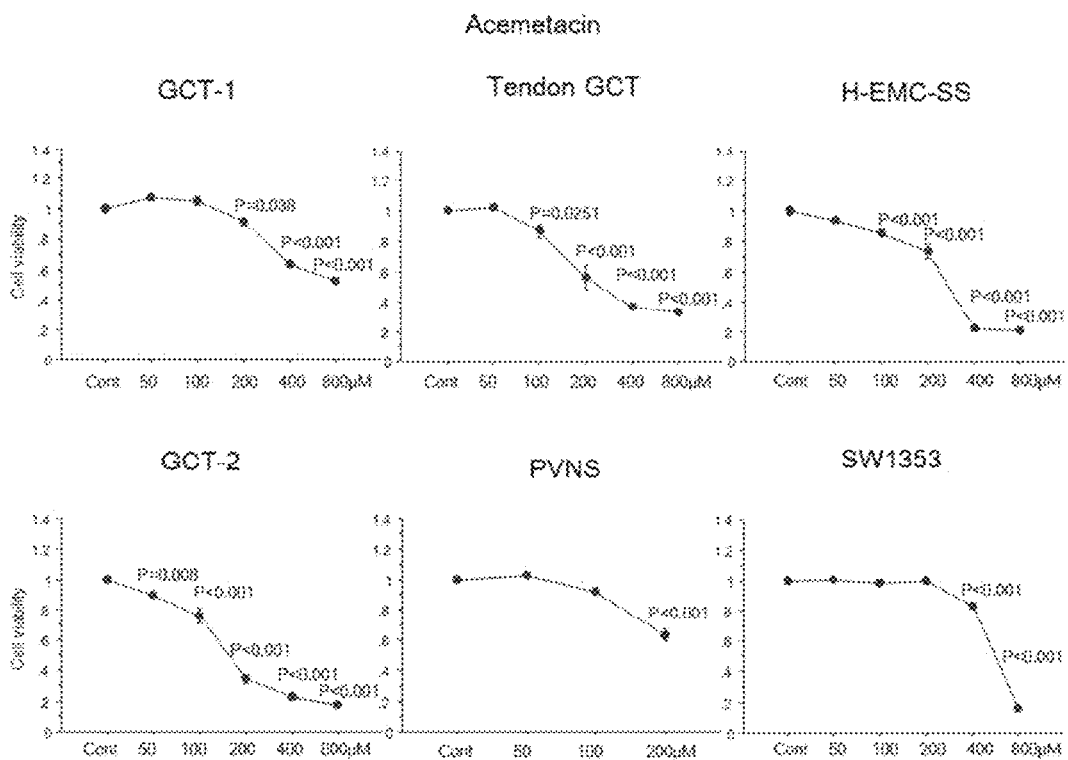
FIG. 60 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in an acemetacin-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that acemetacine (50 μm, 100 μm, 200 μm, 400 μm, and 800 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 60).

Figure 61:
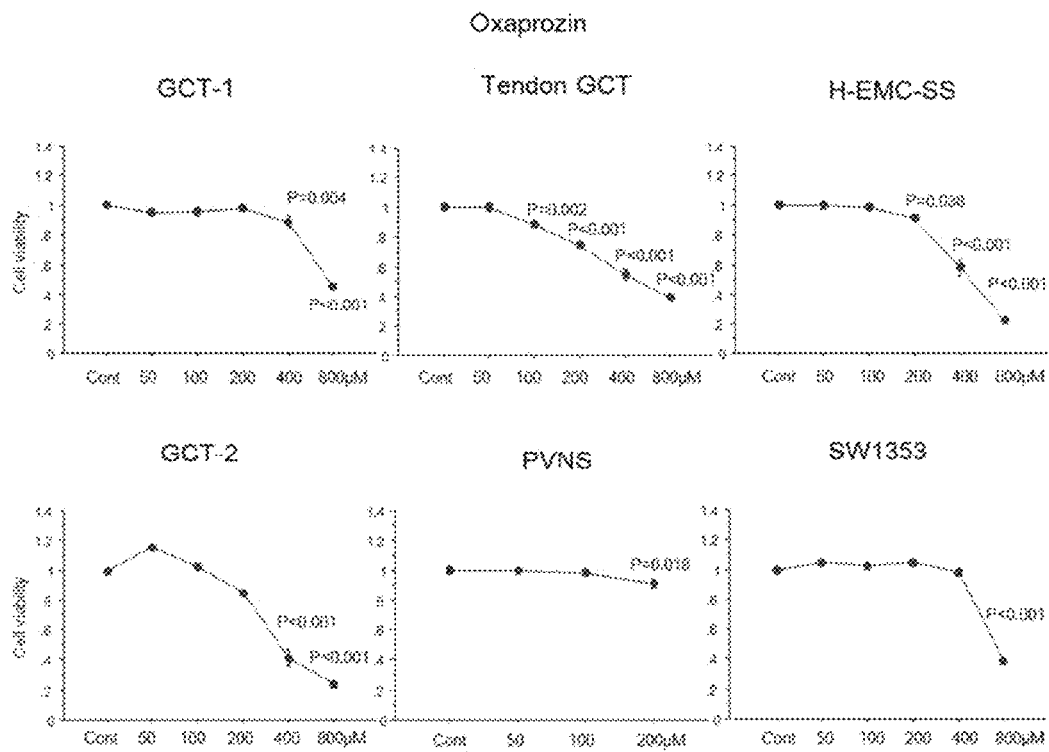
FIG. 61 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in an oxaprozin-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that oxaprozin (50 μm, 100 μm, 200 μm, 400 μm, and 800 μm for cells of giant cell tumor of bone, cells of pigmented villonodular synovitis, and cells of chondrosarcoma cell lines; 50 μm, 100 μm, and 200 μm for cells of giant cell tumor of tendon sheath) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 61). As for the cells of pigmented villonodular synovitis, only slight suppression of the proliferation was observed at the concentration of 200 μm, and this was because the number of usable cells was limited, and the suppression of cell proliferation could not be measured with such high concentrations as 400 μm or higher. However, on the basis of the effects on the cells of giant cell tumor, cells of pigmented villonodular synovitis, and cells of chondrosarcoma cell lines, it was estimated that oxaprozin also suppresses proliferation of cells of giant cell tumor of tendon sheath (GCTT) at a high concentration of 400 μm or higher.

Figure 62:
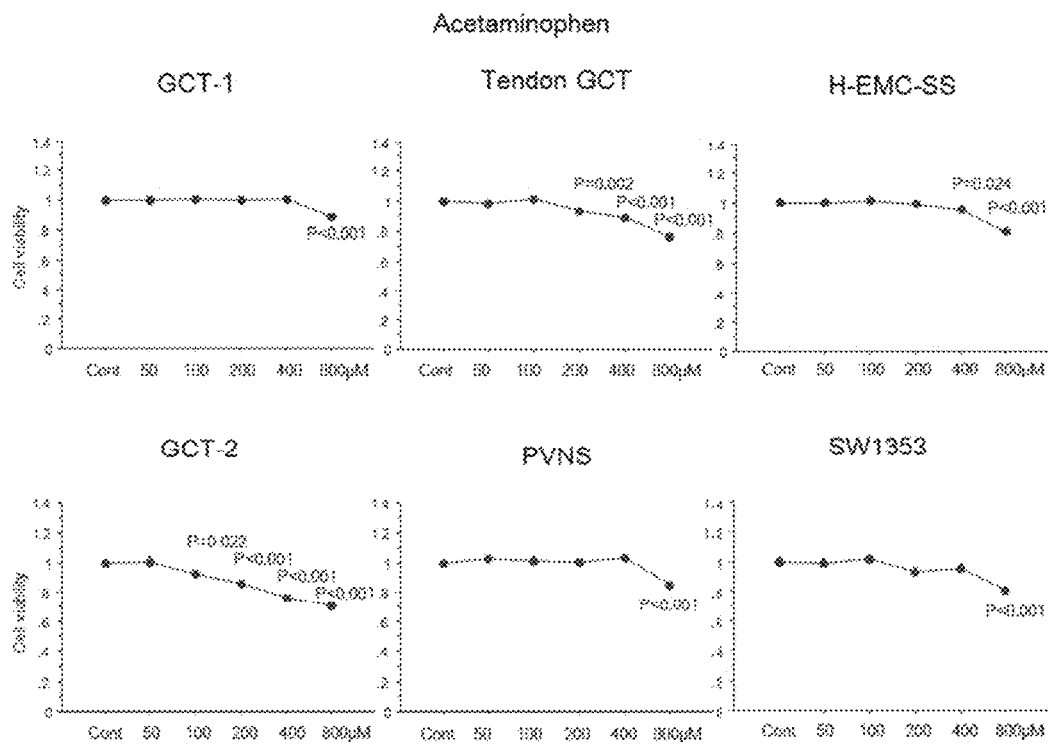
FIG. 62 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in an acetaminophen-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that acetaminophen (50 μm, 100 μm, 200 μm, 400 μm, and 800 μm) suppressed proliferation of cells of giant cell tumor of bone (GCT-1, GCT-2), cells of giant cell tumor of tendon sheath (GM), cells of pigmented villonodular synovitis, and cells of chondrosarcoma cell lines (H-EMC-SS, SW1353) in a concentration-dependent manner (FIG. 62).

Figure 63:
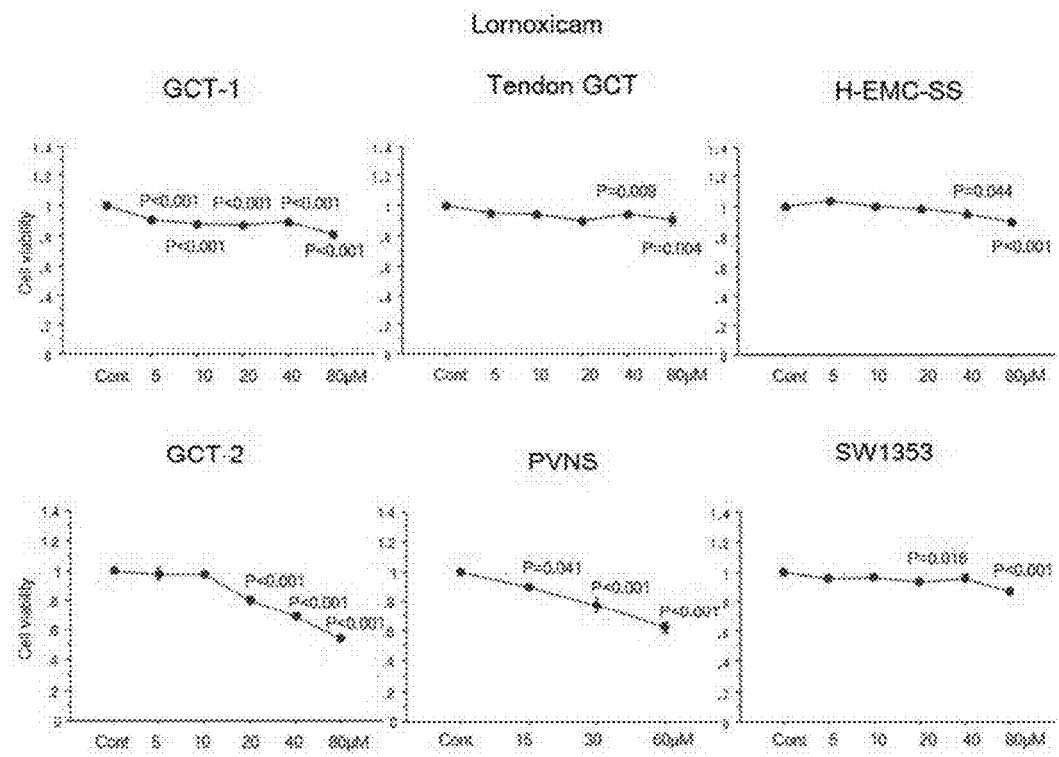
FIG. 63 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a lornoxicam-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that lornoxicam (5 μm, 10 μm, 20 μm, 40 μm, and 80 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 63). The degree of the suppression of cell proliferation apparently seems to be low, but this was because the measurement could be performed for a concentration of only up to 80 μm, which is 1.110 of the drug concentration of acetaminophen, due to the low solubility of lornoxicam in DMSO (dimethyl sulfoxide).

Figure 64:
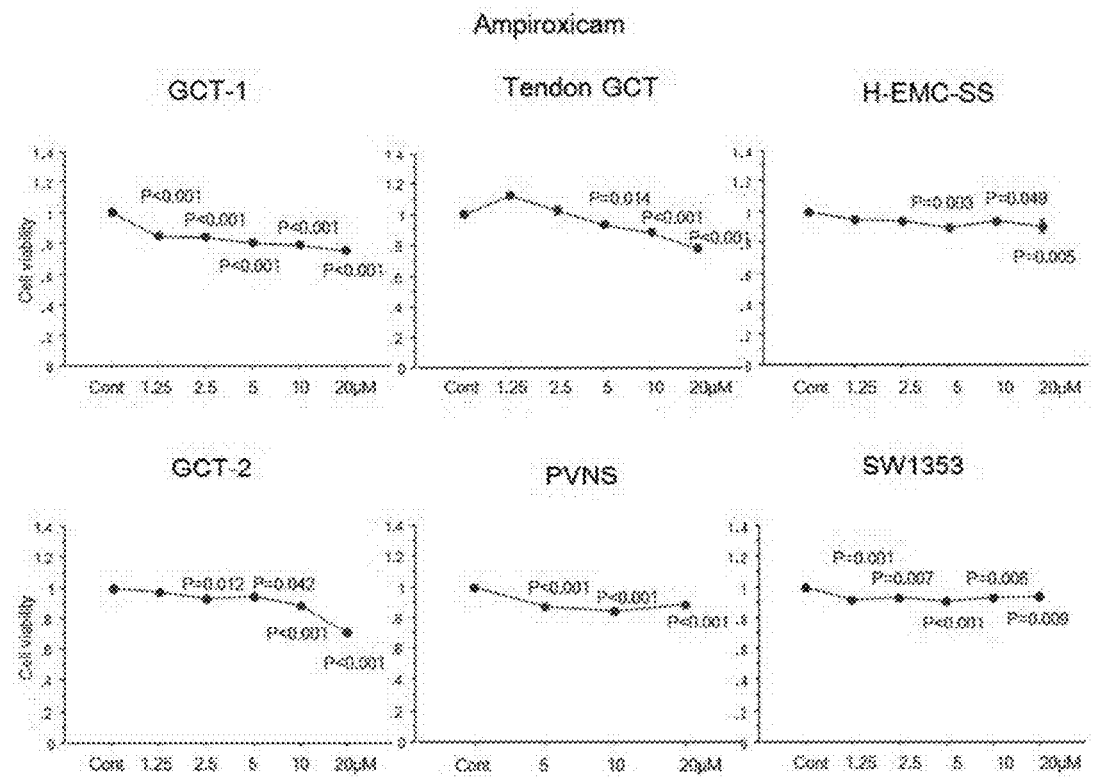
FIG. 64 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in an ampiroxicam-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that ampiroxicam (1.25 μm, 2.5 μm, 5 μm, 10 μm, and 20 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 64). The degree of the suppression of cell proliferation apparently seems to be low, but this was because the measurement could be performed for a concentration of only up to 20 μm at the highest due to the low solubility of the drug in DMSO (dimethyl sulfoxide).

Figure 65:
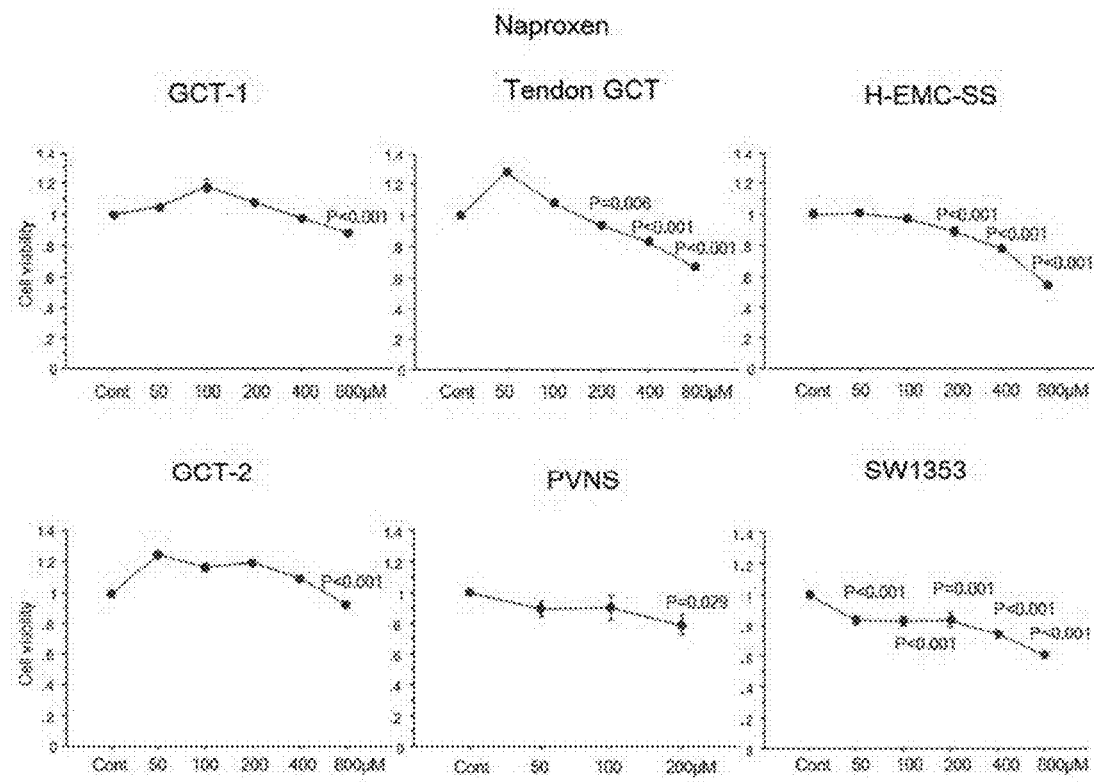
FIG. 65 Graphs showing results of suppression of proliferation of cultured cells of giant cell tumor of bone (GCT-1, GCT-2), cultured cells of giant cell tumor of tendon sheath (GCTT), cultured cells of pigmented villonodular synovitis, and cells of chondrosarcoma cell lines (H-EMC-SS, SW1353), which were cultured in a naproxen-containing medium. The horizontal axes represent the concentration of the drug, and the vertical axes represent the live cell count measured on the basis of absorbance at 450 nm using CCK-8 (Dojindo). The numerals on the right side of P< indicate the significance levels obtained as a result of statistical analysis.

It was successfully confirmed that naproxen (50 μm, 100 μm, 200 μm, 400 μm, and 800 μm) suppressed proliferation of cells of giant cell tumor of bone (GCT-1, GCT-2), cells of giant cell tumor of tendon sheath (GCTT), cells of pigmented villonodular synovitis, and cells of chondrosarcoma cell lines (H-EMC-SS, SW1353) in a concentration-dependent manner (FIG. 65).

Therefore, it was verified that pioglitazone, troglitazone, rosiglitazone, zaltoprofen, diclofenac, indomethacin, celecoxib, etodolac, meloxicam, mofezolac, acemetacin, oxaprozin, acetaminophen, lornoxicam, ampiroxicam, and naproxen are useful for prophylactic treatment or therapeutic treatment of giant cell tumor of bone (GCTB), giant cell tumor of tendon sheath (GCTT), pigmented villonodular synovitis (PVNS), and chondrosarcoma.

Figure 66:
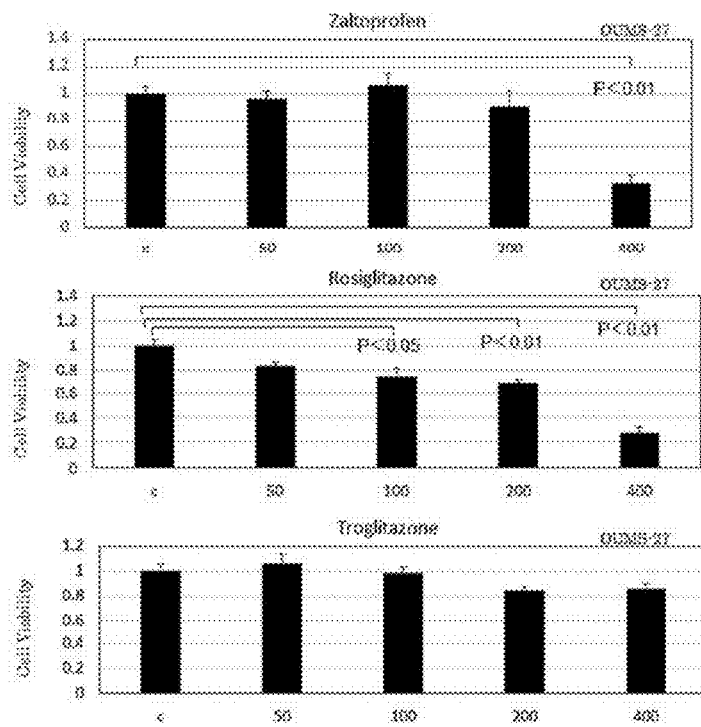
FIG. 66 Graphs showing results of suppression of proliferation of cultured cells of chondrosarcoma (OUMS-27) cultured in a zaltoprofen, rosiglitazone, or troglitazone-containing medium. The concentrations indicated under the horizontal axes are the concentrations of the drugs, and the vertical axes represent the live cell count measured on the basis of absorbance at 450 nm using CCK-8 (Dojindo).

Example 16: Analysis of Suppression of Proliferation of Cells of Human Chondrosarcoma (OUMS-27) Observed after Culture with Addition of Zaltoprofen, Rosiglitazone, or Troglitazone Cells of the human chondrosarcoma cell line, OUMS-27 (purchased from ICRB Cell Bank), were cultured in the same manner as that of Example 1 until they became sub-confluent, zaltoprofen, rosiglitazone, or troglitazone was added to the cells at a concentration of 50, 100, 200, or 400 μM, color development was performed with Cell Counting Kit-8 (CCK-8, Dojindo) 72 hours thereafter, and absorbance was measured at 450 nm further 3 hours thereafter as an index of cell count (FIG. 66). As a result, it was verified that zaltoprofen and troglitazone suppressed proliferation of cells of human chondrosarcoma (OUMS-27) at concentrations of 200 μM and 400 μM, and rosiglitazone suppressed at a concentration of 50 μM or higher.

Therefore, it was verified that zaltoprofen, rosiglitazone, and troglitazone are useful for prophylactic treatment or therapeutic treatment of chondrosarcoma.

As in Example 1, each drug was added as a solution in DMSO (dimethyl sulfoxide) prepared at a concentration 1000 times higher than the final concentration, and the solution was added in a volume of 0.1% of the volume of the medium. The same shall apply to the other drugs used in the following examples.

Figure 67:
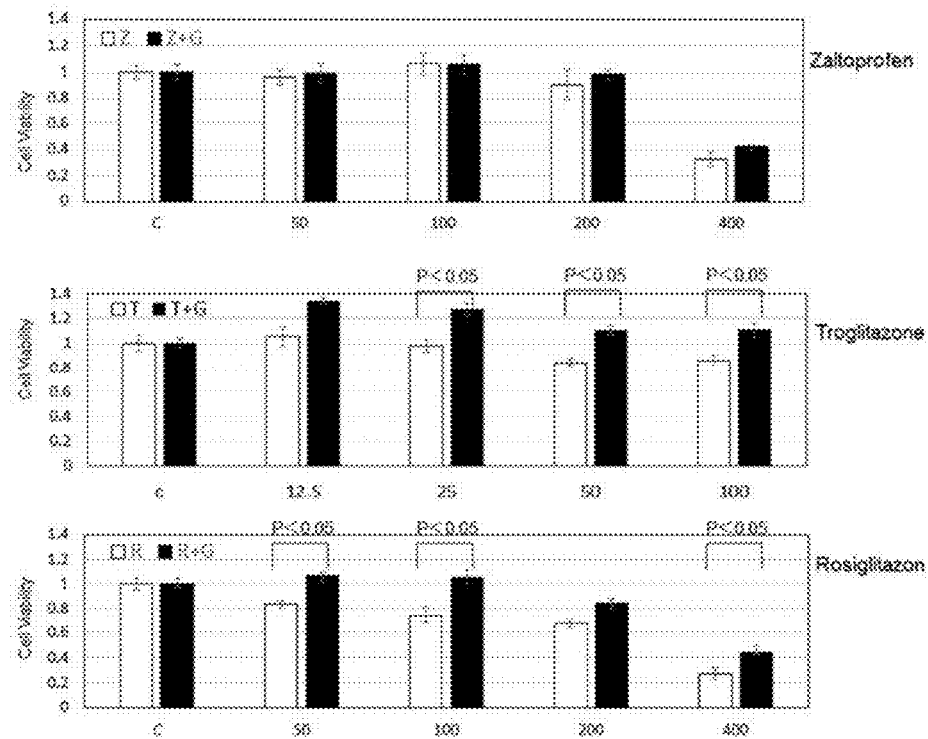
FIG. 67 Graphs showing results of suppression of proliferation of cultured cells of chondrosarcoma (OUMS-27) cultured in a zaltoprofen, rosiglitazone, or troglitazone-containing medium. The concentrations indicated under the horizontal axes are the concentrations of the drugs, and the vertical axes represent the live cell count measured on the basis of absorbance at 450 nm using CCK-8 (Dojindo). The black bars represent the live cell counts obtained after the cells were incubated with 1 µM (final concentration) of GW9662 (Sigma-Aldrich, M6191), which is an irreversible antagonist of PPARγ, and then zaltoprofen, rosiglitazone, or troglitazone was added. The white bars represent the live cell counts obtained after the cells were incubated only with DMSO not containing GW9662, and then zaltoprofen, rosiglitazone, or troglitazone was added.

Example 17: Analysis of Suppression of Proliferation of Cells of Human Chondrosarcoma Cell Line (OUMS-27) Cultured in the Presence or Absence of GW9662 Beforehand, Observed after Further Culture with Addition of Zaltoprofen, Rosiglitazone, or Troglitazone Cells of the human chondrosarcoma cell line, OUMS-27, were cultured in the same manner as that of Example 1 until they became sub-confluent, then GW9662 (Sigma Aldrich, M6191), which is an irreversible antagonist of PPARγ, was added to the cells at a final concentration of 1 μM, and the cells were cultured for 60 minutes. Zaltoprofen or troglitazone was added to the cells at various concentrations of 50, 100, 200, and 400 μM, or rosiglitazone was added at various concentrations of 12.5, 25, 50, and 100 μM, color development was performed with Cell Counting Kit-8 (CCK-8, Dojindo) 72 hours thereafter, absorbance was measured at 450 nm further 3 hours thereafter, and the result was compared with that observed with adding only DMSO not dissolving GW9662 (FIG. 67). As a result, it was successfully confirmed that proliferation of cells of human chondrosarcoma cell (OUMS-27) was suppressed by zaltoprofen, troglitazone, or rosiglitazone, and this cell proliferation-suppressing action was reduced by GW9662, which is an irreversible antagonist of PPARγ.

Therefore, it was verified that zaltoprofen, troglitazone, and rosiglitazone are useful for prophylactic treatment or therapeutic treatment of chondrosarcoma. It was also verified that zaltoprofen, troglitazone, and rosiglitazone suppress proliferation of chondrosarcoma through activation of PPARγ.

Figure 68:
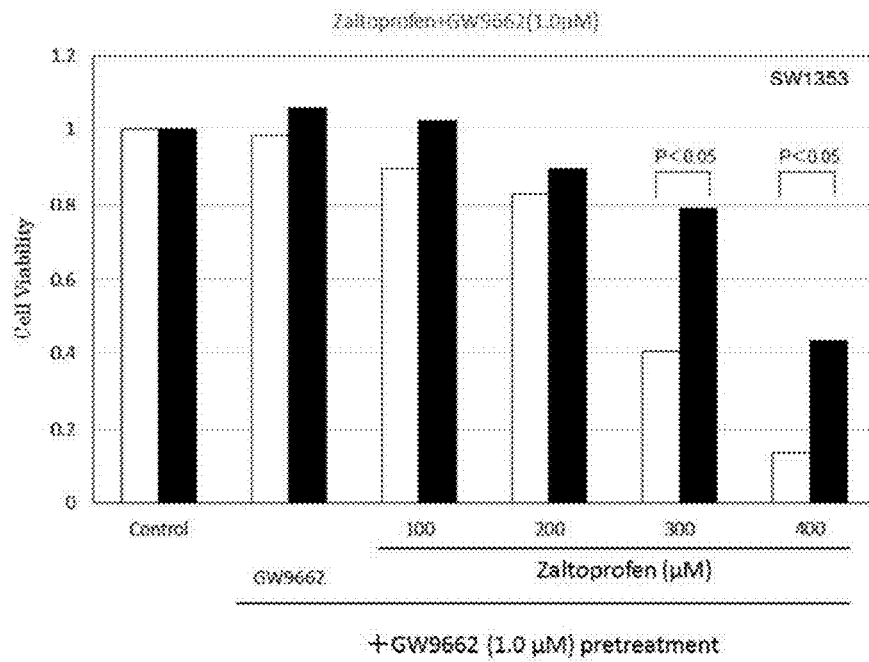
FIG. 68 A graph showing results of suppression of proliferation of cultured cells of chondrosarcoma (SW1353), which were cultured in a zaltoprofen-containing medium. Settings of the drugs are indicated under the horizontal axis, and the vertical axis represent the live cell count measured on the basis of absorbance at 450 nm using CCK-8 (Dojindo). The black bars represent the live cell counts obtained after the cells were incubated with 1 µM (final concentration) of GW9662, which is an irreversible antagonist of PPARγ, and then zaltoprofen was added. The white bars represent the live cell counts obtained after the cells were incubated only with DMSO not containing GW9662, and then zaltoprofen was added. The leftmost bars represent results of a group for which the cells were cultured without any drug, and the second bars from the left represent results of a group for which the cells were incubated with 1 µM of GW9662, and then DMSO not containing zaltoprofen was added.

Example 18: Analysis of Suppression of Proliferation of Cells of Human Chondrosarcoma Cell Line (SW1353) Cultured in the Presence or Absence of GW9662 Beforehand, Observed after Further Culture with Addition of Zaltoprofen Cells of the human chondrosarcoma cell line, SW1353, were cultured in the same manner as that of Example 1 until they became sub-confluent, then, GW9662, which is an irreversible antagonist of PPARγ, was added to the cells at a final concentration of 1 μM, and the cells were cultured for 60 minutes. Then, zaltoprofen was added to the cells at various concentrations of 100, 200, 300, and 400 μM, color development was performed with Cell. Counting Kit-8 (CCK-8, Dojindo) 72 hours thereafter, absorbance was measured at 450 nm further 3 hours thereafter, and the result was compared with the absorbance observed with adding only DMSO not dissolving GW9662 (FIG. 68). As a result, it was successfully confirmed that proliferation of cells of human chondrosarcoma (SW1353) was suppressed by zaltoprofen in a concentration-dependent manner, and the cell proliferation-suppressing action of zaltoprofen for human chondrosarcoma cells (SW1353) was markedly reduced by GW9662, which is an irreversible antagonist of PPARγ.

Therefore, it was verified that zaltoprofen is useful for prophylactic treatment or therapeutic treatment of chondrosarcoma. It was also verified that zaltoprofen suppresses proliferation of chondrosarcoma through activation of PPARγ.

Figure 69:
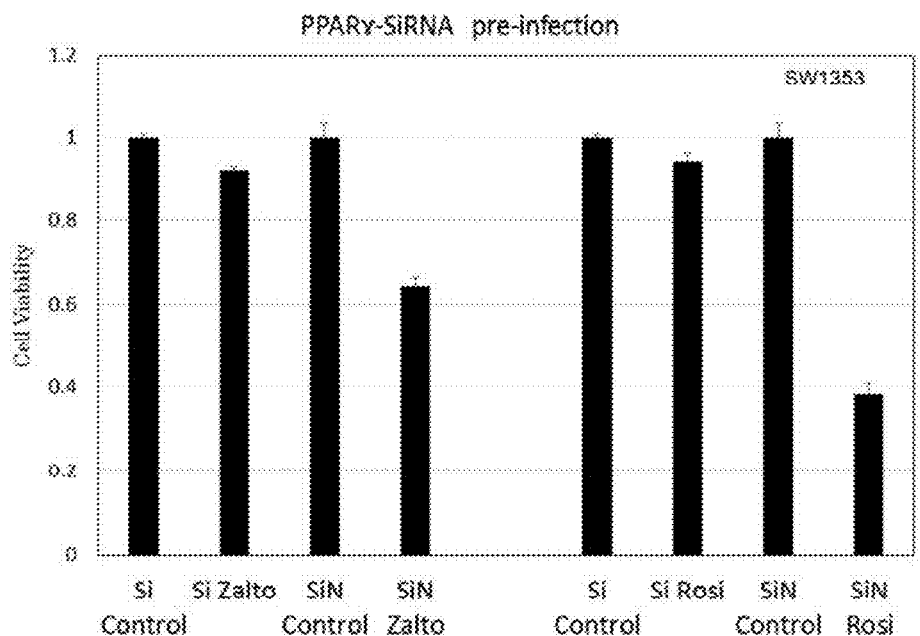
FIG. 69 A graph showing results of suppression of proliferation of cultured cells of chondrosarcoma (SW1353), which were cultured in a zaltoprofen or rosiglitazone-containing medium. The experimental groups are shown under the horizontal axis, and the vertical axis represent live cell count measured on the basis of absorbance at 450 nm using CCK-8 (Dojindo). From the left, the group indicated as "Si Control" is a group for which PPARγ gene expression was suppressed with PPARγ-siRNA, and then the cells were cultured with DMSO as a vehicle control, the group indicated as "Si Zalto" is a group for which PPARγ gene expression was suppressed with PPARγ-siRNA, and then the cells were cultured with zaltoprofen, the group indicated as "SiN Control" is a control group for which the cells were infected with negative-siRNA, and then cultured with DMSO as a vehicle control, the group indicated as "SiN Zalto" is a control group for which the cells were infected with negative-siRNA, and then cultured with zaltoprofen, the group indicated as "Si Control" is a group for which PPARγ gene expression was suppressed with PPARγ-siRNA, and then the cells were cultured with DMSO as a vehicle control, the group indicated as "Si Rosi" is a group for which PPARγ gene expression was suppressed with PPARγ-siRNA, and then cultured with rosiglitazone, the group indicated as "SiN Control" is a control group for which the cells were infected with negative-siRNA, and then cultured with DMSO as a vehicle control, and the group indicated as "SiN Rosi" is a control group for which the cells were infected with negative-siRNA, and then cultured with rosiglitazone.

Example 19: Analysis of Suppression of Proliferation of Cells of Human Chondrosarcoma Cell Line (SW1353) Cultured Beforehand in the Presence or Absence of siRNA that Suppresses Expression of PPARγ, Observed after Further Culture with Addition of Zaltoprofen or Rosiglitazone Cells of the human chondrosarcoma cell line, SW1353, was cultured in the same manner as that of Example 1 until they became sub-confluent, PPARγ-siRNA (Dharmacon, catalog number M-003436-02-0005) that selectively suppresses expression of PPARγ, or a control siRNA (Dharmacon, catalog number D-001206-14-05) was added to the cells at a final concentration of 100 nM, and the cells were cultured for 48 hours. Then, 400 μM of zaltoprofen or 100 μM of rosiglitazone was further added to the cells, color development was performed with Cell Counting Kit-8 (CCK-8, Dojindo) 24 hours thereafter, absorbance was measured at 450 nm further 3 hours thereafter, and the absorbance observed with the pretreatment with PPARγ siRNA was compared with the absorbance observed with the pretreatment with the control siRNA (double-stranded RNA of non-sense sequence not having gene expression-suppressing action) (FIG. 69). As a result, it was successfully confirmed that 400 μM zaltoprofen suppressed proliferation of cells of human chondrosarcoma (SW1353) by about 38%, and 100 μM rosiglitazone suppressed proliferation of cells of human chondrosarcoma (SW1353) by about 61%. Further, the cell proliferation-suppressing action of the drugs for the human chondrosarcoma cell line was substantially eliminated by suppressing expression of PPARγ by using siRNA.

Therefore, it was verified that zaltoprofen and rosiglitazone are useful for prophylactic treatment or therapeutic treatment of chondrosarcoma. It was also verified that expression of PPARγ is indispensable for suppression of proliferation of chondrosarcoma by zaltoprofen and rosiglitazone.

Figure 70:
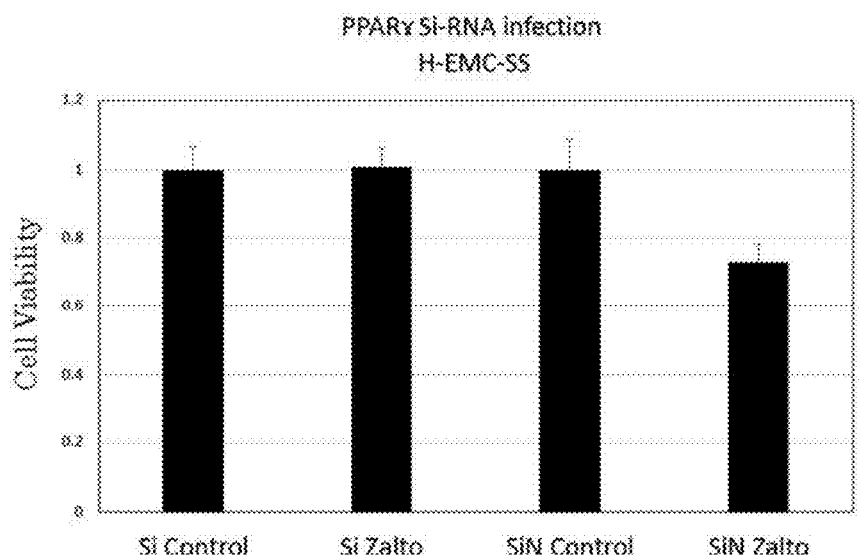
FIG. 70 A graph showing results of suppression of proliferation of cultured cells of chondrosarcoma (H-EMC-SS), which were cultured in a zaltoprofen-containing medium. The experimental groups are shown under the horizontal axis, and the vertical axis represent the live cell count measured on the basis of absorbance at 450 nm using CCK-8 (Dojindo). From the left, the group indicated as "Si Control" is a group for which PPARγ gene expression was suppressed with PPARγ-siRNA, and then the cells were cultured with DMSO as a vehicle control, the group indicated as "Si Zalto" is a group for which PPARγ gene expression was suppressed with PPARγ-siRNA, and then the cells were cultured with zaltoprofen, the group indicated as "SiN Control" is a control group for which the cells were infected with negative-siRNA, and then cultured with DMSO as a vehicle control, and the group indicated as "SiN Zalto" is a control group for which the cells were infected with negative-siRNA, and then cultured with zaltoprofen.

Example 20: Analysis of Suppression of Proliferation of Cells of Human Chondrosarcoma Cell Line (H-EMC-SS) Cultured Beforehand in the Presence or Absence of siRNA that Suppresses Expression of PPARγ, Observed after Further Culture with Addition of Zaltoprofen Cells of the human chondrosarcoma cell line, H-EMC-SS, were cultured in the same manner as that of Example 1 until they became sub-confluent, PPARγ siRNA (Dharmacon, catalog number M-003436-02-0005) that selectively suppresses expression of PPARγ, or a control siRNA (Dharmacon, catalog number D-001206-14-05) was added to the cells at a final concentration of 100 nM, and the cells were cultured for 48 hours. Then, 400 μM zaltoprofen was added to the cells, color development was performed with Cell Counting Kit-8 (CCK-8, Dojindo) 24 hours thereafter, absorbance was measured at 450 nm further 3 hours thereafter, and the absorbance observed with the pretreatment with PPARγ siRNA was compared with the absorbance observed with the pretreatment with the control siRNA (FIG. 70). As a result, it was successfully confirmed that zaltoprofen suppressed proliferation of cells of human chondrosarcoma (H-EMC-SS), and the cell proliferation-suppressing action of zaltoprofen for the human chondrosarcoma cell line (H-EMC-SS) was completely eliminated by siRNA that selectively suppresses expression of PPARγ.

Therefore, it was verified that zaltoprofen is useful for prophylactic treatment or therapeutic treatment of chondrosarcoma. It was also verified that expression of PPARγ is indispensable for suppression of proliferation of chondrosarcoma by zaltoprofen.

Figure 71:
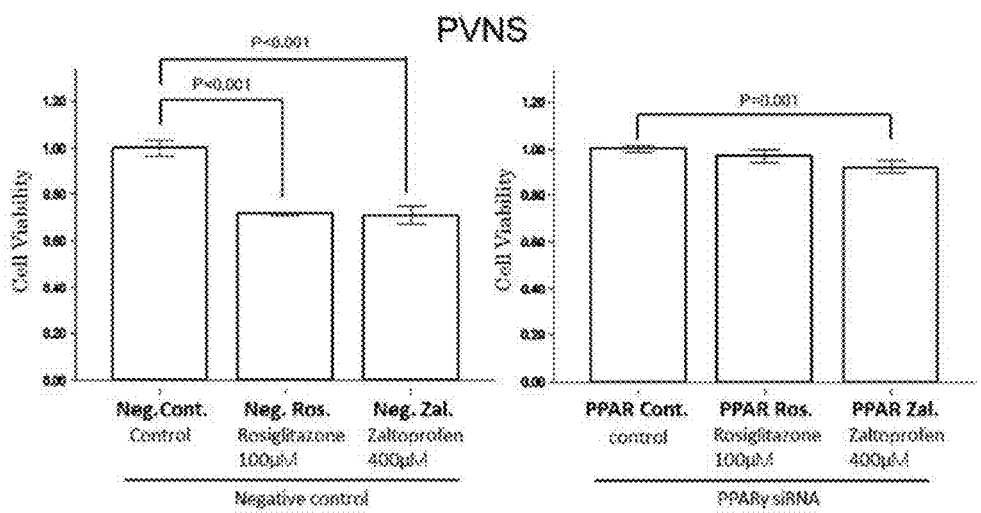
FIG. 71 Graphs showing results of suppression of proliferation of PVNS cells cultured in a zaltoprofen or rosiglitazone-containing medium. The experimental groups are shown under the horizontal axes, and the vertical axes represent the live cell count measured on the basis of absorbance at 450 nm using CCK-8 (Dojindo). The left graph shows results of the groups for which the cells were infected with a negative siRNA designed so as not to suppress gene expression. The right graph shows results of the groups for which the cells were infected with PPARγ- siRNA designed so as to suppress PPARγ gene expression. The groups of which results are shown in the left graph are, from the left, a group for which the cells were infected with a negative siRNA, and then cultured with DMSO as a vehicle control, a group for which the cells were infected with a negative siRNA, and then cultured with 100 μM rosiglitazone, and a group for which the cells were infected with a negative siRNA, and then cultured with 400 μM zaltoprofen. The groups of which results are shown in the right graph are, from the left, a group for which the cells were infected with PPARγ-siRNA, and then cultured with DMSO as a vehicle control, a group for which the cells were infected with PPARγ-siRNA, and then cultured with 100 μM rosiglitazone, and a group for which the cells were infected with PPARγ-siRNA, and then cultured with 400 μM zaltoprofen.

Example 21: Analysis of Suppression of Proliferation of Cultured Cells of Human PVNS Cultured Beforehand in the Presence or Absence of siRNA that Suppresses Expression of PPARγ, Observed after Further Culture with Addition of Rosiglitazone or Zaltoprofen PVNS cells excised from the patient of Example 8 (patient with giant cell tumor of tendon sheath in the right knee, in 30's, to whom only surgical operation was performed according to standard therapy) were cultured in the same manner as that of Example 8 until they became sub-confluent, then PPARγ siRNA (Dharmacon, catalog number M-003436-02-0005) that selectively suppresses expression of PPARγ, or a control siRNA (Dharmacon, catalog number D-001206-14-05) was added to the cells at a final concentration of 100 nM, and the cells were cultured for 48 hours. Then, 100 μM of rosiglitazone or 400 μM of zaltoprofen was added to the cells, color development was performed with Cell Counting Kit-8 (CCK-8, Dojindo) 24 hours thereafter, absorbance was measured at 450 nm further 3 hours thereafter, and the absorbance observed with the pretreatment with PPARγ siRNA was compared with the absorbance observed with the pretreatment with the control siRNA (FIG. 71). As a result, it was successfully confirmed that the cell proliferation-suppressing action of rosiglitazone or zaltoprofen for the human PVNS cells was substantially completely eliminated by siRNA that selectively suppresses expression of PPARγ.

Therefore, it was verified that zaltoprofen and rosiglitazone are useful for prophylactic treatment or therapeutic treatment of PVNS. It was also verified that expression of PPARγ is indispensable for suppression of proliferation of PVNS by zaltoprofen or rosiglitazone.

Figure 72:
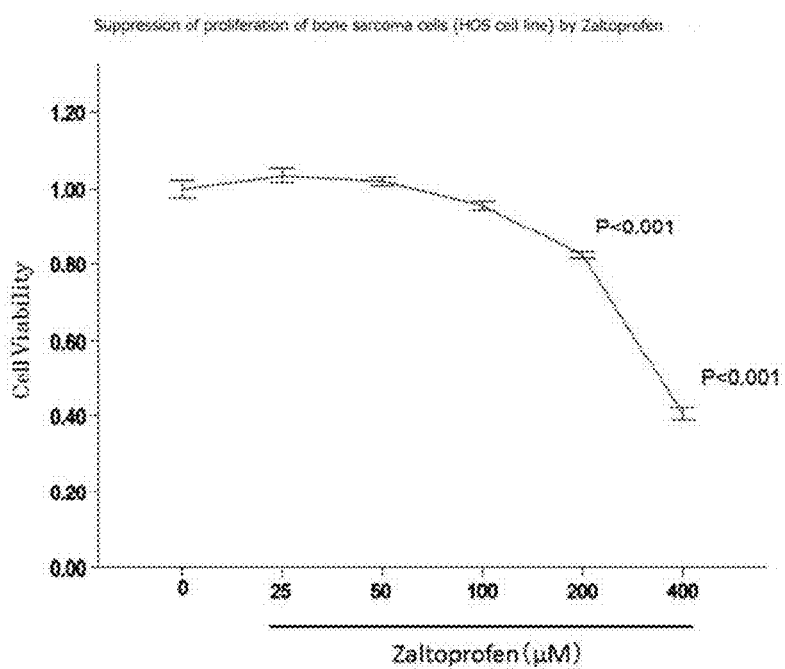
[FIG. 72] A Graph showing results of suppression of proliferation of cultured cells of bone sarcoma (HOS) cultured in a zaltoprofen-containing medium. The horizontal axis represents the concentration of the drug, and the vertical axis represents the relative number of migrated cells.

Example 22: Analysis of Suppression of Proliferation of Cells of Human Bone Sarcoma Cell Line (HOS) Observed after Culture with Addition of Zaltoprofen Cells of the human bone sarcoma cell line, HOS (purchased from American Type Culture Collection), were cultured in the same manner as that of Example 1 until they became sub-confluent. Zaltoprofen was added to the cells at concentrations of 25, 50, 100, 200 and 400 μM, color development was performed with Cell Counting Kit-8 (CCK-8, Dojindo) 72 hours thereafter, and absorbance was measured at 450 nm further 3 hours thereafter (FIG. 72). As a result, it was successfully confirmed that the cell proliferation of the cells of the human bone sarcoma cell line (HOS) was suppressed by zaltoprofen at concentrations of 100 μM, 200 μM, and 400 μM in a concentration-dependent manner. In particular, zaltoprofen could suppress proliferation of the cells of the human bone sarcoma cell line (HOS) by about 60% at the concentration of 400 μM.

Therefore, it was verified that zaltoprofen is useful for prophylactic treatment or therapeutic treatment of bone sarcoma.

Figure 73:
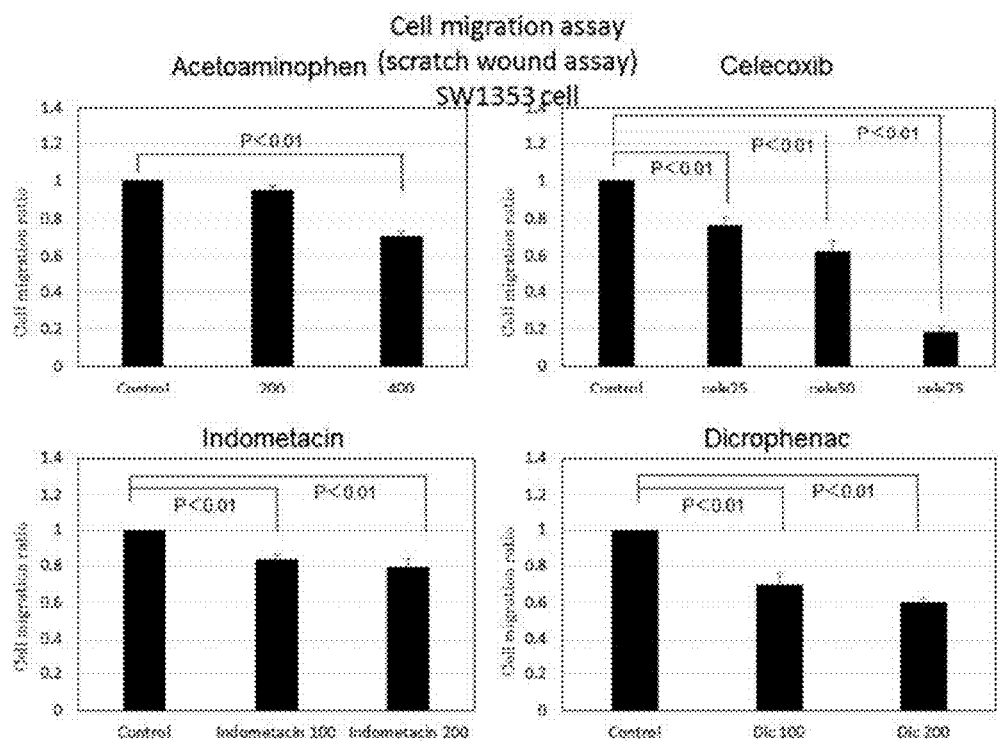
FIG. 73 Graphs showing results of suppression of cell migration of cultured cells of chondrosarcoma (HOS) cultured in an acetaminophen, celecoxib, indomethacin, or diclofenac-containing medium. The concentrations indicated under the horizontal axes are the concentrations of the drugs, and the vertical axes represent the relative number of migrated cells. The groups indicated as Control are vehicle control groups for which DMSO not containing each drug was added. The added drugs are shown at the tops of the graphs, respectively.
Figure 74:
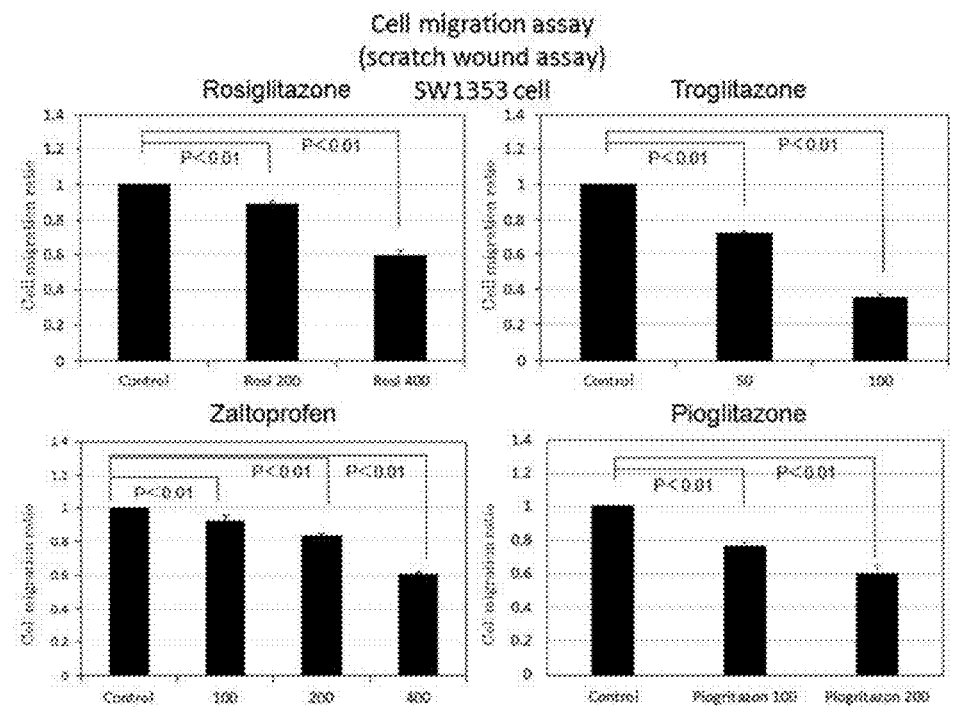
FIG. 74 Graphs showing results of suppression of cell migration of cultured cells of chondrosarcoma (SW1353) cultured in a rosiglitazone, troglitazone, zaltoprofen, or pioglitazone-containing medium. The concentrations indicated under the horizontal axes are the concentrations of the drugs, and the vertical axes represent the relative numbers of migrated cells. The groups indicated as Control are vehicle control groups for which DMSO not containing each drug was added. The added drugs are shown at the tops of the graphs, respectively.

Example 23: Analysis of Cell Migration of Cells of Human Chondrosarcoma Cell Line (SW1353) Observed after Culture with Addition of Non-Steroidal Anti-Inflammatory Agent or PPARγ Agonist The analysis of cell migration was performed by using a 6-well plate of TPP according to the method described in Takeuchi A, et al., Cancer Science, 104:740-749, 2013 (Low molecular weight heparin suppresses receptor for advanced glycation end products-mediated expression of malignant phenotype in human fibrosarcoma cells). Cells of the human chondrosarcoma cell line, SW1353, were cultured in the same manner as that of Example 1 until they became sub-confluent, and the cells were delaminated in a width of 1 mm using a micropipette tip (200 μl). Each of acetaminophen (200 μM and 400 μM), celecoxib (25 μM, 50 μM, and 75 μM), indomethacin (100 μM and 200 μM), diclofenac (100 μM and 200 μM), rosiglitazone (200 μM and 400 μM), troglitazone (50 μM and 100 μM), zaltoprofen (100 μM, 200 μM, and 400 μM), and pioglitazone (100 μM and 200 μM) was added to the cells at each of the final concentrations mentioned in the parentheses, and the cells were fixed with 4% paraformaldehyde 72 hours afterward, and stained with Crystal Violet. Then, area of the cells migrated to the region where the cells were delaminated was measured by using Image J software (http://rsb.info.nih.gov/ij/index.html) (FIGS. 73 and 74). As a result, it was successfully confirmed that all the compounds suppressed the cell migration of cells of the human chondrosarcoma cell line (SW1353) at all the set concentrations in a concentration-dependent manner. In particular, 75 μM celecoxib suppressed the cell migration of cells of the human chondrosarcoma cell line (SW1353) by higher than 80%, and 100 μM troglitazone suppressed the cell migration of cells of the human chondrosarcoma cell line (SW1353) by about 65%. Further, 400 μM zaltoprofen also suppressed the cell migration of cells of the human chondrosarcoma cell line (SW1353) by about 40%.

Therefore, it was verified that acetaminophen, celecoxib, indomethacin, diclofenac, rosiglitazone, troglitazone, zaltoprofen, and pioglitazone are useful for prevention of metastasis of chondrosarcoma.

Figure 75:
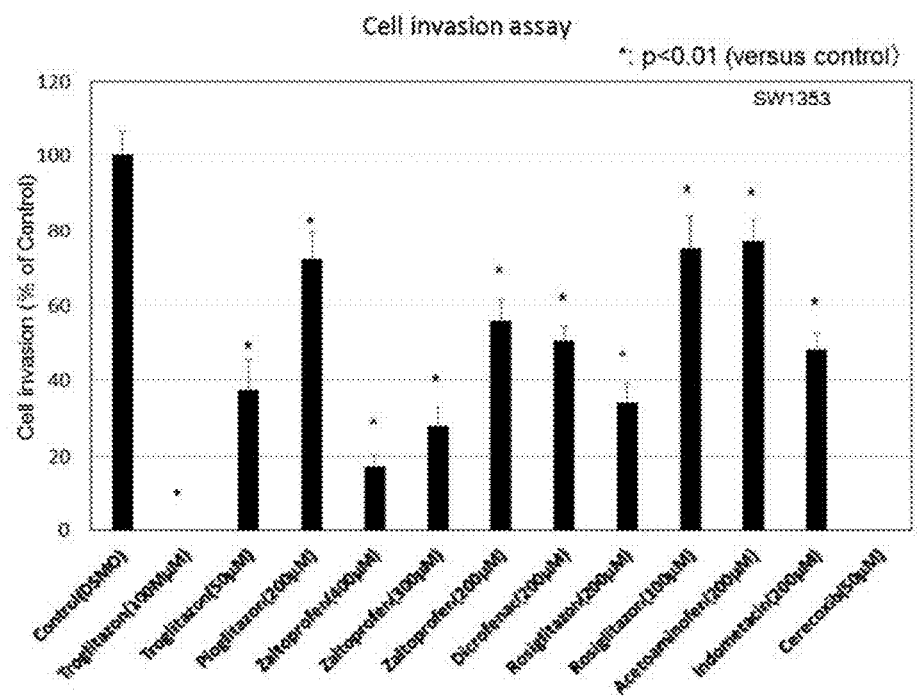
FIG. 75 A graph showing results of suppression of cell invasion of cultured cells of chondrosarcoma (SW1.353) cultured in a troglitazone, pioglitazone, zaltoprofen, diclofenac, rosiglitazone, acetaminophen, indomethacin, or celecoxib-containing medium. Types and concentrations of the drugs are shown under the horizontal axis, and the vertical axis represents the relative number of invaded cells. The group indicated as Control is a vehicle control group for which DMSO not containing any drug was added.
Figure 76:
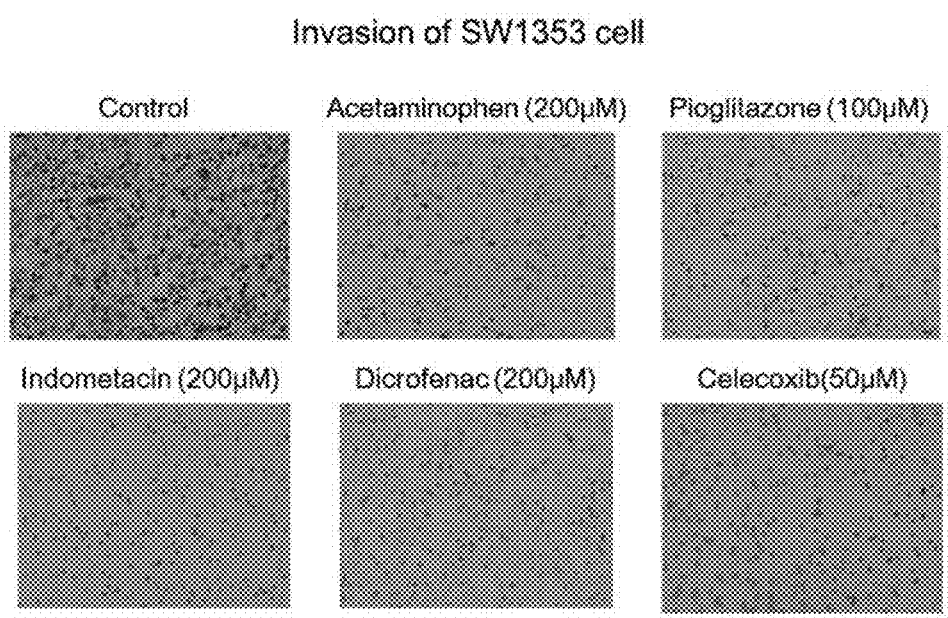
FIG. 76 Photographs showing cultured cells of chondrosarcoma (SW1353) causing cell invasion, which were cultured in an acetaminophen, pioglitazone, indomethacin, diclofenac, or celecoxib-containing medium. The group indicated as Control is a vehicle control group for which DMSO not containing any drug was added (see Example 24). For analysis of the cell invasion, Matrigel™ Invasion Chamber (BD Bioscience, catalog number 354480) using Matrigel as a matrix was used. There are shown photographs of the cells that invaded under the condition of adding each drug. They are photographs of the cells that passed through a membrane coated with Matrigel under the conditions that acetaminophen (200 μM), pioglitazone (100 μM), indomethacin (200 μM), diclofenac (200 μM), or celecoxib (50 μM) was added. "Control" represents a vehicle control for which only DMSO was added in the same volume as that used for addition of each drug. Under the condition of adding 50 μM celecoxib, there were cells in such a number that they only sparsely existed, and they rolled into small balls. Therefore, it can be seen that not only the suppression of cell invasion, but also cell injury was realized.
Figure 77:
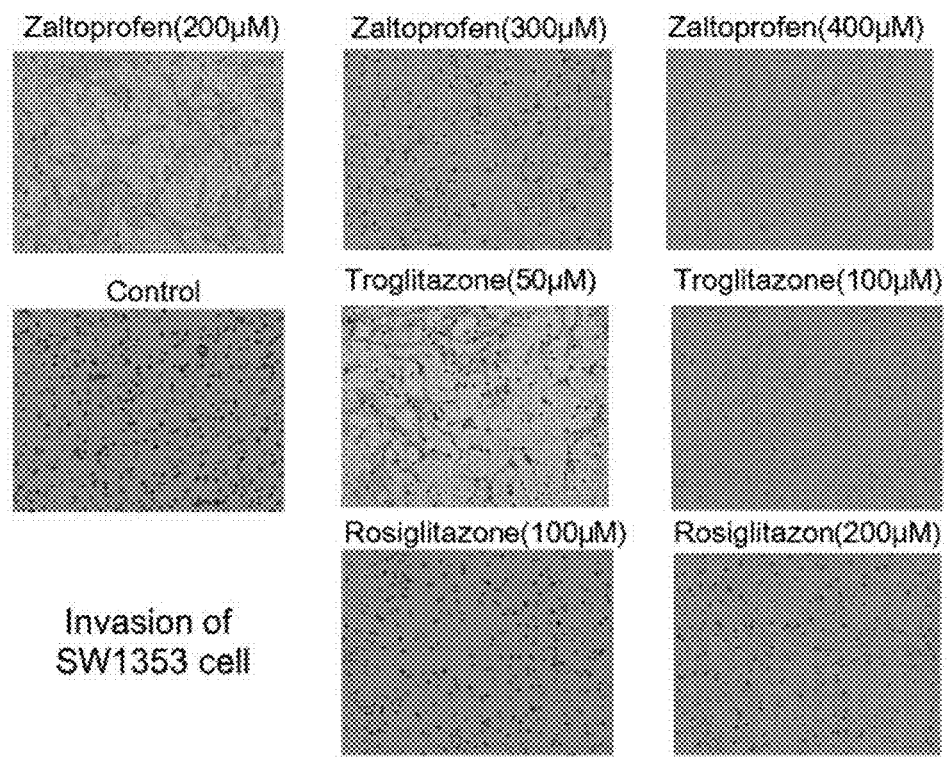
FIG. 77 Photographs showing cultured cells of chondrosarcoma (SW1353) causing cell invasion, which were cultured in a zaltoprofen, troglitazone, or rosiglitazone-containing medium. The group indicated as Control is a vehicle control group for which DMSO not containing any drug was added (see Example 24). For analysis of the cell invasion, Matrigel™ Invasion Chamber (BD Bioscience, catalog number 354480) using Matrigel as a matrix was used. There are shown photographs of the cells that invaded under the condition of adding each drug. They are photographs of the cells that passed through a membrane coated with Matrigel under the conditions of adding zaltoprofen (200 μM, 300 μM, 400 μM), troglitazone (50 μM, 100 μM), or rosiglitazone (100 μM, 200 μM). "Control" represents a vehicle control for which only DMSO was added in the same volume as that used for addition of the drugs. Under the condition that 400 μM zaltoprofen or 100 μM troglitazone was added, there were cells in such a number that they only sparsely existed, and they rolled into small balls. Therefore it can be seen that not only the suppression of cell invasion, but also cell injury was realized.

Example 24: Analysis of Cell Invasion of Cells of Human Chondrosarcoma Cell Line (SW1353) Observed after Culture with Addition of Non-Steroidal Anti-Inflammatory Agent or PPARγ Agonist For the analysis of cell invasion, Matrigel™ Invasion Chamber (BD Bioscience, catalog number 354480), which uses Matrigel as the matrix, was used. Cells of the human chondrosarcoma cell line, SW1353, were cultured in the same manner as that of Example 1 until they became sub-confluent, and then each of troglitazone (50 μM and 100 μM), pioglitazone (200 μM), zaltoprofen (200 μM, 300 μM, and 400 μM), diclofenac (200 μM), rosiglitazone (100 μM and 200 μM), acetaminophen (200 μM), indomethacin (200 μM), and celecoxib (50 μM) was added to the cells at each of the final concentrations mentioned in the parentheses, the cells were fixed with 4% paraformaldehyde 24 hours afterward, and stained with hematoxylin, and number of invaded cells was counted. As a result, it was successfully confirmed that all the compounds suppressed the cell invasion of cells of the human chondrosarcoma cell line (SW1353) at all the set concentrations in a concentration-dependent manner (FIG. 75). In particular, 100 μM troglitazone and 50 μM celecoxib completely suppressed the cell invasion of cells of the human chondrosarcoma cell line (SW1353), and 400 μM zaltoprofen also suppressed the cell invasion to lower than 20%. FIGS. 76 and 77 show microphotographs of invaded cells fixed by immersion into a 4% paraformaldehyde solution, and stained with hematoxylin (magnification is 200 times). From the microphotographs of FIGS. 76 and 77, the patterns of the invaded cells can be understood. With the conditions of addition of 100 μM troglitazone or 50 μM celecoxib, there were cells in such a number that they only sparsely existed, and they rolled into small balls. Therefore, it can be seen that not only the suppression of cell invasion, but also cell injury was realized.

Therefore, it was verified that troglitazone, pioglitazone, zaltoprofen, diclofenac, rosiglitazone, acetaminophen, indomethacin, and celecoxib are useful for prevention of metastasis of chondrosarcoma.

Figure 78:
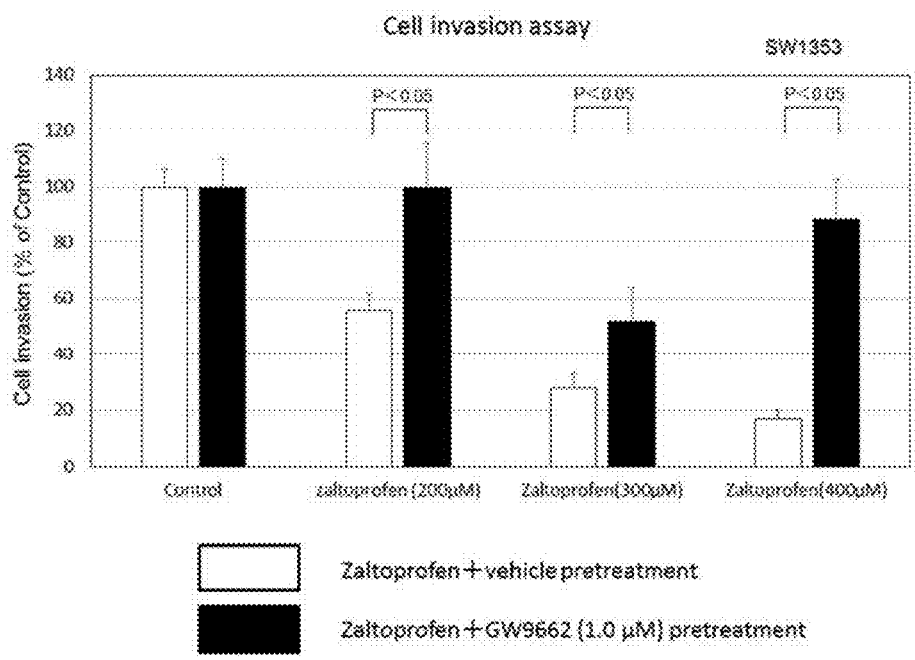
FIG. 78 A graph showing results of suppression of cell invasion of cultured cells of chondrosarcoma (SW1353) cultured in a zaltoprofen-containing medium. Settings of the drugs are shown under the horizontal axis, and the vertical axis represents the relative number of invaded cells. The black bars represent the relative numbers of invaded cells obtained after the cells were incubated beforehand with 1 μM (final concentration) of GW9662, which is an irreversible antagonist of PPARγ, and then zaltoprofen was added. The white bars represent the relative numbers of invaded cells obtained after the cells were incubated only with DMSO not containing GW9662, and then zaltoprofen was added. The leftmost bars represent results of a group for which the cells were cultured without any drug, the second bars from the left represent results of a group for which the cells were incubated with 1 μM GW9662, and then 200 zaltoprofen was added, the third bars from the left represent results of a group for which the cells were incubated with 1 μM GW9662, and then 300 μM zaltoprofen was added, and the rightmost bars represent results of a group for which the cells were incubated with 1 μM GW9662, and then 400 μM zaltoprofen was added.

Example 25: Analysis of Cell Invasion of Cells of Human Chondrosarcoma Cell Line (SW1353) Cultured Beforehand in the Presence or Absence of GW9662 Observed after Further Culture with Addition of Zaltoprofen Cells of the human chondrosarcoma cell line, SW1353, were cultured in the same manner as that of Example 1 until they became sub-confluent, then, GW9662, which is an irreversible antagonist of PPARγ, was added to the cells at a final concentration of 1 μM, and the cells were cultured for 60 minutes. Then, zaltoprofen was added to the cells at various concentrations of 200, 300, and 400 μM, cell invasion was measured with Matrigel™ Invasion Chamber (BD Bioscience, catalog number 354480) 24 hours afterward, and the result was compared with the degree of cell invasion observed with addition of only DMSO not dissolving GW9662 (FIG. 78). As a result, it was successfully confirmed that the cell invasion of human chondrosarcoma cells (SW1353) was suppressed by higher than 80% with 400 μM zaltoprofen, and the suppression of the cell invasion of the human chondrosarcoma cells (SW1353) with 400 zaltoprofen was substantially eliminated by GW9662 (1 μM), which is an irreversible antagonist of PPARγ.

Therefore, it was verified that zaltoprofen is useful for prevention of metastasis of chondrosarcoma. Further, it was also verified that zaltoprofen prevents metastasis of chondrosarcoma through activation of PPARγ.

Example 26: Analysis of Curative Effect of Zaltoprofen (Soleton Tablet (Registered Trademark) on Patient with Giant Cell Tumor of Bone Soleton Tablet 80 (generic name: zaltoprofen, 80 mg, Nippon Chemiphar) was administered to patients with giant cell tumor of bone at a dose of 3 tablets per day (one tablet was administered in the morning, at noon, and in the evening). Four weeks after the start of the administration, the tumor size was evaluated by imaging based on simple Roentgen contrast method, X-ray CT, and MRI (nuclear magnetic resonance imaging). Then, the tumors were excised from patients for whom surgical operation was possible, administration of zaltoprofen was continued at a dose of 240 mg per day (one 80 mg tablet was administered at the time of breakfast, lunch, and supper), and the tumor size was evaluated by imaging based on simple Roentgen contrast method, X-ray CT, and MRI (nuclear magnetic resonance imaging) every 16 weeks. Also for patients for whom surgical operation was difficult, administration of zaltoprofen was continued at a dose of 240 mg per day (one 80 mg tablet was administered at the time of breakfast, lunch, and supper), and the tumor size was evaluated by imaging based on simple Roentgen contrast method, X-ray CT, and MRI (nuclear magnetic resonance imaging) every 8 weeks.

The cases for which therapeutic treatment with zaltoprofen was performed are summarized in FIG. 79. Zaltoprofen was administered to total 13 patients of giant cell tumor of bone including 8 male patients from 21 years old to 39 years old and 5 female patients from 25 years old to 68 years old. As for the affected parts, 4 patients' affected at the pelvic part, 2 patients at distal part of thighbone, 1 patient at proximal part of fibula (2 patients, if 1 patient affected as the primary lesion of metastasis to the lung is included), 1 patient at distal part of tibia, 1 patient at knee part, 1 patient at proximal part of humerus, 1 patient at sacrum, and 2 patients with metastases to the lung (1 patient affected at proximal part of fibula, and 1 patient affected at proximal part of tibia as primary lesions). The patients affected at the pelvic part were all female patients, and the patients affected at the distal part of thighbone or proximal part of fibula were all male patients. There were 5 patients with recurrence. In particular, the tumor of the patient of case f (25 years old, female, proximal part of right humerus) was of the 5th recurrence, and the tumor of the patient of the case a (34 years old, female, pelvis) was of the 3rd recurrence. Further, there were two patients having metastases to the lung (cases e and m), and in particular, the patient of the case m (21 years old, male, proximal part of right tibia) suffered from multiple metastases to the lung.

For the patient of the case j (32 years old, male, sacrum), administration of Zometa (registered trademark), which is zoledronic acid hydrate injection, and artery embolization were used in combination. For the patient of the case m (21 years old, male, proximal part of right tibia, multiple metastases to lung), Zometa (registered trademark), which is zoledronic acid hydrate injection, was used in combination, after treatment with denosumab, which is an anti-RANKL human monoclonal antibody. For the patient of the case b (32 years old, female, pelvis), a treatment with zaltoprofen was performed after completion of the clinical trial with denosumab.

As a result of the administration of zaltoprofen, as shown in FIGS. 79 and 80, among the 13 cases of the patients of giant cell tumor of bone, they were diagnosed partial response (PR) in one case, stable disease (SD) in 11 cases, and progressive disease (PD) in one case. In the case a, for which diagnosis was partial response (PR), the tumor size shrank by more than 70%, the giant cell tumor of bone was then excised by surgical operation, and no recurrence has been observed up to today. The patient of the case in (21 years old, male, proximal part of right tibia), evaluated as progressive disease (PD), suffered from multiple metastases to the lung, and was temporarily evaluated as stable disease (SD), but the tumor tends to increase again with progress of time. As for the patient of the case 1 (31 years old, male, left knee part), who showed 19.8% of increase of the size of the giant cell tumor of bone, it has been found that he took only about a half of the prescribed dose according to the judgment of the patient himself.

For all the patients of the cases a, c, d, e, and f, whose giant cell tumors of bone shrank, any treatment was not performed except for the administration of zaltoprofen, and therefore it was considered that the tumors were shrank as a result of the taking of zaltoprofen.

Figure 81:
FIG. 81 Photographs showing transversal MRI images of affected part (proximal part of left fibula) of a giant cell tumor of bone patient (case c) who took zaltoprofen (Soleton Tablet (registered trademark)), which photographs were obtained before (Dec. 13, 2012) and after (Feb. 13, 2013) taking zaltoprofen. It can be seen that, as a result of taking zaltoprofen over about nine weeks, the diameter of the giant cell tumor of bone shrank from 23.3 mm to 21.0 mm.

Transversal MRI images of the affected part (proximal part of left fibula) of the patient of the case c obtained before the administration of zaltoprofen (Dec. 13, 2012) and after the administration (Feb. 13, 2013) are shown in FIG. 81. It can be seen that, as a result of the taking of zaltoprofen over about nine weeks, the diameter of the giant cell tumor of bone shrank from 23.3 mm to 21.0 mm.

Figure 82:
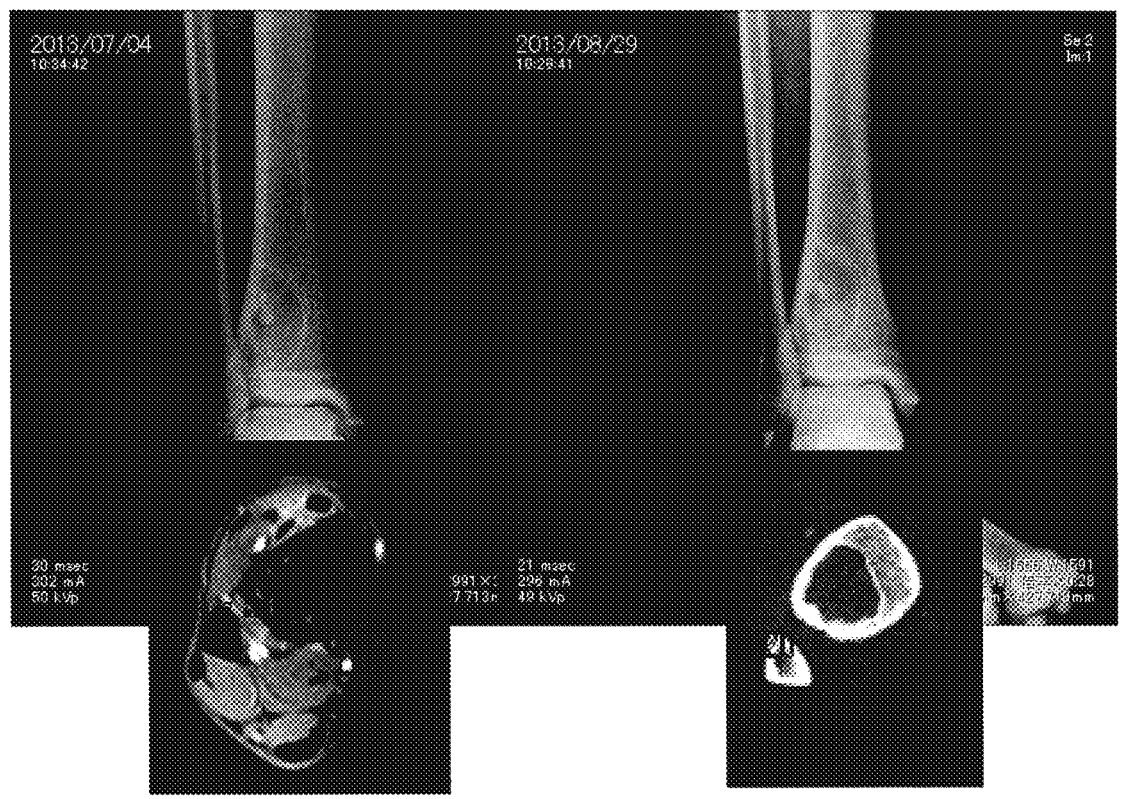
FIG. 82 Photographs showing frontal and transversal MRI images of affected part (distal part of right tibia) of a giant cell tumor of bone patient (case d) who took zaltoprofen (Soleton Tablet (registered trademark)), which photographs were obtained before (Jul. 4, 2013) administration of zaltoprofen, and X-ray CT images of the same obtained after the administration (Aug. 29, 2013). It can be seen that, as a result of taking zaltoprofen over about eight weeks, the diameter of the giant cell tumor of bone shrank from 21.7 mm to 20.5 mm.

Frontal and transversal MRI images and CT images of the affected part (distal part of right tibia) of the patient of the case d obtained before the administration of zaltoprofen (Jul. 4, 2013) and after the administration (Aug. 29, 2013) are shown in FIG. 82. It can be seen that, as a result of the taking of zaltoprofen over about eight weeks, the diameter of the giant cell tumor of bone shrank from 21.7 mm to 20.5 mm.

Transversal MRI images of the affected part (metastasis part in the lung) of the patient of the case e obtained before the administration of zaltoprofen (Jan. 17, 2013) and after the administration (Sep. 19, 2013) are shown in FIG. 83. It can be seen that, as a result of the taking of zaltoprofen over about 35 weeks, the diameter of the giant cell tumor of bone metastasized to the lung shrank from 8.2 mm to 7.3 mm.

As described above, shrinkage of giant cell tumor of bone could be confirmed in the patients who took zaltoprofen. Further, in the 12 cases except for one case in which multiple metastases to the lung were seen, the giant cell tumors of bone were evaluated as partial response (PR) or stable disease (SD). Further, shrinkage of giant cell tumor of bone metastasized to the lung was also observed (case e, FIG. 83).

Then, because improving tendency was also seen for subjective symptoms of the patients, ability to perform everyday activities was also evaluated according to the Karnofsky Performance Status (KPS). KPS is an evaluation method for classifying patient's conditions into ten stages of score 100 to 0 according to the criteria shown in FIG. 84, and a higher score means better performance of the patient for everyday activities. The evaluation results of KPS of the patients of giant cell tumor of bone before and after the administration of zaltoprofen are shown in FIG. 85.

In the patients of the cases a, c, and d, whose giant cell tumors of bone shrank as a result of the taking of zaltoprofen, the KPS scores were improved from a state that "considerable clinical symptoms, but normal activities are possible with efforts" (score 80) to a state that "slight clinical symptoms, and normal activities are possible" (score 90).

In the patient of the case g, the giant cell tumor of bone did not shrink, but it also did not grow, and the KPS scores were markedly improved from a state that "considerable clinical symptoms, but normal activities are possible with efforts" (score 80) to a state of "no clinical symptoms" (score 100).

Unexpectedly, improving tendency of the KPS score was also observed in patients who showed slightly growing tendency of giant cell tumor of bone. In the patient of the case k, in spite of the growth of the giant cell tumor of bone by about 10%, the KPS score improved from a state that "considerable clinical symptoms, but normal activities are possible with efforts" (score 80) to a state that "slight clinical symptoms, and normal activities are possible" (score 90). Similarly, in the patient of the case j, in spite of the growth of the giant cell tumor of bone by about 6%, the KPS score dramatically improved from a state that "nursing and periodical medical intervention are needed in consideration of conditions of disease" (score 50) to a state that "slight clinical symptoms, and normal activities are possible" (score 90).

A further surprising finding was that, even for the patient of giant cell tumor of bone of the case m (21 years old, male, proximal part of right tibia), who suffered from multiple metastases to the lung, and evaluated as progressive disease (PD), the KPS score improved from a state that "slight clinical symptoms, and normal activities are possible" (score 90) to a state of "no clinical symptoms" (score 100).

Further, there was no case in which the KPS score worsened among the cases of giant cell tumor of bone in which the patients took zaltoprofen.

In addition, since there were 6 cases (cases a, b, d, g, i, and j) where observation of hardening of bones was brought by the taking of zaltoprofen as determined on the basis of X-ray CT images, it was estimated that taking of zaltoprofen restored the bones, and improved mechanical strength thereof.

As described above, administration of zaltoprofen provided shrinkage or arrest of growth of tumors of the giant cell tumor of bone patients, observation of hardening of bones, and marked improvement in ability of the patients to carry out everyday activities. Further, any new metastasis of giant cell tumor of bone was not observed during the taking of zaltoprofen. Furthermore, no recurrence of giant cell tumor of bone could be confirmed during the taking of zaltoprofen in the patients who were subjected to an ablative operation of giant cell tumor of bone.

Therefore, it was verified that zaltoprofen is useful for prophylactic treatment, therapeutic treatment, and prevention of metastasis of giant cell tumor of bone in human patients. Further, it was also verified that zaltoprofen restores or forms bones of human patients suffering from giant cell tumor of bone, and improves ability to carry out everyday activities.

Example 27: Analysis of Curative Effect of Zaltoprofen (Soleton Tablet (Registered Trademark)) on PVNS Patients PVNS patients were administered with 3 tablets per day (one tablet was administered in the morning, at noon, and in the evening) of Soleton Tablet 80 (generic name; zaltoprofen, 80 mg, Nippon Chemiphar). Four weeks after the start of the administration, the tumor size was evaluated by imaging based on simple Roentgen contrast method, X-ray CT, and MRI (nuclear magnetic resonance imaging). Then, the tumors were excised from patients for whom surgical operation was possible, administration of zaltoprofen was continued at a dose of 240 mg per day (one 80 mg tablet was administered at the time of breakfast, lunch, and supper), and the tumor size was evaluated by imaging based on simple Roentgen contrast method, X-ray CT, and MRI (nuclear magnetic resonance imaging) every 16 weeks. Also for patients for whom surgical operation was difficult, administration of 240 mg zaltoprofen per day (one 80 mg tablet was administered at the time of breakfast, lunch, and supper) was continued, and the tumor size was evaluated by imaging based on simple Roentgen contrast method, X-ray CT, and MRI (nuclear magnetic resonance imaging) every 8 weeks.

Figure 87:
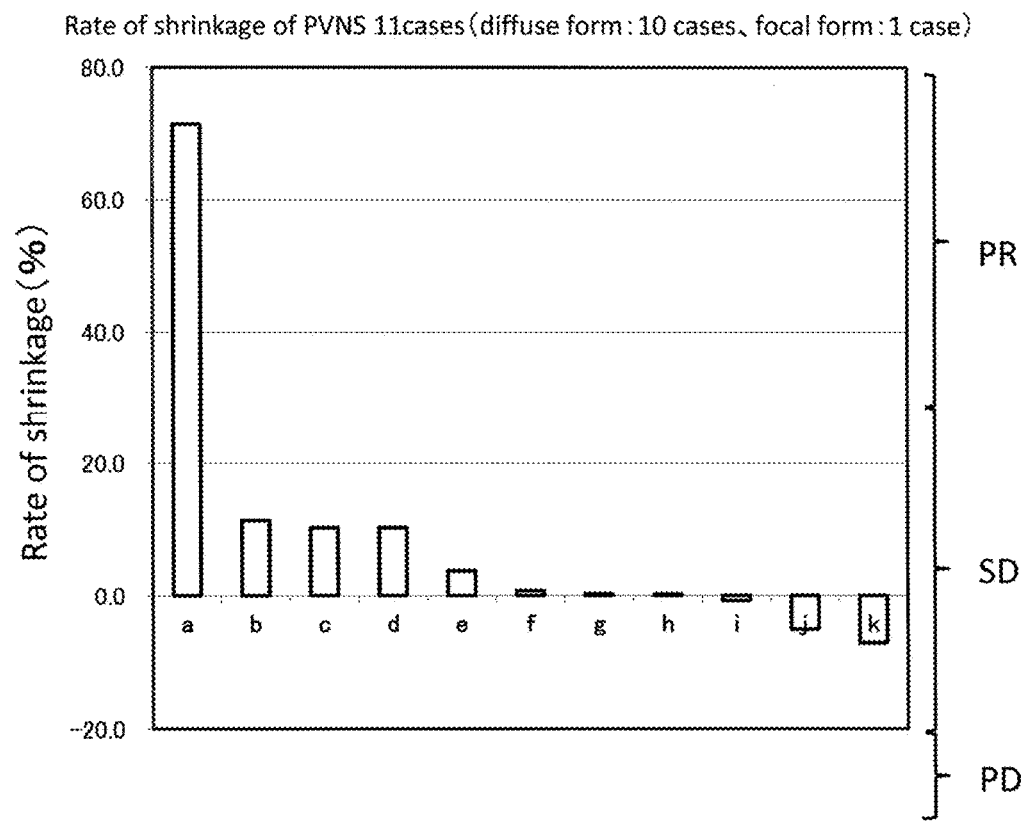
FIG. 87 A graph showing shrinking ratios of PVNS of PVNS patients who took zaltoprofen (Soleton Tablet (registered trademark)). The vertical axis represents the shrinking ratio. A shrinking ratio of 70% means that the giant cell tumor of bone shrank to a size of 30% of the size observed before taking zaltoprofen, and a shrinking ratio of −10% means that the giant cell tumor of bone grew to a size of 110% of the size observed before taking zaltoprofen. The alphabets mentioned under the horizontal axis are alphabets for specifying the cases (see FIG. 86).

The cases for which therapeutic treatment with zaltoprofen was performed are summarized in FIG. 86. Zaltoprofen was administered to total 14 PVNS patients including 5 male patients from 26 years old to 65 years old and 9 female patients from 16 years old to 62 years old. As for the affected parts, 8 patients affected at the knee joint, 4 patients at ankle joint, 1 patient at shoulder joint, and 1 patient at wrist joint. The case of 1 patient who affected PVNS at the wrist joint was that of focal PVNS, and all the other 13 cases were diffuse PVNS cases. Ten cases out of the 14 cases were those of recurrence of PVNS. As shown in FIGS. 86 and 87, among 11 cases for which the response rate was successfully determined, one case was judged to be partial response (PR), and the other 10 cases were judged to be stable disease (SD).

The patient of the case h (16 years old, female, right ankle joint), the patient of the case i (26 years old, male, right knee), and the patient of the case e (40 years old, male, left wrist joint) were subjected to PVNS ablative operation. Further, for the patient of the case l (31 years old, female, left ankle joint), the patient of the case m (30 years old, female, left knee), and the patient of the case n (38 years old, female, ankle joint), the administration of zaltoprofen was started after the PVNS ablative operation, and therefore the response rate was not successfully determined.

All the patients of the cases a, b, c, d, e, and f whose PVNS shrank were not subjected to any treatment except for the administration of zaltoprofen, and accordingly it was considered that the tumors were shrunk by the administration of zaltoprofen.

Figure 88:
FIG. 88 Photographs showing frontal MRI images of affected part (shoulder joint) of a PVNS patient (case a) who took zaltoprofen (Soleton Tablet (registered trademark)), which photographs were obtained before (Sep. 6, 2012) and after (Aug. 20, 2013) administration of zaltoprofen. It can be seen that, as a result of taking zaltoprofen over about 50 weeks, the diameter of PVNS shrank from 27.7 mm to 7.9 mm.

Frontal MRI images of the affected part (shoulder joint) of the patient of the case a obtained before the administration of zaltoprofen (Sep. 6, 2012) and after the administration (Aug. 20, 2013) are shown in FIG. 88. It can be seen that, as a result of the taking of zaltoprofen over about 50 weeks, the diameter of PVNS shrank from 27.7 mm to 7.9 mm.

Figures 89, 90:
FIG. 89 Photographs showing sagittal MRI images of affected part (right knee joint) of a PVNS patient (case c) who took zaltoprofen (Soleton Tablet (registered trademark)), which photographs were obtained before (Dec. 6, 2012) and after (Aug. 1, 2013) administration of zaltoprofen. It can be seen that, as a result of taking zaltoprofen over about 35 weeks, the major axis of PVNS shrank from 59.5 mm to 47.2 mm.
FIG. 90 A table summarizing effects of continuous administration of zaltoprofen (Soleton Tablet (registered trademark)) on PVNS. There are mentioned KPS determined before the start of taking zaltoprofen and after continuous taking of zaltoprofen, and shrinking ratio of giant cell tumor of bone for each case.

Sagittal MRI images of the affected part (right knee joint) of the patient of the case c obtained before the administration of zaltoprofen (Dec. 6, 2012) and after the administration (Aug. 1, 2013) are shown in FIG. 89. It can be seen that, as a result of the taking of zaltoprofen over about 35 weeks, the diameter of PVNS shrank from 59.5 mm to 48.0 mm.

As described above, shrinkage of PVNS could be confirmed in all the patients who took zaltoprofen. Further, all the PVNS patients who took zaltoprofen were judged to be partial response (PR) or stable disease (SD).

The evaluation results of the PVNS patients obtained before and after the administration of zaltoprofen according to the Karnofsky Performance Status (KPS) are shown in the table of FIG. 90. In the patients of the cases a and b whose PVNS shrank as a result of the taking of zaltoprofen, the KPS score was dramatically improved from a state that "patient can care himself or herself, but normal activities or works are impossible" (score 70) to a state of "no clinical symptoms" (score 100). Similarly, in the patients of the cases c and d whose PVNS shrank as a result of the taking of zaltoprofen, the KPS score was improved from a state that "considerable clinical symptoms, but normal activities are possible with efforts" (score 80) to a state that "slight clinical symptoms, and normal activities are possible" (score 90).

Further, there was no case in which the KPS score worsened among the cases of PVNS in which the patients took zaltoprofen.

As described above, as a result of the taking of zaltoprofen, tumors of the PVNS patients shrank, or growth of the tumors was arrested, and ability to carry out everyday activities was markedly improved. Further, during the taking of zaltoprofen, any new metastasis of PVNS was not observed. Furthermore, no recurrence of PVNS could be confirmed during the taking of zaltoprofen in the patients who were subjected to an ablative operation of PVNS.

Therefore, it was verified that zaltoprofen is useful for prophylactic treatment, therapeutic treatment, and prevention of metastasis of PVNS in human patients. Further, it was also verified that zaltoprofen improves ability to carry out everyday activities of human patients who suffer from PVNS.

On the basis of the examples mentioned above, it was verified that the pharmaceutical agent of the present invention containing a substance having a PPARγ-agonistic activity and/or a PPARγ expression-inducing activity as an active ingredient is useful as an agent for prophylactic treatment, therapeutic treatment, or prevention of metastasis of giant cell tumor occurring in bone and soft tissue, chondrosarcoma, or bone sarcoma.

INDUSTRIAL APPLICABILITY

The agent for prophylactic treatment, therapeutic treatment, or prevention of metastasis of the present invention is effective for patients of giant cell tumor occurring in bone and soft tissue, chondrosarcoma, or bone sarcoma, or persons with a possibility of developing giant cell tumor occurring in bone and soft tissue, chondrosarcoma, or bone sarcoma. Further, according to the present invention, search for a novel therapeutic agent for giant cell tumor occurring in a bone and soft tissue, chondrosarcoma, or bone sarcoma is enabled by choosing a test substance that controls a PPARγ gene and apoptosis, or fat cell differentiation.

What is claimed is:

1. A method for therapeutic treatment of giant cell tumor occurring in bone or soft tissue, for decreasing tumor size of giant cell tumor occurring in bone or soft tissue, for suppressing proliferation of giant cell tumor occurring in bone or soft tissue, or for prevention of recurrence and/or metastasis of giant cell tumor occurring in bone or soft tissue, which comprises orally administering an effective amount of zaltoprofen for therapeutic treatment, decreasing tumor size, suppressing proliferation or prevention of recurrence and/or metastasis to a mammal in need thereof.

2. The method according to claim 1, wherein the mammal is a human.

3. The method according to claim 1, wherein the zaltoprofen is administered in 240 mg per day to 720 mg per day.

4. The method according to claim 1, wherein the zaltoprofen is administered in 480 mg per day.

5. The method according to claim 1, wherein the giant cell tumor occurring in bone or soft tissue is selected from the group consisting of giant cell tumor of bone, giant cell tumor of tendon sheath, and pigmented villonodular synovitis.

6. The method according to claim 1, which further comprises administering denosumab.

7. The method according to claim 1, which further comprises administering a bisphosphonate.

8. A method for therapeutic treatment of bone sarcoma or chondrosarcoma, for decreasing tumor size of bone sarcoma or chondrosarcoma, for suppressing proliferation of bone sarcoma or chondrosarcoma, or for prevention of recurrence and/or metastasis of bone sarcoma or chondrosarcoma, which comprises orally administering an effective amount of zaltoprofen for therapeutic treatment, decreasing tumor size, suppressing proliferation or prevention of recurrence and/or metastasis to a mammal in need thereof.

9. The method according to claim 8, wherein the mammal is a human.

10. The method according to claim 8, wherein the zaltoprofen is administered in 240 mg per day to 720 mg per day.

11. The method according to claim 8, wherein the zaltoprofen is administered in 480 mg per day.

12. The method according to claim 8, which further comprises administering denosumab.

13. The method according to claim 8, which further comprises administering a bisphosphonate.

14. The method according to claim 13, wherein the bisphosphonate consists of one or more kinds of bisphosphonates selected from the group consisting of etidronate, clodronate, tiludronate, pamidronate, neridronate, olpadronate, alendronate, ibandronate, tiludronate, incadroate, risedronate, minodronate, zoledronate, sovadronate, medronate, risendronate, amino-olpadronate, simadronate, pyridronate, rezidronate, and EB1053.

* * * * *